US012685769B2

(12) United States Patent
Carranza Sandmeier et al.

(10) Patent No.: US 12,685,769 B2
(45) Date of Patent: Jul. 21, 2026

(54) VACCINE

(71) Applicant: GlaxoSmithKline Biologicals SA, Rixensart (BE)

(72) Inventors: Maria Paula Carranza Sandmeier, Schlieren (CH); Rainer Follador, Schlieren (CH); Veronica Gambillara Fonck, Schlieren (CH); Stefan Jochen Kemmler, Schlieren (CH); Patricia Martin Killias, Schlieren (CH); Michael Thomas Kowarik, Schlieren (CH); Gerd Martin Lipowsky, Schlieren (CH); Gerald Johann Posch, Schlieren (CH); Fabio Serventi, Schlieren (CH); Dominique Nicolas Sirena, Schlieren (CH)

(73) Assignee: GlaxoSmithKline Biologicals SA, Rixensart (BE)

( * ) Notice: Subject to any disclaimer, the term of this patent is extended or adjusted under 35 U.S.C. 154(b) by 376 days.

(21) Appl. No.: 18/001,525

(22) PCT Filed: Jun. 17, 2021

(86) PCT No.: PCT/EP2021/066343
§ 371 (c)(1),
(2) Date: Dec. 12, 2022

(87) PCT Pub. No.: WO2021/259743
PCT Pub. Date: Dec. 30, 2021

(65) Prior Publication Data
US 2023/0293657 A1        Sep. 21, 2023

Related U.S. Application Data

(60) Provisional application No. 63/043,883, filed on Jun. 25, 2020.

(30) Foreign Application Priority Data

| | | | |
|---|---|---|---|
| Jun. 25, 2020 | (EP) | | 20182138 |
| Jun. 25, 2020 | (EP) | | 20182139 |

(51) Int. Cl.
| | |
|---|---|
| *A61K 39/385* | (2006.01) |
| *A61K 39/00* | (2006.01) |
| *A61K 39/108* | (2006.01) |
| *A61P 31/04* | (2006.01) |
| *C07K 14/26* | (2006.01) |
| *C12N 9/10* | (2006.01) |

(52) U.S. Cl.
CPC ........ *A61K 39/385* (2013.01); *A61K 39/0266* (2013.01); *A61P 31/04* (2018.01); *C07K 14/26* (2013.01); *C12N 9/1077* (2013.01); *C12N 9/1081* (2013.01); *C12Y 204/02036* (2013.01); *C12Y 204/99019* (2015.07); *A61K 2039/6068* (2013.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil et al. |
| 7,232,569 | B2 | 6/2007 | Frey et al. |
| 7,579,011 | B2 | 8/2009 | Frey et al. |
| 7,815,896 | B2 | 10/2010 | Frey et al. |
| 8,753,864 | B2 | 6/2014 | Aebi et al. |
| 8,846,342 | B2 | 9/2014 | Wacker et al. |
| 9,238,830 | B2 | 1/2016 | Feldman et al. |
| 9,725,515 | B2 | 8/2017 | Anderson et al. |
| 10,307,474 | B2 | 6/2019 | Faridmoayer |
| 10,500,263 | B2 | 12/2019 | Porro |
| 11,220,676 | B2 | 1/2022 | Wacker et al. |
| 11,286,283 | B2 | 3/2022 | Braun et al. |
| 11,446,370 | B2 | 9/2022 | Geurtsen et al. |
| 11,819,544 | B2 | 11/2023 | Faridmoayer et al. |
| 11,931,405 | B2 | 3/2024 | Geurtsen et al. |
| 12,398,380 | B2 | 8/2025 | Wacker et al. |
| 2003/0219826 | A1 | 11/2003 | Robbins et al. |
| 2005/0239215 | A1 | 10/2005 | Hisada et al. |
| 2011/0274720 | A1 | 11/2011 | Wacker et al. |
| 2014/0005362 | A1 | 1/2014 | Bujko et al. |
| 2015/0037359 | A1 | 2/2015 | Schellenberger et al. |

(Continued)

FOREIGN PATENT DOCUMENTS

| | | | |
|---|---|---|---|
| CN | 105102480 | A | 11/2015 |
| CN | 106062203 | A | 10/2016 |

(Continued)

OTHER PUBLICATIONS

Definition of Antigenic, Retrieved from https://dictionary.cambridge.org/us/dictionary/english/antigenic, accessed on Jul. 24, 2025, pp. 1-3.
Feng L., et al., "The Acidic Tumor Microenvironment: a Target for Smart Cancer Nano-Theranostics," National Science Review, 2018, vol. 5, pp. 269-286.
International Preliminary Report on Patentability for International Application No. PCT/EP2022/086835, mailed Jul. 4, 2024, 12 Pages.
International Search Report and Written Opinion for International Application No. PCT/EP2022/086835, mailed May 15, 2023, 17 Pages.

(Continued)

*Primary Examiner* — Oluwatosin A Ogunbiyi

(57) ABSTRACT

The present invention relates to the field of immunogenic compositions and vaccines, their manufacture, host cells which can be used in their manufacture and the use of such immunogenic compositions and vaccines in medicine. More particularly, it relates to *Klebsiella pneumoniae* O-antigens, conjugates comprising a *K. pneumoniae* O-antigen, host cells suitable for their production and immunogenic compositions or vaccines containing at least one *Klebsiella pneumoniae* O-antigen.

Figures 1A, 1B:
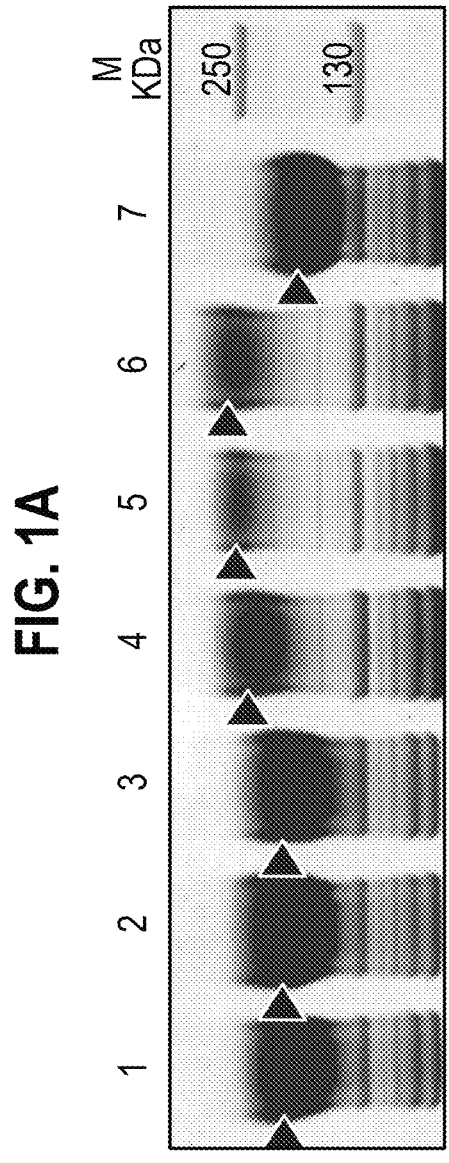

25 Claims, 10 Drawing Sheets
Specification includes a Sequence Listing.

(56) References Cited

U.S. PATENT DOCUMENTS

| 2017/0121691 | A1 | 5/2017 | Wacker et al. | |
| 2021/0077607 | A1 | 3/2021 | Faridmoayer et al. | |
| 2021/0268095 | A1* | 9/2021 | Donald | A61P 37/04 |
| 2022/0298205 | A1 | 9/2022 | Braun et al. | |
| 2024/0316172 | A1 | 9/2024 | Geurtsen et al. | |
| 2025/0222093 | A1 | 7/2025 | Geurtsen et al. | |

FOREIGN PATENT DOCUMENTS

| CN | 107496932 | A | 12/2017 |
| EP | 3492481 | A1 | 6/2019 |
| EP | 3225690 | B1 | 2/2022 |
| JP | 2011514155 | A | 5/2011 |
| JP | 2013524844 | A | 6/2013 |
| JP | 2015533497 | A | 11/2015 |
| JP | 2015533511 | A | 11/2015 |
| JP | 2017523794 | A | 8/2017 |
| JP | 2018517729 | A | 7/2018 |
| WO | WO-9603649 | A1 | 2/1996 |
| WO | WO-03074687 | A1 | 9/2003 |
| WO | WO-2007109812 | A2 | 9/2007 |
| WO | WO-2007109813 | A1 | 9/2007 |
| WO | WO-2013130683 | A2 | 9/2013 |
| WO | WO-2013130684 | A1 | 9/2013 |
| WO | WO-2014057109 | A1 | 4/2014 |
| WO | WO-2014072405 | A1 | 5/2014 |
| WO | 2014114926 | A1 | 7/2014 |
| WO | WO-2015124769 | A1 | 8/2015 |
| WO | 2016020499 | A2 | 2/2016 |
| WO | 2016044773 | A1 | 3/2016 |
| WO | WO-2016202872 | A1 | 12/2016 |
| WO | WO-2017067964 | A1 | 4/2017 |
| WO | 2019106201 | A1 | 6/2019 |
| WO | WO-2019117976 | A1 | 6/2019 |
| WO | WO-2019241672 | A2 | 12/2019 |
| WO | 2021259743 | A2 | 12/2021 |

OTHER PUBLICATIONS

Stojkovic K., et al., "Identification of D-Galactan-III As Part of the Lipopolysaccharide of Klebsiella Pneumoniae Serotype O1," Frontiers in Microbiology, Apr. 25, 2017, vol. 8, Article 684, pp. 1-8, DOI: 10.3389/fmich.2017.00684, XP055649061.

Office Action Received in Co-Pending U.S. Appl. No. 17/619,334, dated Jul. 30, 2025, 46 Pages. See paragraphs 57-61.

Extended European Search Report for European Application No. 19183033.0, mailed Feb. 3, 2020, 9 Pages.

International Search Report for International Application No. PCT/EP2020/067782, mailed Oct. 9, 2020, 07 Pages.

Written Opinion for International Application No. PCT/EP2020/067782, mailed Oct. 9, 2020, 09 Pages.

Kato N., et al., "Design of Transmembrane Peptides and Control of Their Self-organization Toward the Fabrication of Nanoacrchitectures," Meiji Daigaku Kagaku Gijutsu Kenkyujo Nenpo—Annual Report Dfthe Institute of Sciences and Technology, Meiji University, Meiji Daigaku Gijutsu Kenkyujo, Kawasaki, JP, Jan. 1, 2009, vol. 51, pp. 39-41. (See International Search Report for International Application No. PCT/EP2020/067782 for concise explanation of relevance.).

Livio S, et al., "Shigella Isolates From the Global Enteric Multicenter Study Inform Vaccine Development," Clinical Infectious Diseases, Oct. 1, 2014, vol. 59, pp. 933-941.

Partial European Search Report for European Application No. 19183033.0, mailed Oct. 30, 2019, 10 Pages.

Riley P., et al., "A Better Way to His-Tag," The Scientist Magazine, Apr. 10, 2005, 1 Page, [Retrieved on Jul. 31, 2020] Retrieved from URL: https://www.the-scientist.com/letter/a-better-way-to-his-tag-48888.

Terpe K., "Overview of Tag Protein Fusions: From Molecular and Biochemical Fundamentals to Commercial Systems," Applied Microbiology and Biotechnology, Springer Berlin Heidelberg, Jan. 1, 2003, vol. 60, No. 5, pp. 523-533.

Aas ei ai., "Neisseria gonorrhoeae O-linked pilin glycosylation: functional anaylses define both the biosynthetic pathway and glycan structure," Molecular Microbiology, vol. 65, No. 3, 2007 (Published online Jun. 29, 2007), pp. 607-624.

Abeyrathne P.D., et al., "Functional Characterization of WaaL, a Ligase Associated with Linking O-Antigen Polysaccharide to the Core of Pseudomonas aeruginosa Lipopolysaccharide," Journal of Bacteriology, May 2005, vol. 187, No. 9, pp. 3002-3012.

Allured V.S., et al., "Structure of Exotoxin a of Pseudomonas Aeruginosa at 3.0-Angstrom Resolution," Proceedings of the National Academy of Sciences of the United States of America, Mar. 1986, vol. 83, pp. 1320-1324.

Avci F.Y., et al., "A Mechanism for Glycoconjugate Vaccine Activation of the Adaptive Immune System and Its Implications Tor Vaccine Design," Nature Medicine, Dec. 2011, vol. 17, No. 12, pp. 1602-1609 (9 page total).

Bentley S.D., et al., "Genetic Analysis of the Capsular Biosynthetic Locus From All 90 Pneumococcal Serotypes," PLOS Genetics, Public Library of Science, Mar. 10, 2006, vol. 2, No. 3, e31, 8 Pages.

Borud B., et al., "Genetic, Structural, and Antigenic Analyses of Glycan Diversity in the O-Linked Protein Glycosylation Systems of Human Neisseria Species," Journal of Bacteriology, Jun. 2010, vol. 192, No. 11, pp. 2816-2829.

Clarke B.R., "Molecular Basis for the Structural Diversity in Serogroup O2-Antigen Polysaccharides in Klebsiella Pneumoniae," Journal of Biological Chemistry, US, Mar. 30, 2018, vol. 293, No. 13, DOI:10.1074/jbc.RA117.000646, ISSN 0021-9258, pp. 4666-4679, XP055475277.

Co-Pending U.S. Appl. No. 18/718,636.

Dagan R., et al., "Glycoconjugate Vaccines and Immune Interference: A Review," Vaccine, 2010, vol. 28, No. 34, pp. 5513-5523, (Available online Jun. 25, 2010).

Eldman, et al., "Engineering N-linked protein glycosylation with diverse 0 antigen lipopolysaccharide stuctures in Escherichia coli", Proceedings of the National Academy of Sciences, National Academy of Sciences, US; Feb. 22, 2005; vol. 102 (8); pp. 3016-3021.

Faridmoayer A., et al., "Extreme Substrate Promiscuity of the Neisseria Oligosaccharyl Transferase Involved in Protein O-Glycosylation," Journal of Biological Chemistry, Dec. 12, 2008, vol. 283, No. 50, pp. 34596-34604.

Faridmoayer A., et al., "Functional Characterization of Bacterial Oligosaccharyltransferases Involved in O-Linked Protein Glycosylation," Journal of Bacteriology, Nov. 2007, vol. 189, No. 22, pp. 8088-8098.

Fisher et al., "Production of Secretory and Extracellular N-Linked Glycoproteins in Escherichia coli", Applied and Environmental Microbiology, (20110000), Feb. 2011, vol. 77, No. 3, doi:10.1128/AEM.01901-10, pp. 871-881, XP055142701.

Ge Q., et al., "The C-Terminal Domain of AcrA is Essential for the Assembly and Function of the Multidrug Efflux Pump AcrAB-ToIC," Journal of Bacteriology, Jul. 2009, vol. 191, No. 13, pp. 4365-4371.

Gray G.L., et al., "Cloning, Nucleotide Sequence, and Expression in Escherichia Coli of the Exotoxin a Structural Gene of Pseudomonas Aeruginosa," Proceedings of the National Academy of Sciences of the United States of America, May 1984, vol. 81, pp. 2645-2649.

Guachalla L.M., et al., "Discovery of Monoclonal Antibodies Cross-Reactive to Novel Subserotypes of K. Pneumoniae O3," Scientific Reports, Dec. 1, 2017, vol. 7, No. 1, pp. 1-13, XP055874583, DOI: 10.1038/s41598-017-06682-2, Published Online on Jul. 26, 2017, Retrieved from URL: https://www.nature.com/articles/s41598-017-06682-2.pdf.

Guan D., et al., "Split Intein Mediated Ultra-Rapid Purification of Tagless Protein (SIRP)," Biotechnology and Bioengineering, Sep. 2013, vol. 110, No. 9, pp. 2471-2481.

Hartley M.D., et al., "Biochemical Characterization of the O-Linked Glycosylation Pathway in Neisseria gonorrhoeae Responsible for Biosynthesis of Protein Glycans Containing N,N'-Diacetylbacillosamine," Biochemistry, 2011, vol. 50, No. 22, pp. 4936-4948.

(56) References Cited

OTHER PUBLICATIONS

Hayashi K., et al., "Highly Accurate Genome Sequences of *Escherichia coli* K-12 Strains MG1655 and W3110," Molecular Systems Biology, 2006, vol. 2, 2006.0007, pp. 1-5, doi:10.1038/msb4100049, XP055355138.

Ho M.M., et al., "Preclinical Laboratory Evaluation of a Bivalent *Staphylococcus aureus* Saccharide: Exotoxin A Protein Conjugate Vaccine," Human Vaccines, May-Jun. 2006, vol. 2, No. 3, pp. 89-98, (Published online on May 8, 2006).

hsieh P-F., et al., "D-Galactan II is an Immunodominant Antigen in O1 Lipopolysaccharide and Affects Virulence in Klebsiella Pneumoniae: Implication in Vaccine Design," Frontiers in Microbiology, Nov. 19, 2014, vol. 5, Article 608, 055836982, pp. 1-14, DOI:10.3389/fmicb. 2014.00608, Retrieved from URL: https://www.ncbi.nlm.nih.gov/pmc/articles/PMC4237132/pdf/fmieb-05-00608.pdf.

Ihssen J., et al., "Production of Glycoprotein Vaccines in *Escherichia coli*," Microbial Cell Factories, Aug. 11, 2010, vol. 9, No. 61, pp. 1-13, Jan. 1, 2010, DOI: 10.1186/1475-2859-9-61, XP055158778, [Retrieved on Dec. 15, 2014], Retrieved from URL: http://www.microbialcellfactories.com/content/pdf/1475-2859-9-61.pdf.

International Preliminary Report on Patentability for International Application No. PCT/EP2021/066336, mailed Jan. 5, 2023, 8 Pages.

International Preliminary Report on Patentability for International Application No. PCT/EP2021/066343, mailed Jan. 5, 2023, 15 Pages.

International Preliminary Report on Patentability for International Application No. PCT/IB2021/055361, mailed Dec. 29, 2022, 13 Pages.

International Search Report and Written Opinion for International Application No. PCT/EP2021/066336, mailed Oct. 6, 2021, 12 Pages.

International Search Report for International Application No. PCT/IB2021/055361, mailed Nov. 12, 2021, 6 Pages.

Kelly S.D., et al., "Klebsiella Pneumoniae O1 and O2ac Antigens Provide Prototypes for an Unusual Strategy for Polysaccharide Antigen Diversification," Journal of Biological Chemistry, US, Jul. 1, 2019, vol. 294, o. 28, pp. 10863-10876, DOI: 10.1074/jbc.RA119. 008969, ISSN: 0021-9258, XP055812409.

Kensil C.R., et al., "Structural and Immunological Characterization of the Vaccine Adjuvant QS-21," Vaccine Design: The Subunit and Adjuvant Approach, Plenum Press, New York, 1995, Chapter 22, pp. 525-541.

Klein J.S., et al., "Design and Characterization of Structured Protein Linkers with Differing Flexibilities", Protein Engineering, Design & Selection, 2014, vol. 27, No. 10, pp. 325-330, DOI :10.1093/protein/gzu043, XP055699923.

Kotloff K.L., et al., "Burden and Aetiology of Diarrhoeal Disease in Infants and Young Children in Developing Countries (the Global Enteric Multicenter Study. GEMS): a Prospective, Case-control Study," Lancet, Jul. 20, 2013, vol. 382, No. 9888, pp. 209-222, (Published online May 14, 2013).

Kowarik M., et al., "N-Linked Glycosylation of Folded Proteins by the Bacterial Oligosaccharyltransferase," Science, Nov. 17, 2006, vol. 314, pp. 1148-1150 (4 Pages).

Kubler-Kielb J., et al., "Immunochemical Studies of Shigella Flexneri 2a and 6, and Shigella Dysenteriae Type 1 a-specific Polysaccharide-core Fragments and Their Protein Conjugates as Vaccine Candidates," Carbohydrate Research, May 15, 2010, vol. 345, No. 11, pp. 1600-1608, DOI: 10.1016/j.carres.2010.05.006, ISSN: 0008-6215, 055838307, GB.

Kubler-Kielb J., et al., "O-acetylation in the O-specific Polysaccharide Isolated From Shigella Flexner Serotype 2a," Carbohydrate Research, 2007, vol. 342, pp. 643-647, (Available online on Nov. 2006).

Leff D.N., et al., "In Mice, CpG Outstrips Classic Vaccine Adjuvant 5-Fold: Clinical Trial Coming So DNA Motif Gooses Immune Antigenicity Response," Bioworld, Nov. 5, 1998, 3 Pages(total).

Li H., et al., "Understanding Protein Glycosylation Pathways in Bacteria," Future Microbiology, 2017, vol. 12, No. 1, pp. 59-72, (Published online Sep. 30, 2016).

Liu J., et al., "Use of Quantitative Molecular Diagnostic Methods to Identify Causes of Diarrhoea in Children: A Reanalysis of the GEMS Case-control Study,", The Lancet, Sep. 24, 2016, vol. 388, pp. 1291-1301, DOI:10.1016/S0140-6736(16)31529-X, XP029741279.

Lukac M., et al., "Toxoid of Pseudomonas aeruginosa Exotoxin A Generated by Deletion of an Active-Site Residue," Infection and Immunity, Dec. 1988, vol. 56, No. 12, pp. 3095-3098.

Musumeci M.A., et al., "In Vitro Activity of Neisseria Meningitidis PgIL O-Oligosaccharyltransferase With Diverse Synthetic Lipid Donors and a UDP-Activated Sugar," The Journal of Biological Chemistry, Apr. 12, 2013, vol. 288, No. 15, pp. 10578-10587.

Pan C., et al., "Biosynthesis of Conjugate Vaccines Using an O-Linked Glycosylation System," American Society for Microbiology, Apr. 26, 2016, vol. 7, No. 2, e00443-16, pp. 1-11.

Perepelov A.V., et al., "Shigella Fiexneri O-Antigens Revisited: Final Elucidation of the O-Acetylation Profiles and a Survey of the O-Antigen Structure Diversity," FEMS Immunology and Medical Microbiology, 2012, vol. 66, pp. 201-210.

Pogue G.P., et al., "Production of Pharmaceutical-grade Recombinant Aprotinin and a Monoclonal Antibody Product Using Plant-based Transient Expression Systems," Plant Biotechnology Journal, 2010, vol. 8, pp. 638-654, doi:10.1111/j.1467-7652.2009.00495.x, XP055038517.

Poolman J.T., et al., "Extraintestinal Pathogenic *Escherichia coli*, A Common Human Pathogen: Challenges for Vaccine Development and Progress in the Field," Journal of Infectious Diseases, Jan. 1, 2016, vol. 213, No. 1, pp. 6-13, 2015.

Ravenscroft N., et al., "11 Characterization and Immunogenicity of a Shigella Flexneri 2A O-Antigen Bioconjugate Vaccine Candidate," Glycobiology, Aug. 20, 2019, vol. 29, No. 9, pp. 669-680, DOI: 10.1093/glycob/cwz044, ISSN: 0959-6658, XP055838251, Retrieved from URL: http://academic.oup.com/glycob/advance-articlepdf/doi/10.1093/glycob/cw2044/29012700/cwz044.pdf.

Ravenscroft N., et al., "Purification and Characterization of a Shigella Conjugate Vaccine, Produced by Glycoengineering *Escherichia coli*," Glycobiology, Sep. 9, 2015, cwv077, vol. 26, No. 1, 12 Pages, DOI: 10.1093/glycob/cwv077, ISSN: 0959-6658, XP055333443.

Rosano ei al., "Recombinant protein expression in *Escherichia coli*: advances and challenges," Frontiers in Microbiology, vol. 5, Article 172, Apr. 17, 2014, pp. 1-17.

Ruan X., et al., "The Waal O-Antigen Lipopolysaccharide Ligase Has Features in Common With Metal ion-Independent Inverting Glycosyltransferases," Glycobiology, 2012, vol. 22, No. 2, pp. 288-299.

Schulz B.L., et al., "Identification of Bacterial Protein O-Oligosaccharyltransferases and Their Glycoprotein Substrates," PLOS One, May 3, 2013, vol. 8, Issue 5, e62768, pp. 1-11.

Shepherd et al., "Comparison of O-antigen gene clusters of *Escherichia coli* (Shigella) sonnei and Plesiomonas shigelloides 017: sonnei gained its current plasmid-borne O-antigen genes from P. shigelloides in a recent event", Infect. Immun., (20000000), vol. 68, No. 10, pp. 6065-6061.

StouteJ.A., et al., "A Preliminary Evaluation of a Recombinant Circumsporozoite Protein Vaccine Against Plasmodium Falciparum Malaria," The New England Journal of Medicine, Jan. 9, 1997, vol. 336, pp. 86-91.

Sun P., et al., "Design and Production of Conjugate Vaccines Against S. Paratyphi a Using an O-linked Glycosylation System in Vivo," npj Vaccines, 2018, vol. 3(4), pp. 1-9, (Published online Feb. 5, 2018),doi:10.1038/s41541-017-0037-1, XP055466286.

Tan F.T.T., et al., "Sugar Coating: Bacterial Protein Glycosylation and Host-microbe Interactions," Trends in Biochemical Sciences, Jul. 2015, vol. 40, No. 7, pp. 342-350.

Van Den Dobbelsteen G.P.J.M., et al., "Immunogenicity and Safety of a Tetravalent *E. coli* O-Antigen Bioconjugate Vaccine in Animal Models," Vaccine, Elsevier, Amsterdam, NL, Jul. 6, 2016, vol. 34, No. 35, pp. 4152-4160, DOI: 10.1016/J.VACCINE.2016.06.067, ISSN: 0264-410X, XP029644969.

Vasil M.L., et al., "Molecular Studies of Pseudomonas Exotoxin A Gene," Infection and Immunity, May 1986, vol. 52, No. 2, pp. 538-548.

(56) References Cited

OTHER PUBLICATIONS

Vik et al., "Broad spectrum O-linked protein glycosylation in the human pathogen Neisseria gonorhoeae," PNAS, vol. 106, No. 11, Mar. 17, 2003, pp. 4447-4452.

Wacker M., et al., "N-linked glycosylation in Campylobacter jejuni and its functional transfer into *E. coli,*" Science, Nov. 2002, vol. 298, pp. 1790-1793, DOI: doi:10.1126/science.298.5599.1790, XP002225920.

Wacker M., et al., "Substrate Specificity of Bacterial Oligosaccharyltransferase Suggests a Common Transfer Mechanism for the Bacterial and Eukaryotic Systems," Proceedings of the National Academy of Sciences of the United States of America, May 2, 2006, vol. 103, No. 18, pp. 7088-7093.

Walker et al., "Molecular Cloning, Characterization, and Complete Nucleotide Sequences of the Gene for Pneumolysin, the Sulfhydryl-Activated Toxin of *Streptococcus pneumoniae,*" Infection and immunity, vol. 55, No. 5, May 1987, pp. 1184-1189, XP009052195.

Written Opinion for International Application No. PCT/IB2021/055361, mailed Nov. 12, 2021, 11 Pages.

U.S. Appl. No. 18/001,498, filed Dec. 12, 2022.

U.S. Appl. No. 18/001,551, filed Dec. 12, 2022.

Cohen D., et al., "Double-Blind Vaccine-Controlled Randomised Efficacy Trial of an Investigational Shigella Sonnei Conjugate Vaccine in Young Adults," The Lancet, Jan. 18, 1997, vol. 349, pp. 155-159.

Kay E., et al., "Recent Advances in the Production of Recombinant Glycoconjugate Vaccines," NPJ Vaccines, May 1, 2019, vol. 4, pp. 1-8, DOI: 10.1038/s41541-019-0110-z, XP055612407.

Taylor D.N., et al., "Synthesis, Characterization and Clinical Evaluation of Conjugate Vaccines Composed of the O-specific Polysaccharides of Shigella Dysenteriae Type 1, Shigella Flexneri Type 2a, and Shigella Sonnei (Plesiomonas Shigelloides) Bound to Bacterial Toxoids," Infection and Immunity, 1993, vol. 61, No. 9, pp. 3678-3687.

Follador R., et al., "The Diversity of Klebsiella Pneumoniae Surface Polysaccharides," Microbial Genomics, 2016, vol. 2(8)e000073, pp. 1-15.

Greenfield L.K and Whitfield C., "Synthesis of Lipopolysaccharide O-antigens by ABC Transporter-Dependent Pathways," Carbohydrate Research, 2012, vol. 356, pp. 12-24.

Hansen D.S., et al., "Klebsiella Pneumoniae Lipopolysaccharide O Typing: Revision of Prototype Strains and O-Group Distribution Among Clinical Isolates from Different Sources and Countries," Journal of clinical microbiology, 1999, vol. 37(1), pp. 56-62, Retrieved from [doi:10.1128/JCM.37.1.56-62.1999].

Szijarto V., et al., "Both Clades of the Epidemic KPC-Producing Klebsiella Pneumoniae Clone ST258 Share a Modified Galactan O-Antigen Type," International Journal of Medical Microbiology : IJMM, 2016, vol. 306(2), E-Published on 2015, pp. 89-98.

USPTO Office Action dated Jan. 15, 2026 in Co-Pending U.S. Appl. No. 18/001,551, 11 Pages.

Office Action dated Jan. 8, 2026 in Chinese Patent Application No. 202180044800.1, 11 Pages.

* cited by examiner

Figure 2D:
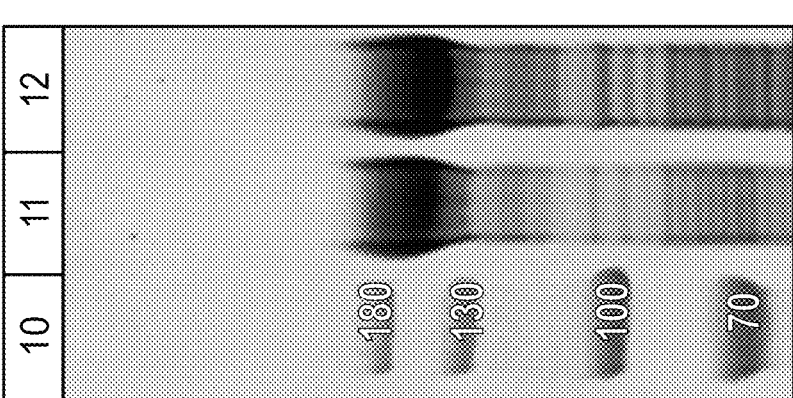

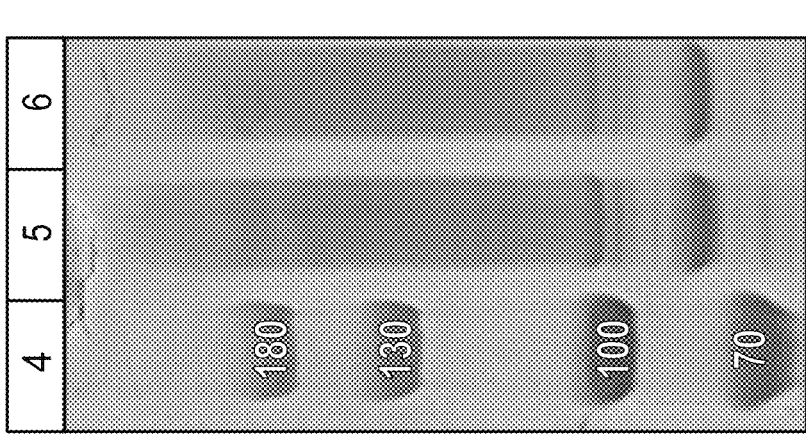
FIG. 2B
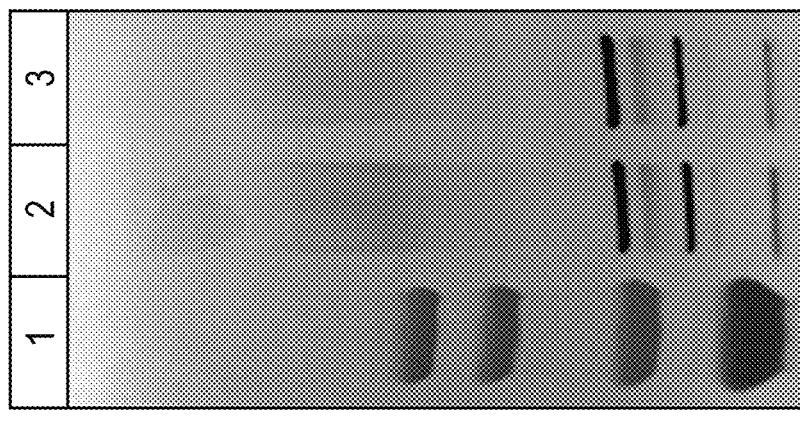
FIG. 2A
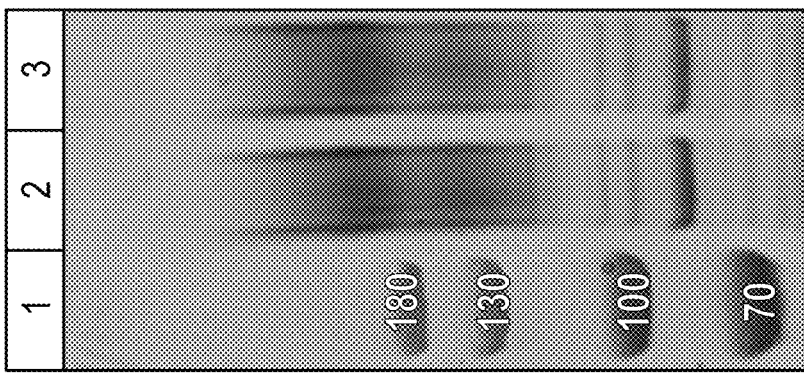

FIG. 4(contd)

Figure 6:
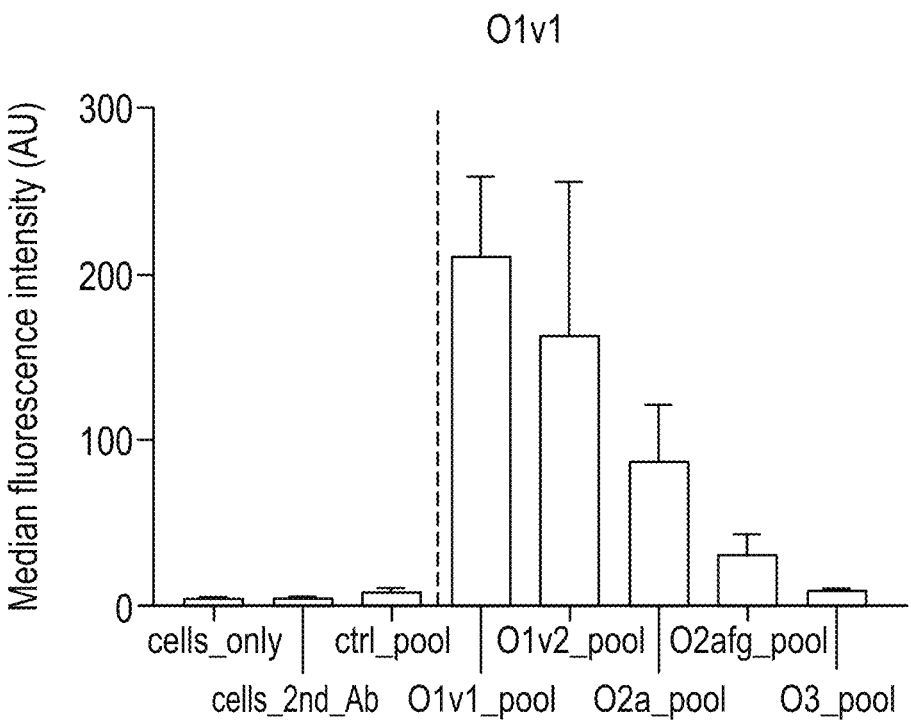
Figure 6:
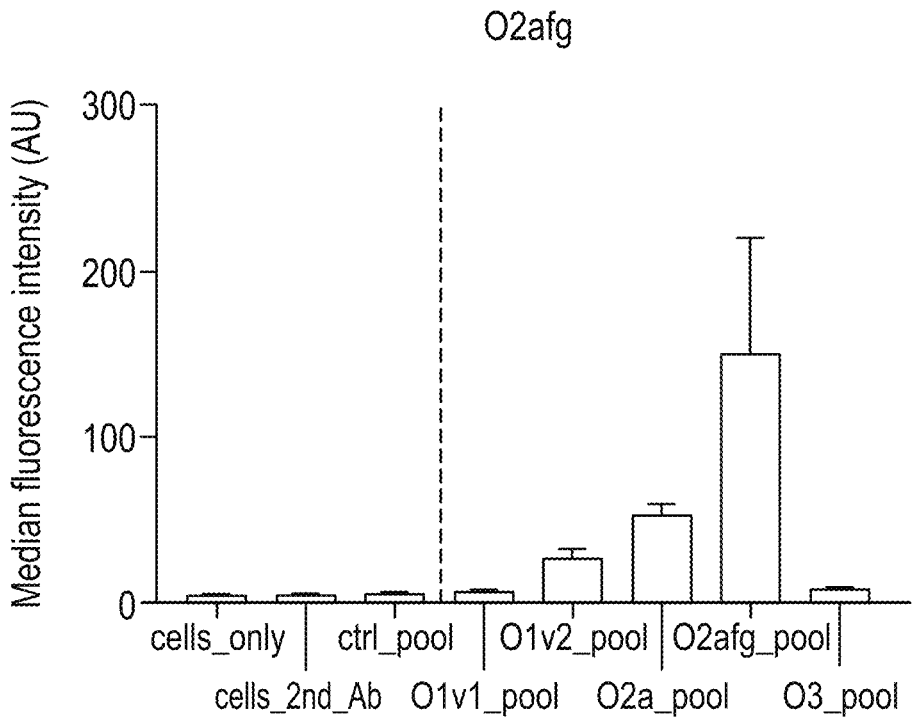

FIG. 6(contd.)
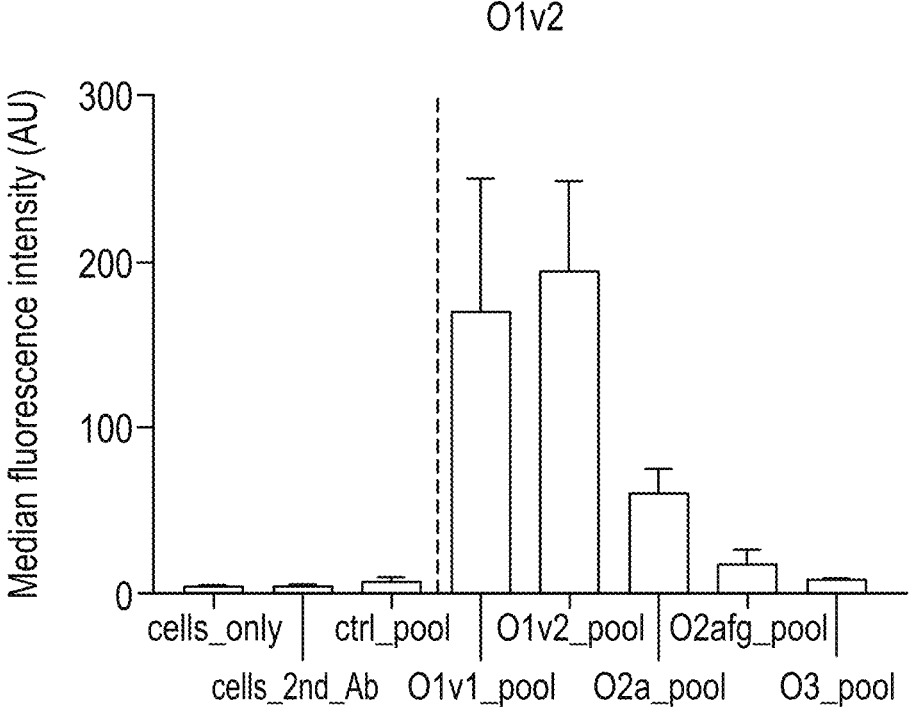
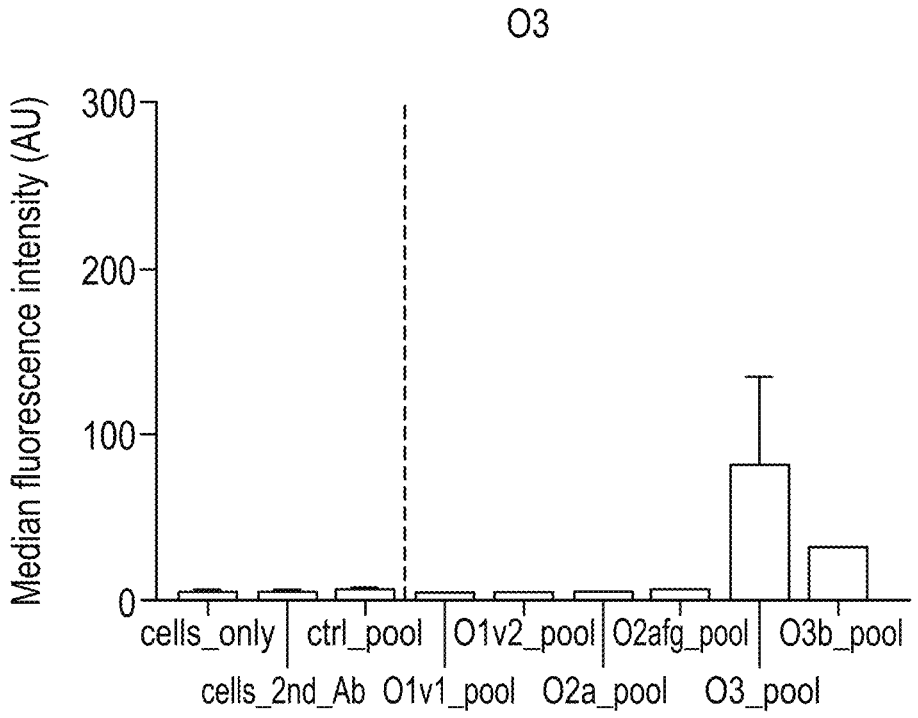

FIG. 6(contd.)
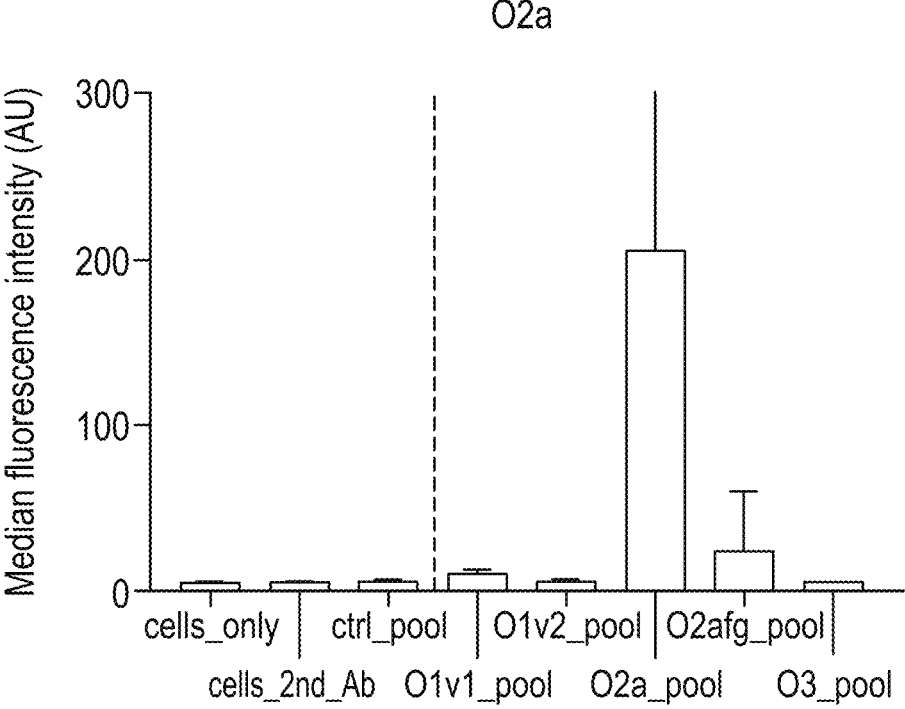
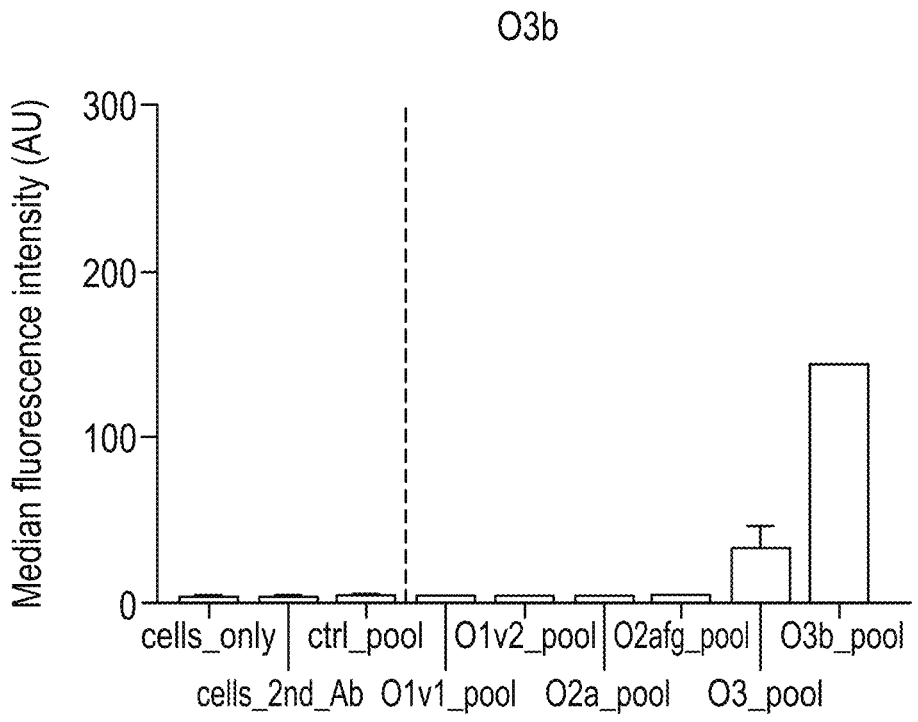

SEQUENCE LISTING

<160> NUMBER OF SEQ ID NOS: 41

<210> SEQ ID NO 1
<211> LENGTH: 5
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa can be Asp or Glu
<220> FEATURE:
<221> NAME/KEY: MISC_FEATURE
<222> LOCATION: (2)..(2)
<223> OTHER INFORMATION: Xaa can be any naturally occurring amino acid
      except proline
<220> FEATURE:
<221> NAME/KEY: MISC_FEATURE
<222> LOCATION: (4)..(4)
<223> OTHER INFORMATION: Xaa can be any naturally occurring amino acid
      except proline
<220> FEATURE:
<221> NAME/KEY: MISC_FEATURE
<222> LOCATION: (5)..(5)
<223> OTHER INFORMATION: Xaa can be Ser or Thr

<400> SEQUENCE: 1

Xaa Xaa Asn Xaa Xaa
1               5

<210> SEQ ID NO 2
<211> LENGTH: 7
<212> TYPE: PRT
<213> ORGANISM: Artificial
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be Asp or Glu
<220> FEATURE:
<221> NAME/KEY: misc_feature
<222> LOCATION: (3)..(3)
<223> OTHER INFORMATION: Xaa can be any naturally occurring amino acid
      except proline
<220> FEATURE:
<221> NAME/KEY: misc_feature
<222> LOCATION: (5)..(5)
<223> OTHER INFORMATION: Xaa can be any naturally occurring amino acid
      except proline
<220> FEATURE:
<221> NAME/KEY: misc_feature
<222> LOCATION: (6)..(6)
<223> OTHER INFORMATION: Xaa can be Ser or Thr

<400> SEQUENCE: 2

Lys Xaa Xaa Asn Xaa Xaa Lys
1               5

```
<210> SEQ ID NO 3
<211> LENGTH: 7
<212> TYPE: PRT
<213> ORGANISM: Artificial
<220> FEATURE:
<223> OTHER INFORMATION: Consensus sequence

<400> SEQUENCE: 3

Lys Asp Gln Asn Ala Thr Lys
1               5

<210> SEQ ID NO 4
<211> LENGTH: 7
<212> TYPE: PRT
<213> ORGANISM: Artificial
<220> FEATURE:
<223> OTHER INFORMATION: Concensus sequence
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa can be Asp or Glu
<220> FEATURE:
<221> NAME/KEY: MISC_FEATURE
<222> LOCATION: (3)..(3)
<223> OTHER INFORMATION: Xaa can be any naturally occurring amino acid
      except proline
<220> FEATURE:
<221> NAME/KEY: MISC_FEATURE
<222> LOCATION: (5)..(5)
<223> OTHER INFORMATION: Xaa can be any naturally occurring amino acid
      except proline
<220> FEATURE:
<221> NAME/KEY: MISC_FEATURE
<222> LOCATION: (6)..(6)
<223> OTHER INFORMATION: Xaa can be Ser or Thr
<220> FEATURE:
<221> NAME/KEY: MISC_FEATURE
<222> LOCATION: (7)..(7)
<223> OTHER INFORMATION: Xaa can be any naturally occurring amino acid

<400> SEQUENCE: 4

Xaa Xaa Xaa Asn Xaa Xaa Xaa
1               5

<210> SEQ ID NO 5
<211> LENGTH: 14
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (6)..(6)
<223> OTHER INFORMATION: Xaa can be Asp or Glu
<220> FEATURE:
<221> NAME/KEY: MISC_FEATURE
<222> LOCATION: (7)..(7)
<223> OTHER INFORMATION: Xaa can be any naturally occurring amino acid
      except proline
<220> FEATURE:
<221> NAME/KEY: MISC_FEATURE
<222> LOCATION: (9)..(9)
<223> OTHER INFORMATION: Xaa can be any naturally occurring amino acid
      except proline
<220> FEATURE:
<221> NAME/KEY: MISC_FEATURE
<222> LOCATION: (10)..(10)
<223> OTHER INFORMATION: Xaa can be Ser or Thr

<400> SEQUENCE: 5
```

```
Gly Ser Gly Gly Gly Xaa Xaa Asn Xaa Xaa Gly Ser Gly Gly
1               5               10
```

```
<210> SEQ ID NO 6
<211> LENGTH: 19
<212> TYPE: PRT
<213> ORGANISM: E. coli

<400> SEQUENCE: 6

Met Ile Lys Phe Leu Ser Ala Leu Ile Leu Leu Leu Val Thr Thr Ala
1               5                   10                  15

Ala Gln Ala
```

```
<210> SEQ ID NO 7
<211> LENGTH: 21
<212> TYPE: PRT
<213> ORGANISM: E. coli

<400> SEQUENCE: 7

Met Lys Lys Thr Ala Ile Ala Ile Ala Val Ala Leu Ala Gly Phe Ala
1               5                   10                  15

Thr Val Ala Gln Ala
            20
```

```
<210> SEQ ID NO 8
<211> LENGTH: 26
<212> TYPE: PRT
<213> ORGANISM: E. coli

<400> SEQUENCE: 8

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25
```

```
<210> SEQ ID NO 9
<211> LENGTH: 22
<212> TYPE: PRT
<213> ORGANISM: Erwinia carotovorans

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala
            20
```

```
<210> SEQ ID NO 10
<211> LENGTH: 23
<212> TYPE: PRT
<213> ORGANISM: E. coli

<400> SEQUENCE: 10

Met Ser Phe Lys Lys Ile Ile Lys Ala Phe Val Ile Met Ala Ala Leu
1               5                   10                  15

Val Ser Val Gln Ala His Ala
            20
```

```
<210> SEQ ID NO 11
<211> LENGTH: 28
<212> TYPE: PRT
<213> ORGANISM: Bacillus subtilis
```

<400> SEQUENCE: 11

Met Phe Lys Phe Lys Lys Lys Phe Leu Val Gly Leu Thr Ala Ala Phe
1               5                   10                  15

Met Ser Ile Ser Met Phe Ser Ala Thr Ala Ser Ala
            20                  25

<210> SEQ ID NO 12
<211> LENGTH: 19
<212> TYPE: PRT
<213> ORGANISM: E. coli

<400> SEQUENCE: 12

Met Lys Lys Ile Trp Leu Ala Leu Ala Gly Leu Val Leu Ala Phe Ser
1               5                   10                  15

Ala Ser Ala

<210> SEQ ID NO 13
<211> LENGTH: 21
<212> TYPE: PRT
<213> ORGANISM: E. coli

<400> SEQUENCE: 13

Met Lys Gln Ala Leu Arg Val Ala Phe Gly Phe Leu Ile Leu Trp Ala
1               5                   10                  15

Ser Val Leu His Ala
            20

<210> SEQ ID NO 14
<211> LENGTH: 26
<212> TYPE: PRT
<213> ORGANISM: Streptococcus agalactiae

<400> SEQUENCE: 14

Met Lys Met Asn Lys Lys Val Leu Leu Thr Ser Thr Met Ala Ala Ser
1               5                   10                  15

Leu Leu Ser Val Ala Ser Val Gln Ala Ser
            20                  25

<210> SEQ ID NO 15
<211> LENGTH: 713
<212> TYPE: PRT
<213> ORGANISM: Campylobacter jejuni

<400> SEQUENCE: 15

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met

-continued

```
          115              120              125

Gly Phe Val Ala Ala Leu Leu Ala Ser Ile Ala Asn Ser Tyr Tyr Asn
    130              135              140

Arg Thr Met Ser Gly Tyr Tyr Asp Thr Asp Met Leu Val Ile Val Leu
145              150              155              160

Pro Met Phe Ile Leu Phe Phe Met Val Arg Met Ile Leu Lys Lys Asp
                 165              170              175

Phe Phe Ser Leu Ile Ala Leu Pro Leu Phe Ile Gly Ile Tyr Leu Trp
                 180              185              190

Trp Tyr Pro Ser Ser Tyr Thr Leu Asn Val Ala Leu Ile Gly Leu Phe
                 195              200              205

Leu Ile Tyr Thr Leu Ile Phe His Arg Lys Glu Lys Ile Phe Tyr Ile
    210              215              220

Ala Val Ile Leu Ser Ser Leu Thr Leu Ser Asn Ile Ala Trp Phe Tyr
225              230              235              240

Gln Ser Ala Ile Ile Val Ile Leu Phe Ala Leu Phe Ala Leu Glu Gln
                 245              250              255

Lys Arg Leu Asn Phe Met Ile Ile Gly Ile Leu Gly Ser Ala Thr Leu
                 260              265              270

Ile Phe Leu Ile Leu Ser Gly Gly Val Asp Pro Ile Leu Tyr Gln Leu
                 275              280              285

Lys Phe Tyr Ile Phe Arg Ser Asp Glu Ser Ala Asn Leu Thr Gln Gly
    290              295              300

Phe Met Tyr Phe Asn Val Asn Gln Thr Ile Gln Glu Val Glu Asn Val
305              310              315              320

Asp Leu Ser Glu Phe Met Arg Arg Ile Ser Gly Ser Glu Ile Val Phe
                 325              330              335

Leu Phe Ser Leu Phe Gly Phe Val Trp Leu Leu Arg Lys His Lys Ser
                 340              345              350

Met Ile Met Ala Leu Pro Ile Leu Val Leu Gly Phe Leu Ala Leu Lys
                 355              360              365

Gly Gly Leu Arg Phe Thr Ile Tyr Ser Val Pro Val Met Ala Leu Gly
    370              375              380

Phe Gly Phe Leu Leu Ser Glu Phe Lys Ala Ile Met Val Lys Lys Tyr
385              390              395              400

Ser Gln Leu Thr Ser Asn Val Cys Ile Val Phe Ala Thr Ile Leu Thr
                 405              410              415

Leu Ala Pro Val Phe Ile His Ile Tyr Asn Tyr Lys Ala Pro Thr Val
                 420              425              430

Phe Ser Gln Asn Glu Ala Ser Leu Leu Asn Gln Leu Lys Asn Ile Ala
                 435              440              445

Asn Arg Glu Asp Tyr Val Val Thr Trp Trp Asp Tyr Gly Tyr Pro Val
    450              455              460

Arg Tyr Tyr Ser Asp Val Lys Thr Leu Val Asp Gly Gly Lys His Leu
465              470              475              480

Gly Lys Asp Asn Phe Phe Pro Ser Phe Ala Leu Ser Lys Asp Glu Gln
                 485              490              495

Ala Ala Ala Asn Met Ala Arg Leu Ser Val Glu Tyr Thr Glu Lys Ser
                 500              505              510

Phe Tyr Ala Pro Gln Asn Asp Ile Leu Lys Thr Asp Ile Leu Gln Ala
                 515              520              525

Met Met Lys Asp Tyr Asn Gln Ser Asn Val Asp Leu Phe Leu Ala Ser
    530              535              540
```

-continued

```
Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
                580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
            610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
                660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
            690                 695                 700

Asp Ala Lys Val Phe Lys Leu Lys Ile
705                 710

<210> SEQ ID NO 16
<211> LENGTH: 612
<212> TYPE: PRT
<213> ORGANISM: Pseudomonas aeruginosa

<400> SEQUENCE: 16

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
        50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
        130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
```

-continued

```
            195                 200                 205
Leu Ala Gln Gln Arg Cys Asn Leu Asp Asp Thr Trp Glu Gly Lys Ile
    210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                245                 250                 255
Ala Ala Leu Thr Ala His Gln Ala Cys His Leu Pro Leu Glu Ala Phe
                260                 265                 270
Thr Arg His Arg Gln Pro Arg Gly Trp Glu Gln Leu Glu Gln Cys Gly
                275                 280                 285
Tyr Pro Val Gln Arg Leu Val Ala Leu Tyr Leu Ala Ala Arg Leu Ser
            290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
                325                 330                 335
Arg Leu Ala Leu Thr Leu Ala Ala Ala Glu Ser Glu Arg Phe Val Arg
                340                 345                 350
Gln Gly Thr Gly Asn Asp Glu Ala Gly Ala Ala Ser Ala Asp Val Val
                355                 360                 365
Ser Leu Thr Cys Pro Val Ala Ala Gly Glu Cys Ala Gly Pro Ala Asp
            370                 375                 380
Ser Gly Asp Ala Leu Leu Glu Arg Asn Tyr Pro Thr Gly Ala Glu Phe
385                 390                 395                 400
Leu Gly Asp Gly Gly Asp Val Ser Phe Ser Thr Arg Gly Thr Gln Asn
                405                 410                 415
Trp Thr Val Glu Arg Leu Leu Gln Ala His Arg Gln Leu Glu Glu Arg
                420                 425                 430
Gly Tyr Val Phe Val Gly Tyr His Gly Thr Phe Leu Glu Ala Ala Gln
            435                 440                 445
Ser Ile Val Phe Gly Gly Val Arg Ala Arg Ser Gln Asp Leu Asp Ala
    450                 455                 460
Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
                485                 490                 495
Ala Leu Leu Arg Val Tyr Val Pro Arg Trp Ser Leu Pro Gly Phe Tyr
                500                 505                 510
Arg Thr Gly Leu Thr Leu Ala Ala Pro Glu Ala Ala Gly Glu Val Glu
                515                 520                 525
Arg Leu Ile Gly His Pro Leu Pro Leu Arg Leu Asp Ala Ile Thr Gly
    530                 535                 540
Pro Glu Glu Glu Gly Gly Arg Val Thr Ile Leu Gly Trp Pro Leu Ala
545                 550                 555                 560
Glu Arg Thr Val Val Ile Pro Ser Ala Ile Pro Thr Asp Pro Arg Asn
                565                 570                 575
Val Gly Gly Asp Leu Asp Pro Ser Ser Ile Pro Asp Lys Glu Gln Ala
                580                 585                 590
Ile Ser Ala Leu Pro Asp Tyr Ala Ser Gln Pro Gly Lys Pro Pro Arg
            595                 600                 605
Glu Asp Leu Lys
    610
```

-continued

```
<210> SEQ ID NO 17
<211> LENGTH: 647
<212> TYPE: PRT
<213> ORGANISM: Artificial
<220> FEATURE:
<223> OTHER INFORMATION: Modified EPA sequence with consensus sequences
      inserted at N-terminal+Y208+R274+A519

<400> SEQUENCE: 17

Gly Ser Gly Gly Gly Asp Gln Asn Ala Thr Gly Ser Gly Gly Gly Lys
1               5                   10                  15

Leu Ala Glu Glu Ala Phe Asp Leu Trp Asn Glu Cys Ala Lys Ala Cys
            20                  25                  30

Val Leu Asp Leu Lys Asp Gly Val Arg Ser Ser Arg Met Ser Val Asp
        35                  40                  45

Pro Ala Ile Ala Asp Thr Asn Gly Gln Gly Val Leu His Tyr Ser Met
    50                  55                  60

Val Leu Glu Gly Gly Asn Asp Ala Leu Lys Leu Ala Ile Asp Asn Ala
65                  70                  75                  80

Leu Ser Ile Thr Ser Asp Gly Leu Thr Ile Arg Leu Glu Gly Gly Val
                85                  90                  95

Glu Pro Asn Lys Pro Val Arg Tyr Ser Tyr Thr Arg Gln Ala Arg Gly
            100                 105                 110

Ser Trp Ser Leu Asn Trp Leu Val Pro Ile Gly His Glu Lys Pro Ser
            115                 120                 125

Asn Ile Lys Val Phe Ile His Glu Leu Asn Ala Gly Asn Gln Leu Ser
    130                 135                 140

His Met Ser Pro Ile Tyr Thr Ile Glu Met Gly Asp Glu Leu Leu Ala
145                 150                 155                 160

Lys Leu Ala Arg Asp Ala Thr Phe Phe Val Arg Ala His Glu Ser Asn
                165                 170                 175

Glu Met Gln Pro Thr Leu Ala Ile Ser His Ala Gly Val Ser Val Val
            180                 185                 190

Met Ala Gln Ala Gln Pro Arg Arg Glu Lys Arg Trp Ser Glu Trp Ala
            195                 200                 205

Ser Gly Lys Val Leu Cys Leu Leu Asp Pro Leu Asp Gly Val Tyr Asn
    210                 215                 220

Lys Asp Gln Asn Ala Thr Lys Leu Ala Gln Gln Arg Cys Asn Leu Asp
225                 230                 235                 240

Asp Thr Trp Glu Gly Lys Ile Tyr Arg Val Leu Ala Gly Asn Pro Ala
            245                 250                 255

Lys His Asp Leu Asp Ile Lys Pro Thr Val Ile Ser His Arg Leu His
            260                 265                 270

Phe Pro Glu Gly Gly Ser Leu Ala Ala Leu Thr Ala His Gln Ala Cys
    275                 280                 285

His Leu Pro Leu Glu Ala Phe Thr Lys Asp Gln Asn Ala Thr Lys His
    290                 295                 300

Arg Gln Pro Arg Gly Trp Glu Gln Leu Glu Gln Cys Gly Tyr Pro Val
305                 310                 315                 320

Gln Arg Leu Val Ala Leu Tyr Leu Ala Ala Arg Leu Ser Trp Asn Gln
            325                 330                 335

Val Asp Gln Val Ile Arg Asn Ala Leu Ala Ser Pro Gly Ser Gly Gly
            340                 345                 350

Asp Leu Gly Glu Ala Ile Arg Glu Gln Pro Glu Gln Ala Arg Leu Ala
```

```
                355               360               365

Leu Thr Leu Ala Ala Ala Glu Ser Glu Arg Phe Val Arg Gln Gly Thr
        370               375               380

Gly Asn Asp Glu Ala Gly Ala Ala Ser Ala Asp Val Val Ser Leu Thr
385               390               395               400

Cys Pro Val Ala Ala Gly Glu Cys Ala Gly Pro Ala Asp Ser Gly Asp
                405               410               415

Ala Leu Leu Glu Arg Asn Tyr Pro Thr Gly Ala Glu Phe Leu Gly Asp
                420               425               430

Gly Gly Asp Val Ser Phe Ser Thr Arg Gly Thr Gln Asn Trp Thr Val
                435               440               445

Glu Arg Leu Leu Gln Ala His Arg Gln Leu Glu Glu Arg Gly Tyr Val
                450               455               460

Phe Val Gly Tyr His Gly Thr Phe Leu Glu Ala Ala Gln Ser Ile Val
465               470               475               480

Phe Gly Gly Val Arg Ala Arg Ser Gln Asp Leu Asp Ala Ile Trp Arg
                485               490               495

Gly Phe Tyr Ile Ala Gly Asp Pro Ala Leu Ala Tyr Gly Tyr Ala Gln
                500               505               510

Asp Gln Glu Pro Asp Ala Arg Gly Arg Ile Arg Asn Gly Ala Leu Leu
                515               520               525

Arg Val Tyr Val Pro Arg Trp Ser Leu Pro Gly Phe Tyr Arg Thr Gly
        530               535               540

Leu Thr Leu Lys Asp Gln Asn Ala Thr Lys Ala Pro Glu Ala Ala Gly
545               550               555               560

Glu Val Glu Arg Leu Ile Gly His Pro Leu Pro Leu Arg Leu Asp Ala
                565               570               575

Ile Thr Gly Pro Glu Glu Glu Gly Gly Arg Val Thr Ile Leu Gly Trp
                580               585               590

Pro Leu Ala Glu Arg Thr Val Val Ile Pro Ser Ala Ile Pro Thr Asp
        595               600               605

Pro Arg Asn Val Gly Gly Asp Leu Asp Pro Ser Ser Ile Pro Asp Lys
        610               615               620

Glu Gln Ala Ile Ser Ala Leu Pro Asp Tyr Ala Ser Gln Pro Gly Lys
625               630               635               640

Pro Pro Arg Glu Asp Leu Lys
                645
```

```
<210> SEQ ID NO 18
<211> LENGTH: 666
<212> TYPE: PRT
<213> ORGANISM: Artificial
<220> FEATURE:
<223> OTHER INFORMATION: Modified EPA sequence with consensus sequences
      inserted at N-terminal+Y208+R274+A519 and E. coli DsbA signal
      sequence

<400> SEQUENCE: 18

Met Lys Lys Ile Trp Leu Ala Leu Ala Gly Leu Val Leu Ala Phe Ser
1               5               10               15

Ala Ser Ala Gly Ser Gly Gly Gly Asp Gln Asn Ala Thr Gly Ser Gly
                20               25               30

Gly Gly Lys Leu Ala Glu Glu Ala Phe Asp Leu Trp Asn Glu Cys Ala
        35               40               45

Lys Ala Cys Val Leu Asp Leu Lys Asp Gly Val Arg Ser Ser Arg Met
        50               55               60
```

Ser Val Asp Pro Ala Ile Ala Asp Thr Asn Gly Gln Gly Val Leu His
65                  70                  75                  80

Tyr Ser Met Val Leu Glu Gly Gly Asn Asp Ala Leu Lys Leu Ala Ile
                85                  90                  95

Asp Asn Ala Leu Ser Ile Thr Ser Asp Gly Leu Thr Ile Arg Leu Glu
            100                 105                 110

Gly Gly Val Glu Pro Asn Lys Pro Val Arg Tyr Ser Tyr Thr Arg Gln
            115                 120                 125

Ala Arg Gly Ser Trp Ser Leu Asn Trp Leu Val Pro Ile Gly His Glu
        130                 135                 140

Lys Pro Ser Asn Ile Lys Val Phe Ile His Glu Leu Asn Ala Gly Asn
145                 150                 155                 160

Gln Leu Ser His Met Ser Pro Ile Tyr Thr Ile Glu Met Gly Asp Glu
                165                 170                 175

Leu Leu Ala Lys Leu Ala Arg Asp Ala Thr Phe Phe Val Arg Ala His
            180                 185                 190

Glu Ser Asn Glu Met Gln Pro Thr Leu Ala Ile Ser His Ala Gly Val
        195                 200                 205

Ser Val Val Met Ala Gln Ala Gln Pro Arg Arg Glu Lys Arg Trp Ser
    210                 215                 220

Glu Trp Ala Ser Gly Lys Val Leu Cys Leu Leu Asp Pro Leu Asp Gly
225                 230                 235                 240

Val Tyr Asn Lys Asp Gln Asn Ala Thr Lys Leu Ala Gln Gln Arg Cys
                245                 250                 255

Asn Leu Asp Asp Thr Trp Glu Gly Lys Ile Tyr Arg Val Leu Ala Gly
            260                 265                 270

Asn Pro Ala Lys His Asp Leu Asp Ile Lys Pro Thr Val Ile Ser His
            275                 280                 285

Arg Leu His Phe Pro Glu Gly Gly Ser Leu Ala Ala Leu Thr Ala His
    290                 295                 300

Gln Ala Cys His Leu Pro Leu Glu Ala Phe Thr Lys Asp Gln Asn Ala
305                 310                 315                 320

Thr Lys His Arg Gln Pro Arg Gly Trp Glu Gln Leu Glu Gln Cys Gly
                325                 330                 335

Tyr Pro Val Gln Arg Leu Val Ala Leu Tyr Leu Ala Ala Arg Leu Ser
            340                 345                 350

Trp Asn Gln Val Asp Gln Val Ile Arg Asn Ala Leu Ala Ser Pro Gly
            355                 360                 365

Ser Gly Gly Asp Leu Gly Glu Ala Ile Arg Glu Gln Pro Glu Gln Ala
    370                 375                 380

Arg Leu Ala Leu Thr Leu Ala Ala Ala Glu Ser Glu Arg Phe Val Arg
385                 390                 395                 400

Gln Gly Thr Gly Asn Asp Glu Ala Gly Ala Ala Ser Ala Asp Val Val
                405                 410                 415

Ser Leu Thr Cys Pro Val Ala Ala Gly Glu Cys Ala Gly Pro Ala Asp
                420                 425                 430

Ser Gly Asp Ala Leu Leu Glu Arg Asn Tyr Pro Thr Gly Ala Glu Phe
            435                 440                 445

Leu Gly Asp Gly Gly Asp Val Ser Phe Ser Thr Arg Gly Thr Gln Asn
    450                 455                 460

Trp Thr Val Glu Arg Leu Leu Gln Ala His Arg Gln Leu Glu Glu Arg
465                 470                 475                 480

```
Gly Tyr Val Phe Val Gly Tyr His Gly Thr Phe Leu Glu Ala Ala Gln
            485                 490                 495

Ser Ile Val Phe Gly Gly Val Arg Ala Arg Ser Gln Asp Leu Asp Ala
            500                 505                 510

Ile Trp Arg Gly Phe Tyr Ile Ala Gly Asp Pro Ala Leu Ala Tyr Gly
            515                 520                 525

Tyr Ala Gln Asp Gln Glu Pro Asp Ala Arg Gly Arg Ile Arg Asn Gly
        530                 535                 540

Ala Leu Leu Arg Val Tyr Val Pro Arg Trp Ser Leu Pro Gly Phe Tyr
545                 550                 555                 560

Arg Thr Gly Leu Thr Leu Lys Asp Gln Asn Ala Thr Lys Ala Pro Glu
            565                 570                 575

Ala Ala Gly Glu Val Glu Arg Leu Ile Gly His Pro Leu Pro Leu Arg
            580                 585                 590

Leu Asp Ala Ile Thr Gly Pro Glu Glu Gly Gly Arg Val Thr Ile
            595                 600                 605

Leu Gly Trp Pro Leu Ala Glu Arg Thr Val Val Ile Pro Ser Ala Ile
            610                 615                 620

Pro Thr Asp Pro Arg Asn Val Gly Gly Asp Leu Asp Pro Ser Ser Ile
625                 630                 635                 640

Pro Asp Lys Glu Gln Ala Ile Ser Ala Leu Pro Asp Tyr Ala Ser Gln
            645                 650                 655

Pro Gly Lys Pro Pro Arg Glu Asp Leu Lys
            660                 665
```

<210> SEQ ID NO 19
<211> LENGTH: 30
<212> TYPE: DNA
<213> ORGANISM: Artificial
<220> FEATURE:
<223> OTHER INFORMATION: Forward primer

<400> SEQUENCE: 19
aagctagcgc cgccgaggaa gccttcgacc                                           30

<210> SEQ ID NO 20
<211> LENGTH: 50
<212> TYPE: DNA
<213> ORGANISM: Artificial
<220> FEATURE:
<223> OTHER INFORMATION: Reverse primer

<400> SEQUENCE: 20
aagaattctc agtggtggtg gtggtggtgc ttcaggtcct cgcgcggcgg                     50

<210> SEQ ID NO 21
<211> LENGTH: 768
<212> TYPE: DNA
<213> ORGANISM: Klebsiella pneumoniae

<400> SEQUENCE: 21
atgaagtaca atttagggta tttatttgat ttacttgttg tcataacaaa taaagatcta         60
aaagtgcgct ataagagcag catgctaggc tatttatggt cagtagcaaa tccattgctt        120
tttgccatga tttattattt tatatttaag ctggtaatga gagtacaaat tccaaattat        180
accgttttcc tcattaccgg cttgtttccg tggcaatggt ttgccagttc ggccactaac        240
tcattatttt cattcatcgc taacgctcaa attatcaaga agacagtttt tccccggtcc        300
gtgattccgc taagtaatgt aatgatggaa gggttgcatt ttctttgtac catcccggtt        360
```

-continued

```
attgttgtct ttcttttttgt ttatggcatg acgccgtcct tgtcctgggt ttggggtata      420
cctctcattg ctattggcca ggtgattttc acctttggtg tttcaatcat cttttcaacg      480
ctgaacctgt ttttccgtga cctggagcgc tttgtcagtc tggggattat gctgatgttt      540
tattgtacgc cgattttata tgcgtctgat atgattccgg aaaaatttag ctggataatt      600
acctacaatc cgctagcgag tatgattctt agttggcgtg atttattcat gaatgggact      660
cttaattatg agtatatttc tatactctat tttacgggaa tcattttgac ggttgtcggt      720
ttgtctattt tcaataaatt aaaatatcga tttgcagaga tcttgtaa                    768
```

<210> SEQ ID NO 22
<211> LENGTH: 741
<212> TYPE: DNA
<213> ORGANISM: Klebsiella pneumoniae

<400> SEQUENCE: 22

```
atgcacccag ttattaactt cagtcatgtt acaaaagagt atcctctgta ccatcatatt       60
ggctcaggaa tcaaagattt aattttccat ccgaaacgcg cttttcaatt gctgaagggg      120
cggaaatatt tagctatcga agacgtatcc tttacagttg gcaaaggtga ggctgttgct      180
ctgattggac gtaatggggc aggaaagagt acctctcttg gcctggttgc cggcgtgatt      240
aagccaacta agggaaccgt caccactgaa ggacgggtgg catcgatgct tgaactcggc      300
ggaggctttc atccggaact taccgggcgt gagaatattt acctgaatgc tactctgctg      360
ggccttcggc gtaaagaggt ccagcaacgt atggaacgta ttattgaatt ttcggaactg      420
ggagaattca tagacgagcc aatcagagtg tactcaagcg gaatgctagc taagttaggt      480
ttttcggtca tcagtcaggt tgaaccggat atttttaatta ttgatgaagt tctggcagta      540
ggtgatatcg cttttcaggc aaaatgtatt cagaccataa gagatttttaa gaaaagaggc      600 gtgacaatat tgtttgttag ccacaatatg agtgacgttg aaaaaatctg cgacagagtc      660
atctggatcg aaaatcatag gctcagagaa gtggggtctg cagagcgaat cattgaactg      720
tacaagcaag caatggctta a                                                 741
```

<210> SEQ ID NO 23
<211> LENGTH: 1896
<212> TYPE: DNA
<213> ORGANISM: Klebsiella pneumoniae

<400> SEQUENCE: 23

```
atgaacaata gcgttaaaat ctataccagc caccataagc ctagtgcttt tcttaatgct       60
gcaattatca aacctctgca tgtcggcaaa gctaattctt gtaatgaaat tggttgtcca      120
ggagatgaca ctggcgataa tatttccttt aagaatccgt tttattgcga acttactgcg      180
cattattggg tttggaaaaa cgaagagctg gcagactatg tcggtttcat gcactatcgc      240
cgtcatctta attttttccga aaaacaaact ttttctgagg atacgtgggg ggtcgtgaac      300
catccatgca ttgatgaaga atatgaggag atctttggat taaacgaaga aacaattcaa      360
cggtgtgtcg aaggtattga catcttgctg cccaaaaaat ggtctgtcac tgcggcggga      420
agtaaaaata attacgatca ctatgaacga ggtgaatact acacattcg tgattatcag      480 gctgccattg ccaccgttga aaaactatat ccagagtata gcacggcaat aaaaacgttt      540
aatgatgcca gtgatggcta ttacacaaat atgtttgtca tgcgcaaaga tattttttgtt      600 aactattctg agtggctctt ttctattctg gataatctcg aagatgccat ctcgatgaac      660
```

-continued

```
aattataatg ctcaggaaaa acgcgttatt gggcatatag cagaacggct gtttaatatt      720
tacattatta agttgcaaca agatggtgag cttaaggtaa aagaattaca gcgtactttt      780
gtcagcaatg aaacattcaa tggtgcactg aatccagttt ttgattctgc ggttccagtg      840
gttatcagtt tcgatgataa ttacgcagtc agcggtggtg cattaattaa ttccattgtc      900
cggcatgcgg ataaaaataa aaattatgat atcgtcgtgc tcgaaaacaa agtaagctat      960
ttgaataaaa cgcggttagt aaatctaacc tcggctcatc cgaatatttc tcttcgtttt     1020
tttgacgtta atgccttcac tgaaataaac ggtgtgcata cccgagcgca ttttagcgca     1080
tcaacgtatg cccgtctttt tattcctcaa ctgttcagac gatacgataa agtcgtattt     1140
attgattcgg ataccgttgt aaaggctgac ctgggtgaac tgcttgatgt ccctctgggc     1200
aacaatttag ttgcagcggt taaggatatc gtcatggaag gttttgtaaa attttctgca     1260
atgtcggcat cagatgatgg cgttatgccg gcaggcgaat atttacagaa aaccttaaat     1320
atgaataacc ctgatgaata ttttcaggca gggattattg tttttaatgt caaacaaatg     1380
gtcgaagaaa atacttttgc tgaattgatg cgggtattaa aggcaaaaaa atactggttc     1440
ctcgaccagg atatcatgaa taaagtattc tactctcgag tcacatttct gccattagag     1500
tggaacgttt atcatggtaa tggcaacacg gatgatttct tccctaatct taagtttgca     1560
acgtatatga aattttttagc agctcgcaag aagcctaaaa tgattcatta tgcgggtgag     1620
aacaaaccat ggaataccga aaaagtcgat ttttatgacg actttattga aaacatcgct     1680
aacactccat gggagatgga aatctataaa cgtcagatgt cgttagcggc ttcgattggt     1740
ttaacccata gcgagccgca acaacaaatc ttgttccaga ccaaaatcaa gaacgtactg     1800
atgccttatg ttaataaata tgcaccaata ggcacgccaa gaagaaacat gatgactaaa     1860
tattattaca aagtacgccg tgctattctt ggataa                               1896
```

<210> SEQ ID NO 24
<211> LENGTH: 1155
<212> TYPE: DNA
<213> ORGANISM: Klebsiella pneumoniae

<400> SEQUENCE: 24

```
atgaaaagaa aaaaaatatt gatcgtaggc gctggcttct ctggtgcagt tatcggtcgc       60
caacttgctg agaagggaca tcaagtccat attatcgatc agcgtgatca tattgggggg      120
aattcttatg atgcacgcga ctctgaaacg aatgtgatgg tacatgttta tggacccccat     180 attttccata ctgacaatga atcagtgtgg aactatgtca acaagcatgc agagatgatg      240
ccctatgtga accgggttaa agcgacagtt aatggtcagg tattttccct gcctattaat      300
ttgcatacta tcaatcagtt tttctcaaaa acttgttcgc ctgatgaggc cagagcgctc      360
attgctgaga aaggggacag cactattgct gatccacaaa cttttgaaga gcaagcgtta      420
cgctttattg gtaaagagtt atatgaggcc tttttttaaag gatatacgat taaacagtgg      480
gggatgcaac cctcggaact gcccgcatct attcttaaac gtcttcctgt tcgtttttaac      540 tatgacgata ttattttttaa ccacaaattt cagggcatgc cgaaatgtgg ttatacgcag      600
atgattaagt caattcttaa gcatgagaat atcaaggttg acttacagcg ggaatttatc      660
gttgacgagc gaactcatta cgatcacgta ttctatagcg gtccattaga tgcgtttttat      720 ggctaccaat atggccgtct gggctatcga acattagatt ttaaaaagtt tatctatcag      780
ggtgattacc agggatgcgc agtgatgaac tattgttctg tggatgtgcc ctatactcgc      840
atcactgaac ataaaatattt ttctccctgg gaacaacacg acggctctgt ttgttataaa      900
```

```
gagtatagcc gtgcttgtga agaaaatgat attccttact atcctattcg ccagatggga      960
gagatggctc ttcttgaaaa atatttgtca ttggccgaga atgaaaccaa catcactttt     1020
gtcggtcgtc ttggaaccta ccgttacctt gatatggatg tgaccatcgc cgaagcattg     1080
aaaacggcag aagtctattt aaattcactc actgaaaatc agccaatgcc tgtgtttacg     1140
gtttctgtac gatga                                                      1155

<210> SEQ ID NO 25
<211> LENGTH: 894
<212> TYPE: DNA
<213> ORGANISM: Klebsiella pneumoniae

<400> SEQUENCE: 25
atgaaatata cggcattgat agtgacattc aatcgtctcg gcaaactgaa aaaaacggtt       60
gaagagaccc tcaaacttga attcactaat attgttattg tcaataacgg gtccacggat      120
gggacccaag cctggctttc gtcaattgtt gatacacgag tcattgtatt aaccctcacc      180
gagaataccg gtggggcggg gggctttaaa accggtagtc agtatatctg tgaacagctg      240
gcaagtgatt gggtattttt ctacgatgac gatgcttacc cctatccaga cacgttgaag      300
tcctttttac agctggataa gcagggatgt cgggtattta gtggactggt gaaagatccg      360
caaggaaaac cgtgtccgat gaatatgccg ttctcgcgtg tgccaacttc ccttggcgac      420
actgtacgct atttacgcta ccctgcagag tttatcccgg cagctaatcg ttctatgttc      480
gtacaaacgg tttcatttgt tgggatggtc atacatcgtg atctgctcgc gaccagtctt      540
gaccacatcc atgaacagct ctttatctac tttgatgatc tttactttgg ctatcagcta      600
tcattagctg gtgagcaaat tatgtatagc ccggagttgc tttttttatca tgatgtgagt      660 attcagggca aacttattgc ccctgaatgg aaggtttact atctatgccg taatttgatc      720
ctgtcgaaga aaatattcca gaaaaatgcc gtatatagca attcagcgat agcgatacgc      780
atcctaaaat atatattaat cctgccatgg caacgtcaaa aatattccta tatgaaattt      840
attcttcgtg gaatttcaca tggcataaaa ggtattagtg gtaagtatca ttaa           894

<210> SEQ ID NO 26
<211> LENGTH: 1131
<212> TYPE: DNA
<213> ORGANISM: Klebsiella pneumoniae

<400> SEQUENCE: 26
atgagaaaat tgtgttattt cataaattcg gattggtact tcgatttaca ctggatcgat       60
cgtgccatcg cctcccgtga tgcaggttat gagattcaca tcatcagcca ttttattgat      120
gacaacataa taaataaatt taaaacattt ggctttattt gccataatgt tactcttgat      180
gctcaatctt ttaatgcatt agttttcttt cgtacttacc atgatgtgca aaaaattatt      240
aaaaatataa aaccggatct cttgcattgc atcactatca agccatgttt gattggtggt      300
gtgctcgcga agaaatttaa tctgccggtc atcgtaagtt ttgttgggct tggaagagta      360
ttttcttctg acagcatgcc tttaaaatta ttgcggcagt ttactattgc tgcatataaa      420
tatattgcca gtaataagcg ctgtatattt atgtttgaac atgaccgcga cagaaaaaaa      480
ctggctaagt tggttggact cgaagaacaa cagactattg ttattgatgg tgcaggcatt      540
aatccagaga tatacaaata ttctcttgaa caggatcacg atgtccctgt tgtattgttt      600
gccagccgta tgttgtggag taaaggactg ggcgacttaa ttgaagcgaa gaaaatatta      660
```

```
cgcagtaaga atattcactt tactttgaat gttgctggaa ttctggtcga aaatgataaa      720
gatgcaattt cccttcaggt cattgaaaat tggcatcagc aaggattaat taactggtta      780
ggtcgttcga ataacgtttg cgatcttatt gagcaatcaa atatcgttgc tttgccgtca      840
gtttattctg aaggtgttcc gcgaattctt ctggaagcat cttctgtggg gcgcgcttgt      900
attgcttatg atgttggtgg ttgtgatagc cttattattg ataacgataa tggaattatt      960
gttaaaagca attcacctga agagctggct gataaacttg ccttttttgct tagcaatcct     1020 aaagcacgcg ttgaaatggg tattaagggg aggaaacgta tacaagataa attttctagt     1080
gttatgatta tcgataaaac attgcaaata tatcatgatg tagttcgatg a             1131

<210> SEQ ID NO 27
<211> LENGTH: 378
<212> TYPE: DNA
<213> ORGANISM: Klebsiella pneumoniae

<400> SEQUENCE: 27
atgccaagtt caggcccatt atggcaacta atgaaatatg ggttagttgg gatagtcaat       60
acactaatta cggcagttgt aattttcctg ctaatgcatt tgggtcttgg catttatctg      120
tccaatgcga tgggttatgt tgtaggtatt gttttcagct ttatagcaaa cacaatattt      180
acatttacgc aaccaatcag tatcaataga ctaataaaat ttttatgtgt ttgcttcatt      240
tgttatgtgg caaatatcat tgtcataaaa atattttttcg tttttatgcc agaaaaaata      300
tattcagcac aaatccttgg gatgttcaca tacactatca caggttttat tttaaacaag      360
ttctgggcga tgaaatga                                                   378

<210> SEQ ID NO 28
<211> LENGTH: 981
<212> TYPE: DNA
<213> ORGANISM: Klebsiella pneumoniae

<400> SEQUENCE: 28
atgacaacct caactgatat aaaaagcact ccttctttag ctattgtggt accttgctat       60
aatgaacaag aggcttttcc tttctgtctc gaaaagcttt cgaatgtact aaattcattg      120
atagccagaa ataaaattaa taacaatagt tatctttttgt ttgtcgatga tggtagtcgt      180
gacaatactt gggcacaaat taaagatgcc tcgaccgctt atcactatgt gcgaggaata      240
aaattatcaa gaaataaagg acatcaaatt gcgttgatgg cagggttacg ctcggtcgat      300
acagacgtaa gcattagcat cgatgcggat ctacaagacg atgtaaattg catcgaaaaa      360
atgattgacg cttacagcca gggatatgac atagtatacg gcgtaagagg taatcgagac      420
agtgacacgt tttttaaacg tacaacagct aatgcatttt acgcaataat gtcccacttg      480
ggagtaaatc aaactccaaa tcatgcagat tatcgattat taagtaatcg agcattggag      540
gctcttaaac aatataaaga gcaaatatat tatttacgtg gattagtgcc tcttgtggga      600 taccctcga tcgaggtgca atatagccgt gaagaaagaa ttgcaggtga atcaaaatat      660
ccaattaaaa aaatgcttgc gctggctctc gagggaatta cctcattatc agttacaccg      720
ttacgaatta tagctatgac aggttttata acttgcatca tatcaaccat cgctgcgatt      780
tatgctttaa ttcaaaaaac aacaggtact acagttgagg gatggacatc agtcatgatc      840
gctatattct ttcttggcgg cgtgcaaatg ctttctttag gtattatagg agaatatgtc      900
ggaaaaattt atatagagac gaaaaataga cctaaatatt tcattgacga aagcgtaggt      960
aatgatagca atggaaaata a                                              981
```

-continued

```
<210> SEQ ID NO 29
<211> LENGTH: 1461
<212> TYPE: DNA
<213> ORGANISM: Klebsiella pneumoniae

<400> SEQUENCE: 29
atgcaaaatc tgatcaatcc tttagcagag ggaaataaaa aaaacgttta cattttttat      60 ttcttttgc ttatgttaac attttcaccg gtaattttct tttcatatgc attttcagac      120
gactggtcaa cactctttga tgctataaca agaaacggct cttcgtttca gtgggatgtc      180
caatctggtc gtcccgttta tgctgtgttc cgttactatg gaaaaatgtt aattaatgat      240
atttcttcat tttcgtattt gcggcttttt aatatattaa gtcttgttgt cttaagttgt      300
tttatttaca acttcataga cagcagaaaa atatttgata accccgtatt caaaataaca      360
tttccgctgt taatttgctt actccctgcg tttcaagttt atgcttcatg ggcaacatgt      420
ttcccgttca ctatttcagt attgctggca ggtattagtt ataataaatg tttcccacat      480
tcgaagcagc ggtcgtcatt gtcagaaaaa ttagcatcca ttgttgtctt atgggtggca      540
tttgcaatat atcaaccgac agcaattaca ttcttattct tttttatgct tgatagttgt      600
ataaaaaaag aaagtagttt aactgtgaaa aaagttgcga catgttttat cattttagtt      660
atcggtgttg caggcagttt tataatgtca aaagtacttc ctgtctggct atatggggaa      720
tcattatcga gagccgagtt aaccgcagat atcggtggaa agatgaaatg gttcataaat      780
gaatcactaa taaacgctgt aaataactat aacatacaac cagtaaaaat atattcttgg      840
ttctcctcgc ttgcaatttt aatcggctta tacactattt ttgtgggaaa atcaggcaga      900
tggaaaacgt tcatagtcat agcgatcggg ataggttcct acgctccaaa tttagcgaca      960
aaagagaatt gggcagcatt ccgctcgtta gtggccttag aacttattat atcaactcta      1020
tttcttattg gcataaatag ccttgtcagt agaattttta agcaagcatt tgtctggcct      1080
cttatcgctt aacaattat gataatagct cagtataata ttataaatgg atttattatt      1140
cctcaacgct ctgaaattca ggcacttgct gcggaaataa ctaataaaat acctaagaat      1200
tacacaggaa aattaatgtt cgatctcaca gatcccgctt acaatgcctt tacaaaaaca      1260
cagagatatg atgaatttgg gaatatttca ttagcagcac cctgggcgct caaaggtatg      1320
gctgaagaga tcagaattat gaaaggattt aatttcaaac tatctaacaa cgttatagtt      1380
tctgagacca tcgatgtat tgatgattgt atggttatca aaacgtcaga tgcaatgcga      1440
aggtcaacga taaattatta g      1461

<210> SEQ ID NO 30
<211> LENGTH: 2223
<212> TYPE: DNA
<213> ORGANISM: Klebsiella pneumoniae

<400> SEQUENCE: 30
atgaagaaaa ttcttataat gacgccggac attgaggggc ctgtccgtaa cggcggtatt      60
ggtactgctt tcactgccct tgccactact ttggcaaaaa aggggtatga tgttgatgta      120
ttgtatacat gtggcgacta ttctgaatca tctgtatcga aatttagcga ctggtcacgt      180
atttatagta cctttggtat caatctgcta agaaccggac tgataaaaga gattaatatt      240
gatgcaccgt attttagaag gaaaagttat tcaatttatc tctggttgaa agaaaataac      300
acctatgaca ctgttatttc ttgtgagtgg caggcagatc tttattacac tttattaagc      360
```

```
aaaaagaatg gaacggattt tgaaaataca aagttcattg taaatactca cagttcaacg      420
ttatgggctg atgaaggtaa ttaccagctt ccatatgatc agaaccatct tgaactctat      480
tatatggaga aaatggtggt tgaaatggcg gatgaagttg ttagtccgtc tcagtattta      540
attgattgga tgttgagtaa gcactggaat gttcctgaag aacgtcatgt aattttaaat      600
tgcgagccat ttcaagggtt tgtgacgaga gatgatgtta cagttaaaat aaatgaaaag      660
ccagcttctg gcgttgagct tgtattttttc ggccgccttg aaacccgtaa aggacttgac      720
atattcctgc gtgcattaag aaaactatct gatgaagata aagagagcat ttctggagta      780
accttcctcg aaaaaatgt cactatgggg aaaactgatt catttactta tattatgaat      840
cagactaaaa atttgggact cgcagttaat gtcatcagcg actatgatcg taccaacgct      900
aatgaatata taaaaagaaa aaatgtatta gtcatcattc catcacttgt agaaaactca      960
ccctatactg tttatgaatg tttgattaat aacgttaatt ttctcgcttc aaacgttggt     1020
ggaattccag agcttattcc gcaggagcat catgcggaag ttctatttat tcctacacct     1080
gccgatttat acgaaaaat ccactatcgc ttaaaaaata taaatataaa accagggctt     1140
gctgaatcac aagacaatat taaagaagct tggtttgtcg cagttgaacg aaaaaacaac     1200
cgcacattca agaaatcga tgaagctaac agcccgttag ttagcgtgtg tataactcac     1260
ttcgaacgtc accatttgct tcagcaagca ctcgcatcaa taaaatctca gacgtaccaa     1320
aatattgagg tcatcttggt tgatgatgga agtacgacag aagattctca tcgttatttg     1380
aatctcatcg agaatgattt taactctcga ggctggaaaa ttgtccgtag ttctaataac     1440
tatctgggtg ctgcaaggaa tttggctgcg cgacacgcct ctggcgaata tctgatgttt     1500
atggacgatg ataatgttgc taagcctttt gaggtagaaa cgtttgttac tgcagcatta     1560
aactctgggg ccgatgtgtt aaccacacca agcgatctta tttttggtga ggagttccct     1620
tctccgttcc gtaaaatgac gcactgctgg cttccgttag ggcctgattt aaatatcgcc     1680
agctttagta actgctttgg cgatgctaat gcgctgatca gaaaagaggt tttcgaaaaa     1740
gtaggcggat ttactgaaga ttacggttta ggtcatgaag actgggagtt ttttgccaaa     1800
atatcattac agggatataa attgcaaatc gtcccggaac ctctattttg gtatagagtt     1860
gcaaactccg gcatgttgtt aagtggaaat aagagtaaaa ataactaccg cagtttccgt     1920
ccttttatgg atgagaatgt taaatataac tatgcaatgg ggttgatacc ttcctacctc     1980
gagaagattc aagaacttga gagtgaagtg aatcgcttgc ggagcatcaa tggtggtcat     2040
tctgtcagta acgagttaca acttttaaat aataaggttg atggtcttat ttctcagcaa     2100
agagatggct gggcccatga ccgtttttaat gctctgtatg aagcaattca tgtccaaggc     2160 gcaaacgag gcaccagcct ggttcgccgg gttgcccgga aagtgaaatc aatgttaaaa     2220
taa                                                                    2223
```

<210> SEQ ID NO 31
<211> LENGTH: 810
<212> TYPE: DNA
<213> ORGANISM: Klebsiella pneumoniae

<400> SEQUENCE: 31

```
atgaccaata tgaagttaaa atttgatttg cttctaaaat cttatcatct atctcatcga       60
tttgtctata aggcaaaccc tggtaatgct ggtgatggtg taattgcatc tgcgacgtat      120 gactttttttg aacgaaatgc tcttacctat atcccttaca gagatggcga gcgctacagt      180
tctgaaactg atattttaat ttttggaggc ggaggaaacc tgatagaagg attgtattct      240
```

-continued

```
gaaggtcatg actttatcca gaataatatt gggaagtttc ataaagtaat aataatgccg      300
tcgacaatca gagggtatag cgatttattc atcaacaata ttgataagtt tgttgttttt      360
tgtcgcgaaa atatcacctt cgattatatt aaatctctca actacgaacc aaacaagaac      420
gtattcatta ctgatgatat ggcattttat ctcgatctta ataaatacct gtcacttaaa      480
cccgtctata aaaaacaggc caactgcttc agaacggact ccgaatctct aactggagac      540
tacaaagaaa acaatcatga tatttcgctc acctggaatg gcgattattg ggataatgaa      600
tttctggcgc gtaattctac ccgttgcatg ataaactttc ttgaagagta taaagttgtc      660
aataccgaca ggctgcatgt ggcaatttta gcatctctgc ttggcaaaga agtcaacttc      720
tatcctaact catattacaa aaatgaagct gtttacaatt attcactttt taatcgttat      780
ccaaaaacat gctttattac ggcaagttga                                       810

<210> SEQ ID NO 32
<211> LENGTH: 1416
<212> TYPE: DNA
<213> ORGANISM: Klebsiella pneumoniae

<400> SEQUENCE: 32
atgttgcttc ctgtgatcat ggctggtggt accggcagtc gtctctggcc gatgtctcgc       60
gagctttacc cgaaacagtt cctccgcctg ttcgggcaga actccatgct gcaggaaacc      120
atcacccgac tctcgggcct tgaaatccat gaaccgatgg tcatctgtaa cgaagagcac      180
cgcttcctgg tggccgaaca gctgcgccag ctcaacaagc tgtcgaacaa cattattctt      240
gagccggtcg ggcgcaacac cgccccggcc atcgccctgg cggccctcca ggccacccgc      300
cacggcgacg accgctgat gctggtcctc gccgccgacc atatcatcaa taaccagccg      360
gtcttccacg acgccatccg cgtcgccgag cagtatgccg atgaaggcca tctggtcacc      420
ttcggtatcg tgccgaacgc cccggaaacc ggctacggct acatccagcg cggcgtggcc      480
ctcaccgaca gcgcccacac cccgtaccag gtggcccgct cgtggagaa gccggaccgc      540 gagcgcgccg aggcctacct cgcctccggg gagtactact ggaacagcgg catgtttatg      600
ttccgcgcca aaaaatacct ctccgagctg gccaaattcc gcccggatat cctcgaagcc      660
tgccaggccg cggtcaatgc cgccgataac ggcagcgact tcatcagcat cccgcatgac      720
attttctgtg agtgcccgga cgagtccgtg gactacgcgg tgatggagaa aaccgccgac      780
gcggtggtgg tcggtctcga tgccgactgg agcgacgtcg gctcctggtc cgccctgtgg      840
gaggtcagcc cgaaagatga gcagggtaac gtcctcagcg gcgacgcgtg ggtgcacaac      900
agcgaaaact gctacatcaa cagcgacgag aagctggtgg cggccatcgg cgtggagaac      960
ctggtgattg tcagcaccaa ggacgccgtg ctggtgatga accgtgagcg ttcccaggac     1020
gtgaagaagg cggtcgagtt cctcaagcag aaccagcgca gcgagtacaa gcgccaccgc     1080
gagatttacc gtccctgggg ccgctgcgac gtggtggtcc agaccccgcg cttcaacgtc     1140
aaccgtatta cggtgaaacc gggcggcgcc ttctcgatgc agatgcacca ccaccgtgcc     1200
gagcactggg tcattctcgc cggcaccggc caggtgacgg tcaacggcaa gcagttcctg     1260
ctgaccgaga accagtccac ctttattccg attggcgccg agcacagcct ggaaaacccg     1320
ggccgcattc cgctggaagt gctggagatc cagtcggggt cgtacctcgg cgaggacgac     1380
attattcgta ttaaagacca gtatggtcgt tgctaa                               1416

<210> SEQ ID NO 33
```

```
<211> LENGTH: 1383
<212> TYPE: DNA
<213> ORGANISM: Klebsiella pneumoniae

<400> SEQUENCE: 33
atgacacagt taacatgctt taaggcttat gacatccgtg gtgaactggg cgaggagctg      60
aacgaggaca tcgcctaccg tatcggccgc gcctatggcg aatttctgaa acccgggaag     120
atagtggtgg ggggcgatgt gcgcctcacc agcgagtcgc tgaagctggc gctggcccgc     180
gggctgatgg acgccggcac cgacgtgctg gatattggcc tgagcggcac ggaagagatt     240
tacttcgcca ctttccacct cggggtggac ggcggtatcg aggtgacggc gagccataac     300
ccgatgaact acaacggcat gaagctggtg cgcgagaacg cgaagcccat cagcggcgac     360
accggcctgc gggatatcca gcgcctggcg gaggagaatc agttcgcgcc ggtagacccg     420
gcgcgtcgcg ggaccctgcg ccagatatcg gtgctgaagg agtacgtcga ccacctgatg     480
ggctatgtgg acctggcgaa cttcacccgt ccgctgaagc tggtggtgaa ctccggcaac     540
ggggcggcgg ggcacgtgat tgatgaagtg gagaaacgct tcgcggcggc cggggcgccg     600 gtgacccttta tcaaggtgca tcaccagccg gacggccatt tcccgaacgg tatcccgaac     660
ccgctgctgc cggagtgccg ccaggacacc gccgacgcgg tgcgtgcgca tcaggcggac     720
atggggatcg cctttgacgg cgacttcgac cgctgcttcc tgttcgatga cgaggcgtcg     780
tttatcgagg ggtactacat tgtcggcctg ctggcggagg cgttcctgca gaaacagccg     840
ggggcgaaaa tcattcacga cccgcgtctg acgtggaaca cggtggacat cgtgacccgc     900
agcggcggcc agccggtgat gtcgaagacg gggcatgcgt tcatcaagga gcggatgcgc     960
caggaagacg ccatctacgg cggggaaatg agtgcgcacc attacttccg cgacttcgcc    1020
tactgcgaca gcgggatgat cccgtggctg ctggtggcgg agctgctgtg cctgaagaac    1080
agttcgctga aatcgctggt ggcggaccgc caggcggcgt tcccggcgtc gggggagatc    1140
aaccgcaagc tggggaatgc ggcggaggcg atagcgcgca tccgggcgca gtatgagccg    1200
gccgccgcac acatcgacac aacggacggt atcagtattg aataccctga gtggcgcttt    1260
aacctgcgca cgtccaacac ggagccggtg gtgcgtctga cgttgagtc cagagcggat    1320 actgcgttaa tgaatgagaa aaccgccgag ctgctcaacc tgttaaaaga ggaatcgctt    1380
tga                                                                  1383

<210> SEQ ID NO 34
<211> LENGTH: 786
<212> TYPE: DNA
<213> ORGANISM: Klebsiella pneumoniae

<400> SEQUENCE: 34 atgtttttcag cgatctatcg ctaccgtggc tttattattg acagcgtcaa acgggacttt     60
cagtcccgtt accagactag cttcttaggc gcggcatggc tgatcttaca gccgatcgcc    120
atgatttccg tatatacatt aatctttttct gagttaatgc gtgcccgcct ggcgggcatg    180 gacggcccctt ttgcctacag tatctacctc tgttccgggg tgttaacctg ggggctgtttt    240 acggaaacgc tcggcaatct ggtcaacgtt tttctgacca cgccaacat tcttaaaaag    300 cttagctttc gcggatctg tttaccgatc attgtcaccg cctcggcgtt cattaacttc    360
ctgatcattt ttggtctgtt tgtactgttt ctgatcgtca cgggcaattt cccgggcatg    420
attttctttg aaatcattcc ggtgctgatc gttcagatgc tgttcacccct cggcctcggg    480 atcatcctcg gggtgctgaa cgttttttgtc cgcgacgtcg ggcagttcgt gaatatcctg    540
```

-continued

```
ctgcagtttt ggttctggtt tacgcccatt gtctacgtgt ccaaaacgct gccggagtgg      600
gtctctggtc tgctggcgta taacccgatg gcgaccatta tcggttcata ccagaacgtg      660
atgctctatc accagagccc taactggctg gcgctgcttc cggtcacggt gctgtccgtc      720
attctgtttt tatttgcctg gcgtttattt aaaaaacatg ccgctgatat tgtggacgag      780
atttaa                                                                786

<210> SEQ ID NO 35
<211> LENGTH: 1296
<212> TYPE: DNA
<213> ORGANISM: Klebsiella pneumoniae

<400> SEQUENCE: 35
atgagtatca aagttcagca cgtcggcaag gcgtataaat attatccctc caaatggaac       60
cgggtcattg agaaacttct gccgggcgat aagccgcggc acagcaagaa atgggtattg      120
aaagatatca atttcagtat tgaacccggt gaagcggtcg gcattgttgg ggtgaacggc      180
gcaggtaaaa gtacgttact gaagctgctg actggcacca ctcagccgac caaaggcagc      240
attgagatcc aggggcgtgt cgctgcgctg ctggagctgg gcatgggctt ccatcctgac      300
tttaccggtc ggcagaacgt gtatatgtcc gggctgatga tgggcctgag ccgggaagag      360
attgagcgct taatgccgga gatcgaagcc tttgcggata tcggtgacta cattgaagag      420
cccgtgcgca tctactccag cgggatgcaa atgcgcctgg cgttcgccgt ggccacggcc      480
tcacgcccgg atattctgat cgtcgatgaa gcgctttccg ttggtgactc ccgctttcag      540
gcgaagtgct atgcccgtat tgcggacttc aaaaagcagg gcaccacgct gctgctggtc      600
tcccacagcg ccggggatat cgtcaaacac tgtgaccgcg ccattttcct caaaaatggt      660
gatatctgta tggacggcac cgcccgtgac gtgaccaacc gttatctgga tgagctgttt      720
ggcaaagccg acaaaaacag cgcgccaaaa agcgaaacgg caacctcgtc agccagcggc      780
gaaagtcaga tgtctctcga tgagattgaa gatgtgtacc acacgcgccc aggctaccgt      840
ccggaagagt accgttgggg gcaggggggt gcaaaaatca ttgattatca catccaaagc      900
gccggggttg attttccgcc ttcactgacg ggcaatcagc agaccgattt cctgatgaaa      960
gtcgtatttg aatatgactt tgattgcgtg gtaccgggtt tgttaatcaa aactctggat     1020
ggcttatttc tatatggtac caactctttc ctggcctcgg aaggccggga aaacatttcg     1080
gtatcacgtg gggacgttag agtatttaaa ttcagttttc cggttgattt aaatagcggt     1140
gactatcttc tgtcgtttgg tatttcagag ggaagcccgc aaaccgaaat gacgccgctc     1200
gatcgtcgct atgactccat cattttgcat gtaactaaga gcatggattt ctggggagtg     1260
attgacctga gtcgactttt caatagttac aaatga                              1296

<210> SEQ ID NO 36
<211> LENGTH: 2058
<212> TYPE: DNA
<213> ORGANISM: Klebsiella pneumoniae

<400> SEQUENCE: 36
atgactacta atacacataa attggttagc gaattacctg aaatttatca gactattttt       60
gggcatcctg agtgggatgg cgatgctgca cgagactgta tgaacggct cgcgctaatt      120 agtgaacaat atgacagctt gtccagagag ttaggaaggc cactacgggt tctcgacctg      180
ggctgtgctc aggggttctt cagtttaagt ttggcaagca agggtgccag cgtattaggt      240
```

-continued

```
atcgactttt tgcagcagaa cattgatgtt tgtcaggcgc ttgctgaaga aaatccacat    300
tgtgatgtta aatttcaagt cgggcggata gaagacattg tcagcactct ggaagaaaac    360
caatttgatc tcgccattgg actaagtgtt tttcaccaca ttgttcatct gcatggggtt    420
gctgaagtca gatcgctgtt agagcgtttg gcaaatctga cgcaggcgat gattctcgag    480
ctcgctgtca aggaggaacc actctattgg gggaaatctc agcctgaaga tccgcgtgaa    540
cttattgacc aatgtgcttt ctatcgattg attggaagat ttgacactca tctgtctaat    600
atttcacgtc cgatgtatat tatcagtaac cacagggtta ttcttccgga atttaatcag    660 cctttactt catggcgcga cagtccttac accggagcag gctttgcgca taaacagagc    720
cgtcgctatt atttctcttc ggagttcata tgtaagttct atcgtttag tacagtaagt    780 tgcttactaa ctgataagga gagcgagcgt aatcgtactg aactcgccca tgaagaagct    840
tttcttaaat ctccaccatc tggcttaaaa gtgccggcgt tgtttactgc aggggggaat    900
ggagaagcgg gatggttggt aatggaaaaa attcccggag agctgttaaa cgacgttctg    960
gccagtgaac ggcatattga tcgggaaaaa gttatttccg atctcctcga ccaattagtt   1020
attttggaag aacatggtct atatcatgat gatttcagaa catggaatgt tttaattgac   1080
gataatgaca gcgctcgttt aatagatttt ggttcgattg gcgatgtaca acaagactgc   1140
agctggccag ttaatatttt ccagtcgttc attatttttg taaatgaaat attttgtgaa   1200
aataaatcct ggaggggctt ctggcgttcc gcaccattaa gtcctttcca gttgcctgaa   1260
ccgtattcaa attggttgac agcattctgg aaacatcctg ttggtgagtg gagttttgct   1320
ttactccaac aactcttttc aaccaaagat gctctaccgg ctgcgagttc cattatggac   1380
gcttctgatc tatgggtccg ggctcaggag cccgtattgt tggaaagtca aacgcaaata   1440
cgcaatacgg atgcgcgggt agtccgtctc gagtcgcaaa tcaatgaact cacctccctg   1500
attaatatta tgggtgagag cattcagacg tttgagaagc gtgagtatcc gccacaagac   1560
gttactacta atgtacagcc gcgtatcgag attgagcaga gtaaagccgt tgattcagaa   1620
gagattatgc gacttcatac gcagctcaat gatgctcagc aagaaataga gaatctacgt   1680
catgagattg ctaaaattca ttatagtcgc tcatggaaaa tgaccaagtg gtatcggtac   1740
gctggcttac agtactatct gcttcgtcag tacggcttca aacagcgttt taagcattta   1800
ctcaaacgag tgcttagcaa cgtaatttat tttttgcgtg cacatccacg actaaagcag   1860
aaggtgatca atctactgcg tacaattgga atttatgact ttgcttatcg tatgcatcgt   1920
cgtatgaatc ctggttcaca taacccttat ccaaacgacc cacaatacca gtcgcagact   1980
gaaaagcaga tcttacatcc agagttattg cctccggaag ttaactcaat ttttagcgag   2040
cttaaaaaca aaagataa                                                  2058
```

```
<210> SEQ ID NO 37
<211> LENGTH: 2523
<212> TYPE: DNA
<213> ORGANISM: Klebsiella pneumoniae

<400> SEQUENCE: 37
ttgcatattt tgattgacgt acaaggatat caatcggaaa gtaaattccg tggagttggt     60
cgcagcacct atgaaatgag tcgtgcgatc ataaaaaatg ctggccagca tcgagtaagc    120
attttaatga atggcatgta ttcgattgat agtataaatg aaattaaaaa aagctggggt    180
gatatattac cgcaggaaga aatgtttatt ttttcagctg ctggccctac agctcttcgc    240
gactgtgaaa accatccccg gagtgttgcc gccacactag ctcgtgaact tgctattgct    300
```

-continued

```
aatatcaatc ccgacgttgt ttttattatt aatttctacg aaggtttttga cgatagttat      360 accgtctcaa ttcctcaaac tacagtacca tggaaaacag tttgtgtttg tcacgatcta      420
attccgttac tgaataaaga acgctatctg ggcgaaccaa acttccgtca gtattattat      480
gataaactag ctcaatacga aagggcggac gctatttttg ctatttccag atcatccatg      540
caggaagtta tcgattacac atcgattccg gcagaaaaaa ttattaatat ttcatctgga      600
gtaagcgatt catttaaaat taaagattat actcacgatg aaatcaaaga cttacgtaat      660
aaatatcatc ttcctcaaga gtttattctt tctttggcaa tgatagagcc acgtaaaaat      720
attgaagcgc tgattcatgc atatagttta ttaccgcatg ccctgcaaca gagttatccc      780 ttagtttttag cctataaaat tagcaccgat gaaaaggaaa ggctgtaccg agttgcagag      840
aactatggtt tatctcgtaa tcagcttatt tttacaggct tcttaaacga tagtgacctt      900
atcgcacttt acaatttgtg caaaattttc gttttcccct ctatacatga agggtttggc      960
ctgccgccac tagaagctat gcgttgtggt gcagctacgc tgggttcaaa tgtgaccagc      1020
ttacccgagg tcatcggtat ggaagaggct ttatttaatc ctctggatgt ccccgacatt      1080
tgccgtgtta tgcaaagggc cttgactgac agtgagttct actcagcatt aaaagctcat      1140
gctccggcgc aggcggcaaa gttcacatgg gatcacaccg cgcagctcgc gttaaaggga      1200
tttgagaggc ttgtagataa ggcttccgca tcagaacctc tggatatcac aagcttcacc      1260
gcatacacca ttaatagaat taaaaatatt gcagaattaa gtgaaaccga acgcttacag      1320
acagcctggg cgattgctcg taatagcttt gctacacatc agcgcaagct gctggttgat      1380
atttctgttc ttgttgagca tgatgcgaaa acgggaattc aacgggtttc tcgcagtata      1440
cttagtgaat tactgaaatc tggcgttgct ggttatactg tcagtgcggt ttattatcga      1500
ccgggtgaat gctatcgcta tgccaacgaa tacctgaata cccattttaa cggggcgttc      1560
gggcctgatg tacctgtact gtttaccaaa gatgatattc tggttgctac cgatctaact      1620
gcccatctgt ttcctgagct tactgtccag ctggatttta ttcgtctatc cggtgccaag      1680
gtttgttttg ttgtgcatga catttttgcct ctgagaagac cggagtggag cgatgaggga      1740
atgcaacgcg tgttccccat ttggttatct tgcattcgc agcacgcaga ccgcttgatt      1800
tgtgtatcag caagcgttgc agaggatgta aaagcctgga ttgcggaaaa cagccattgg      1860
gtgaaaccga acccgctgct gaccgtcagc aacttccatc tgggagccga cctcgatgcc      1920
agcgtaccgt ccactggcat gccggataat gcccaggcgc tgttagcagc gatggccgcg      1980
gctccatcat ttatcatggt gggcacgatg gaaccacgca aaggacatgc gcagacgcta      2040
gcggcatttg aagaattgtg gttacagggc aagaactaca atctgtttat cattggtaaa      2100
caggggtggc atgttgatga tttatgtgaa cgtttacgtc accatccaca gctaaataaa      2160
aaactatttt ggctacaaaa cattagcgat gagttcctta cgaagttgta ttctcagtct      2220
agtgcgttaa tcttcgcatc tctcggagaa ggctttggcc tgccgttgat tgaagcggcg      2280
cagaaaaagc tgccggtgat tatccgtgac attccggtgt ttaaagagat tgctcaggaa      2340
catgcgtggt atttctccgg ggaagcgccg gccgacatcg cgaaggccgt cgaagactgg      2400
ttagccctgt atgagcaaaa cgcgcatcct cgttccgaga atatcaactg gttaacctgg      2460
aagcagagcg cggaatttct cctgaaaaac ctgccgatta tcgcgccagc cgcgaagcaa      2520
taa                                                                    2523
```

<210> SEQ ID NO 38

-continued

```
<211> LENGTH: 1146
<212> TYPE: DNA
<213> ORGANISM: Klebsiella pneumoniae

<400> SEQUENCE: 38
atgaaaatta tttttgctac tgagccaatt aaatacccgt taacgggcat cggtcggtat      60
tccctggagc tggttaagcg gctggcggtc gcccgcgaaa tcgaagagct gaagctgttt     120
cacggcgcgt cgtttatcga tcagatcccc caggtggaga ataaaagcga taccaaagcc     180
agcaatcatg gtcgtttgtc ggcgtttctg cgccgccagc cgctgctgat tgaggcgtat     240
cgcctgctgc acccgcggcg ccaggcgtgg gcattgcgcg actataaaga ttatatctac     300
catggtccca attttttacct gccgcatcgc ctggaacacg ccgtgaccac gtttcatgac     360
atctccattt ttacctgccc ggaatatcat ccaaaagatc gggttcgcta tatggagaag     420
tccctgcatg agagcctgga ttcggcaaag ctgatcctga ccgtctctga cttctcgcgc     480
agtgaaatca tccgcctgtt caactatccg gcggagcgga tcgtcaccac caagctggcc     540
tgcagcagcg actatattcc acgcagcccg gcggagtgcc tgccggtcct gcagaaatat     600
cagctggcgt ggcaggggta tgcgttatat atcggcacca tggagccgcg taaaaatatc     660
cgtggtctgc tgcaggccta tcagctgctg ccgatggaga cccgcatgcg ctacccgctg     720
atcctcagcg gctatcgcgg ctgggaagac gatgtgctgt ggcagttagt cgagcgtggt     780
acgcgtgaag ggtggatccg ttacctgggc tatgtcccgg atgaggacct gccttatctg     840
tacgcggcgg ccagaaacctt tgtttatccc tccttctatg agggattcgg tttacctatt     900
cttgaagcga tgtcttgcgg tgtgccggta gtatgttcca atgtcacttc tttgcctgag     960
gtggttggcg atgccggcct cgttgccgat cctaatgatg tagacgcgat tagcgcgcat    1020
attttgcaga gcctgcagga tgatagctgg cgggaaatcg ccaccgcgcg cggtcttgcc    1080
caggcgaaac agttttcgtg ggagaactgt acgacccaga ccattaacgc ctataaatta    1140
ctctaa                                                                1146

<210> SEQ ID NO 39
<211> LENGTH: 1116
<212> TYPE: DNA
<213> ORGANISM: Klebsiella pneumoniae

<400> SEQUENCE: 39
ttgagagttc tacacgtcta taagacctac tatcccgata cctacggcgg tattgagcag      60
gtcatttatc agctcagtca gggttgcgcc cgccggggga tcgcagccga tgttttttact     120 tttagcccgg acaaagagac aggtcctgtc gcctacgaag accatcgggt catttataat     180
aagcagcttt ttgaaattgc ctccacgccg ttttcgttga aagcgttaaa gcgttttaag     240
cagattaaag atgattacga catcatcaac taccattttc cgtttccctt tatggatatg     300
ctgcatctct cggcgcggcc tgacgccaga acggtggtga cctatcactc ggatattgtg     360
aaacaaaaac ggttgatgaa gttgtaccag ccgctgcagg agcgattcct cgccagcgta     420
gactgcattg ttgcctcgtc gcccaactac gtggcctcca gccagaccct gaaaaaatat     480
caggataaaa cggtggtgat cccgtttggt ctggagcagc atgacgtgca gcacgatccg     540
cagcgggtgg cgcactggcg ggaaaccgtc ggcgataact tcttcctctt cgtcggcgct     600
ttccgctact acaaagggct gcacattctg ctggatgccg ccgagcgtag ccggctgcca     660
gtggtgatcg tcggggcgg gccgctggag gcggaggtgc ggcgtgaggc gcagcagcgc     720
ggactgagca atgtggtgtt taccggcatg ctcaacgacg aagataaata cattctcttc     780
```

-continued

```
cagctctgcc ggggcgtggt cttcccctcg catctgcgct cagaggcgtt tggcattacg    840
ttactggaag gcgcgcgctt tgccaggccg ctgatctcct gcgagatcgg caccggtacc    900
tcgttcatta accaggacaa agtaaatggc tgcgtgatcc cgccgaatga cagtcaggcg    960
ctggtggagg cgatgaatga gctctggcat aacgatgaaa ccgccagccg ctatggcgaa    1020
aactcgcgtc gtcgttttga agagatgttt acagccgacc atatgattga cgcttacgtc    1080
aatctctaca ctacgctgct ggaaagcaaa tcctga                              1116

<210> SEQ ID NO 40
<211> LENGTH: 27
<212> TYPE: DNA
<213> ORGANISM: Artificial
<220> FEATURE:
<223> OTHER INFORMATION: PCR Primer

<400> SEQUENCE: 40
gaaggcgggc gcgtgaccat tctcggc                                         27

<210> SEQ ID NO 41
<211> LENGTH: 27
<212> TYPE: DNA
<213> ORGANISM: Artificial
<220> FEATURE:
<223> OTHER INFORMATION: PCR Primer

<400> SEQUENCE: 41
gccgagaatg gtcacgcgcc cgccttc                                         27
```

VACCINE

CROSS-REFERENCE TO RELATED APPLICATIONS

The instant application is a National Stage Application under 35 U.S.C. § 371 of International Application No. PCT/EP2021/066343, filed Jun. 17, 2021, which claims priority under 35 U.S.C. § 119(e)(1) to U.S. Provisional Application No. 63/043,883, filed Jun. 25, 2020. The complete contents of each of the above-listed application are hereby incorporated by reference in their entireties.

REFERENCE TO SEQUENCE LISTING

The instant application contains a Sequence Listing which has been submitted electronically in ASCII format and is hereby incorporated by reference in its entirety. Said ASCII copy, created on Nov. 2, 2022, is named VB66938 FF_ST25.txt and is 62,760 bytes in size.

FIELD OF THE INVENTION

The present invention relates to the field of immunogenic compositions and vaccines, their manufacture and the use of such immunogenic compositions and vaccines in medicine. More particularly, it relates to immunogenic compositions comprising *Klebsiella pneumoniae* O-antigen polysaccharide conjugates.

BACKGROUND TO THE INVENTION

*Klebsiella pneumoniae* is a gram-negative, encapsulated non-motile bacteria of the Enterobacteraceae family. It colonizes the gastrointestinal, respiratory and urinary tracts and is carried asymptomatically as part of the human microbiome. *Klebsiella pneumoniae* is an important cause of community, long term care facilities and hospital-acquired infections. It is among leading causes of serious infections in newborns, blood cancer patients, and other immunocompromised patients. It causes: urinary tract infections, pneumonia, bacteraemia and soft tissue infections. Infections caused by *Klebsiella pneumoniae* are responsible for high rates of morbidity and mortality. The mortality rate of *Klebsiella* bacteraemia and pneumonia can exceed 50% even with antimicrobial therapy. In *K. pneumoniae*, carbapenemases are the main contributing factor to extensive drug resistance (David et al. (2019) Nature Microbiology, VOL 4, 1919-1929). The emergence of hypervirulent isolates and the increase in isolates resistant to β-lactams, including carbapenems, and limited treatment options make *Klebsiella pneumoniae* a global health concern. Alternative approaches to antibiotics are highly needed (HyperTextTransferProtocolSecure://www.who.int/medicines/publications/global-priority-list-antibiotic-resistant-bacteria/en). However, there is currently no vaccine on the market.

*Klebsiella pneumoniae* expresses two types of polysaccharide molecules on the surface: capsular polysaccharide (K-antigen) and lipopolysaccharide (O-antigen, also known as O-antigen polysaccharides or OPS). Capsule polysaccharides are highly diverse with at least 77 serologically distinct K-antigens. In contrast, the diversity of O-antigen structures in the lipopolysaccharides of *Klebsiella pneumonia* is limited. Nine serotypes have been identified: O1, O2, O2ac, O3, O4, O5, O7, O8, and O12. There are subtypes within these serogroups, for example, O3 serogroup has three different subtypes differing in the number of mannose residues within the O-antigen repeating units (Guachalla et al. (2017) Scientific Reports 7:6635, 1-13). The carbohydrate repeating unit structures of OPSs of *K. pneumoniae* are described in FIG. 1 of Clarke et al. J. Biol. Chem. (2018) 293(13) 4666-4679 and FIG. 1 of Kelly et al. J. Biol. Chem. (2019) 294(28) 10863-10876, which also describe the biosynthesis of certain O-antigens. According to Clarke et al. (2018) genes outside the main rfb (O-antigen biosynthesis) locus (i.e. the six genes wzm-wbbO) can have profound effects on the final structure (see FIG. 2 of Clarke et al.).

Conjugate vaccines (vaccines comprising a carrier protein covalently linked to an immunogenic antigen) have been a successful approach for vaccination against a variety of bacterial infections. Conjugation of T-independent antigens, for example saccharides, to carrier proteins has long been established as a way of enabling T-cell help to become part of the immune response for a normally T-independent antigen. In this way, an immune response can be enhanced by allowing the development of immune memory and boostability of the response. Hegerle et al. (2018) (PLOS ONE 13(9): e0203143) report the development of a combined *Klebsiella pneumoniae* and *Pseudomonas aeroginosa* glycoconjugate vaccine comprised of the four most common *Klebsiella pneumoniae* OPS types associated with human infections (O1, O2, O3, O5), chemically linked to the two flagellin types of *Pseudomonas aeruginosa* (FlaA, FlaB).

There is a need to develop vaccines which can protect against *Klebsiella pneumoniae* infections. In particular, there is a need for a broad spectrum vaccine.

SUMMARY OF THE INVENTION

The present invention provides immunogenic compositions (e.g. vaccines) and methods of using them to protect against *Klebsiella pneumoniae* infections, in particular, protect against a specific combination of subserotypes of *Klebsiella pneumoniae*. These immunogenic compositions and methods are the first to consider the prevelance of certain *Klebsiella pneumoniae* subserotypes (i.e., O1v1 vs O1v2, O2afg vs O2a, O3 vs O3b), the first to consider antibiotic resistant *Klebsiella pneumoniae*, and the first to consider cross-reactivities between distinct *Klebsiella pneumoniae* subserotypes. The importance of these subserotypes (in particular the prevalence of subserotypes in patients infected by *Klebsiella pneumoniae*) and their cross-reactivities were not previously recognised or considered in relation to the design and composition of immunogenic compositions (e.g. vaccines) for protecting against *Klebsiella pneumoniae* infections. Immunogenic compositions and vaccines of the present invention provide broad coverage against several different subserotypes of *Klebsiella pneumoniae*. Furthermore, the present invention also provides novel conjugates, in particular bioconjugates, against the subserotypes O1v1, O2a, O2afg, O3b of *Klebsiella pneumoniae* which can be used in the immunogenic compositions (e.g. vaccines) and methods of the invention.

Accordingly, there is provided in one aspect of the present invention, an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are individually conjugated to a carrier protein.

According to a further aspect of the invention, there is provided a process for making an immunogenic composition of the invention, comprising combining a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, and optionally a pharmaceutically acceptable excipient and/or carrier.

According to a further aspect of the invention, there is provided a host cell comprising:

i) nucleotide sequences comprising polysaccharide synthesis genes for producing a *Klebsiella pneumoniae* O-antigen polysaccharide selected from O1v1, O2a, O2afg and O3b, optionally integrated into the host cell genome;

ii) a nucleotide sequence encoding a heterologous oligosaccharyl transferase, optionally within a plasmid;

iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and iv) a nucleotide sequence encoding an ABC transporter, optionally *K. pneumoniae* genes wzm and wzt, optionally integrated into the host cell genome.

According to a further aspect of the invention, there is provided a process for producing a bioconjugate comprising (i) culturing the host cell of any the invention under conditions suitable for the production of glycoproteins and (ii) isolating the bioconjugate.

According to a further aspect of the invention, there is provided a conjugate (e.g. bioconjugate) comprising a *Klebsiella pneumoniae* O-antigen polysaccharide selected from O1v1, O2a, O2afg or O3b conjugated to a carrier protein, wherein the carrier protein is a detoxified Exotoxin A of *Pseudomonas aeruginosa* (EPA).

According to a further aspect of the invention, there is provided an immunogenic composition comprising the conjugate (e.g. bioconjugate) of the invention, and optionally a pharmaceutically acceptable excipient and/or carrier.

According to a further aspect of the invention, there is provided a vaccine comprising the immunogenic composition of the invention and optionally an adjuvant.

According to a further aspect of the invention, there is provided a method of inducing an immune response to *Klebsiella pneumoniae* in a subject, the method comprising administering a therapeutically or prophylactically effective amount of the immunogenic composition of the invention, or the vaccine of the invention, to a subject in need thereof.

According to a further aspect of the invention, there is provided an immunogenic composition of the invention, or the vaccine of the invention, for use in inducing an immune response to *Klebsiella pneumoniae* in a subject.

According to a further aspect of the invention, there is provided an immunogenic composition of the invention for use in the manufacture of a medicament for inducing an immune response to *Klebsiella pneumoniae* in a subject.

DESCRIPTION OF DRAWINGS/FIGURES

Figure 2C:
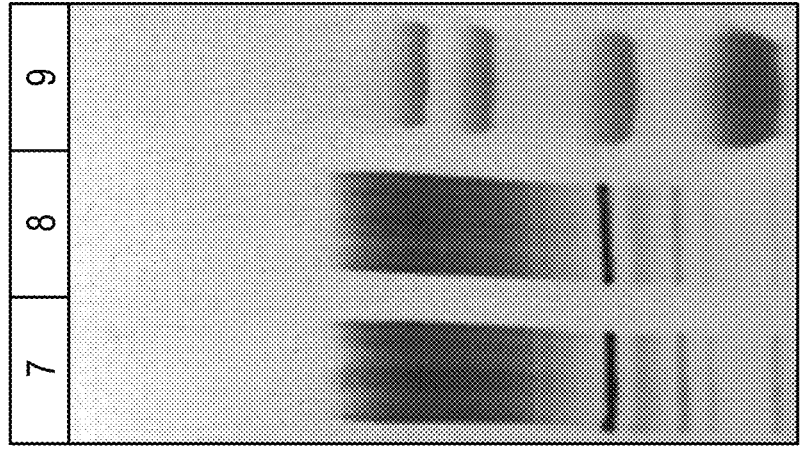

FIGS. 1A and 1B: Analysis of the O3b and O2afg glycan-producing strains (A and B, respectively) when transformed with plasmids encoding pglB and EPA with different number of PglB glycosylation consensus sequences. Periplasmic extracts were used for O3b (A), while enriched periplasmic extracts were used for O2afg (B). The used carriers contain 3 glycosylation sites (B, lane 1), 4 glycosylation sites (A, lane 7; B lane 2), 5 glycosylation sites (A, lanes 1, 2, and 3), 6 glycosylation sites (A, lanes 4 and 5), 7 glycosylation sites (A, lane 6). PAGERULER™ Prestained Protein Ladder (ThermoFisher) is indicated by "M".

FIGS. 2A, 2B, 2C, and 2D: Analysis of the O1v1, O2a, O2afg, and O3b-conjugate-producing strains' products (A, B, C, and D, respectively). Two experimental replicates per serotype are analysed. Coomassie staining (A, left picture; B; C, right picture; D), anti *K. pneumoniae* O1v1 Western blot (A, central picture), anti *K. pneumoniae* O2a Western blot (A, right picture; C, left picture), anti *K. pneumoniae* O2afg Western blot (C, central picture) are shown. PAGERULER™ Prestained Protein Ladder (ThermoFisher) is loaded in lanes 1, 4, 9, 10, the corresponding band size in kDa is reported. Other lanes contain the two replicas from each conjugate-producing strain.

Figure 3:
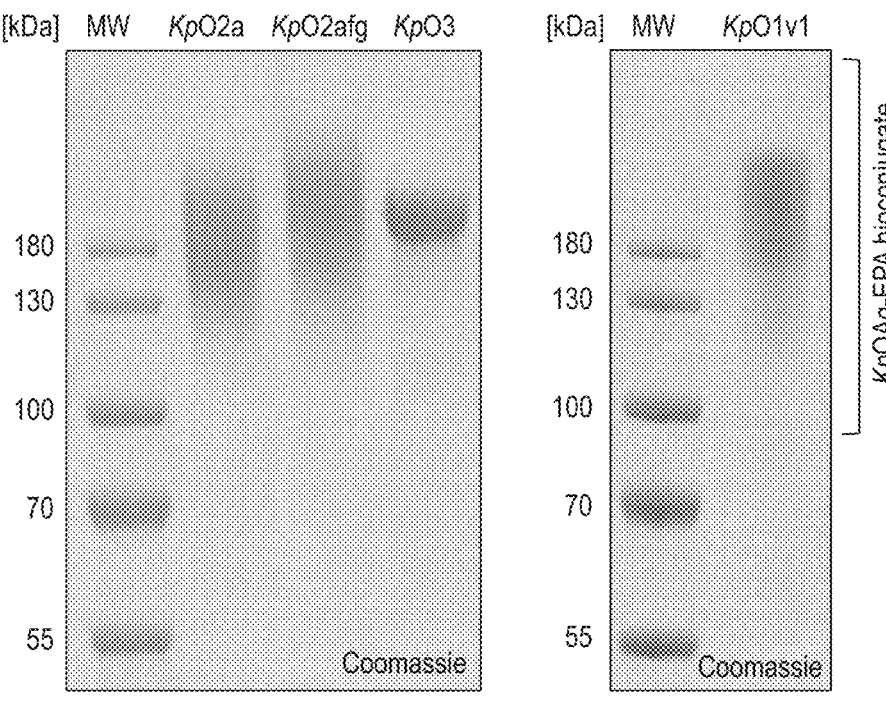

FIG. 3 Purified conjugates were analyzed via SDS-PAGE and Coomassie staining.

Figure 4:
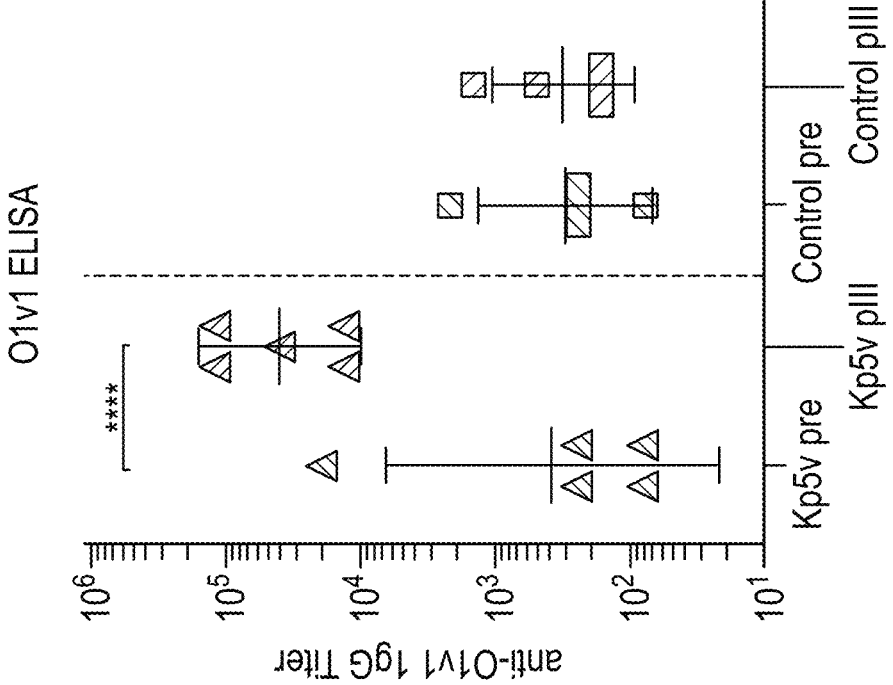

FIG. 4 IgG titers analysed in sera of rabbits immunized with 1 μg polysaccharide of polyvalent conjugate composition. Only Pre-immunization and Post-III sera results are reported. Lines and bars indicate the geometric mean titer (GMT) +/−95% confidence interval. **: $p < 0.0001$, : $p < 0.01$, ANOVA-Sidak's multiple comparisons. "Control" indicates immunizations carried out with buffer only.

Figure 5:
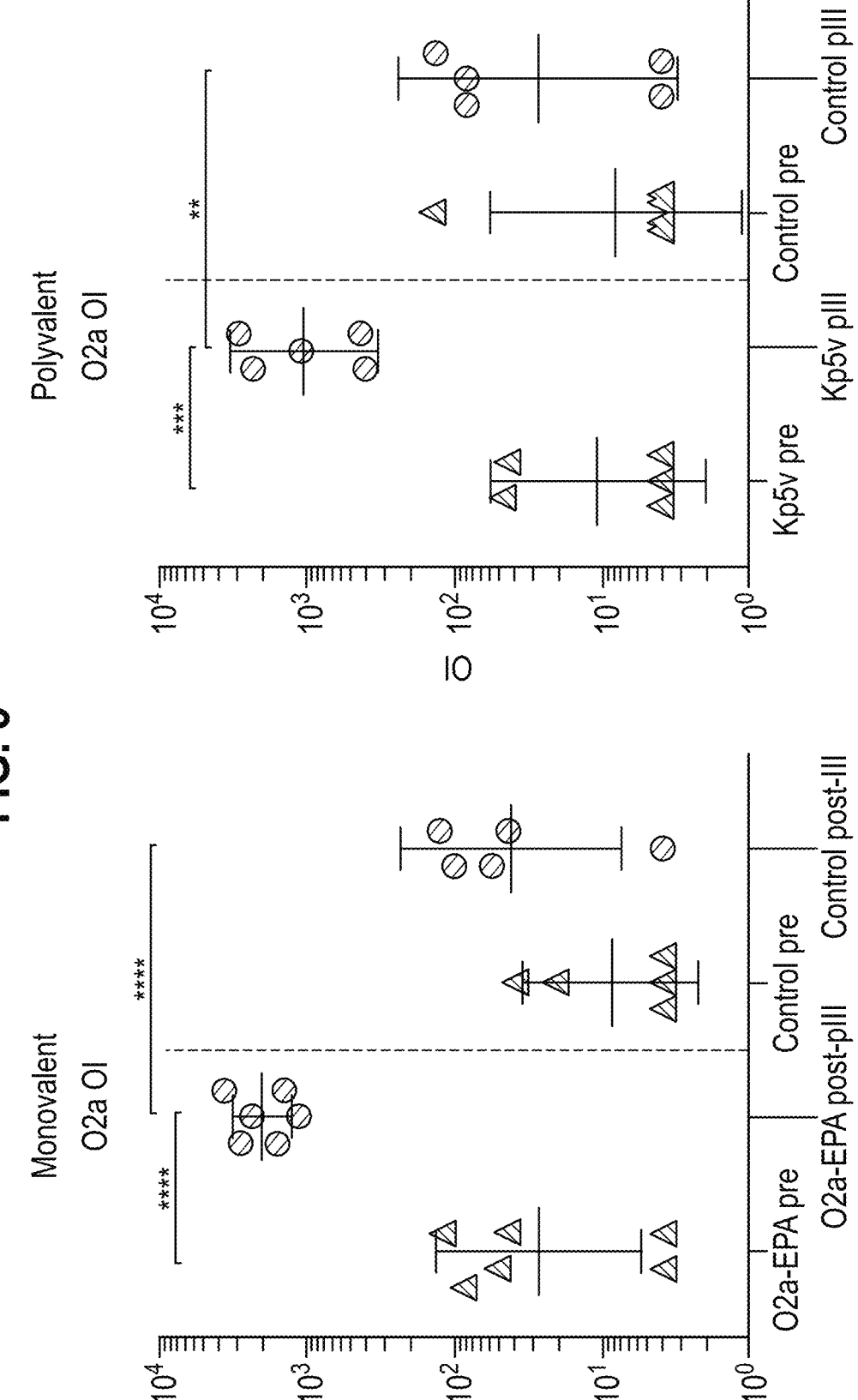

FIG. 5 O2a opsonisation index (OI) in pre- and post-III immunization sera from rabbit immunized with monovalent O2a conjugate or polyvalend Kp5v composition. O2a wild type strain was used. Control group are animals immunized with buffer alone. Lines and bars indicate the GMT +/−95% confidence interval. **: $p < 0.0001$, *: $p < 0.001$, **: $p < 0.01$, ANOVA-Sidak's multiple comparisons.

FIG. 6 *K. pneumoniae* wild type strains were tested for binding with pools of sera of animals immunized with monovalent vaccine via flow cytometry. Median fluorescence intensity due to the binding of the antisera to the cells is reported. Mean and standard deviation are shown. New Zealand white rabbits were injected at days 0, 14 and 28 with 1 μg of monovalent vaccine with no adjuvant. Control group are animals immunized with buffer alone.

DETAILED DESCRIPTION OF THE INVENTION

Definitions

Carrier protein: a protein which may be covalently attached to an antigen (e.g. saccharide antigen, such as a bacterial polysaccharide antigen) to create a conjugate (e.g. bioconjugate). A carrier protein activates T-cell mediated immunity in relation to the antigen to which it is conjugated.

EPA: Exotoxin A of *Pseudomonas aeruginosa* (also known as "Exotoxin of *P. aeruginosa*", "EPA", or "ETA")

Any amino acid except proline (pro, P): refers to an amino acid selected from the group consisting of alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), serine (ser, S), threonine (thr, T), tryptophan (trp, W), tyrosine (tyr, Y), and valine (val, V).

Naturally occurring amino acid residues: amino acids that are naturally incorporated into polypeptides. In particular, the 20 amino acids encoded by the universal genetic code: alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

O-Antigens (also known as O-specific polysaccharides or O-side chains): a component of the surface lipopolysaccharide (LPS) of Gram-negative bacteria. Examples include O-antigens from *Klebsiella pneumoniae*. As used herein a "*Klebsiella pneumoniae* O-antigen polysaccharide O1v1" is an O-antigen polysaccharide from *Klebsiella pneumoniae* serotype O1v1. As used herein a "*Klebsiella pneumoniae* O-antigen polysaccharide O2a" is an O-antigen polysaccharide from *Klebsiella pneumoniae* serotype O2a. As used herein a "*Klebsiella pneumoniae* O-antigen polysaccharide O2afg" is an O-antigen polysaccharide from *Klebsiella pneumoniae* serotype O2afg. As used herein a "*Klebsiella pneumoniae* O-antigen polysaccharide O3b" is an O-antigen polysaccharide from *Klebsiella pneumoniae* serotype O3b.

Lipopolysaccharide (LPS): large molecules consisting of a lipid and a polysaccharide composed joined by a covalent bond.

wzy: a polysaccharide polymerase gene encoding an enzyme which catalyzes polysaccharide polymerization. The encoded enzyme transfers oligosaccharide units to the non-reducing end forming a glycosidic bond.

waaL: a O-antigen ligase gene encoding a membrane bound enzyme. The encoded enzyme transfers undecaprenyl-diphosphate (UPP)-bound O-antigen to the lipid A core oligosaccharide, forming lipopolysaccharide.

"D-galactan I" as used herein is a reference to a polymer built of [→3)-β-D-Galf-(1→3)-α-D-Galp-(1→] repeating units (see Hsieh et al. 2014 Front. Microbiol. 5:608, doi: 10.3389/fmicb.2014.00608).

"D-galactan II" as used herein is a reference to a polymer built of [→3)-α-D-Galp-(1→3)-β-D-Galp-(1→] repeating units (see Hsieh et al. 2014 Front. Microbiol. 5:608, doi: 10.3389/fmicb.2014.00608).

"D-galactan III" as used herein is a reference to a polymer built of [→3)-β-D-Galf(1→3)-[α-D-Galp-(1→4)]-α-D-Galp-(1→] repeating units (see Stojkovic et al. 2017 Front. Microbiol. 8:684, doi: 10.3389/fmicb.2017.00684).

"GlcNAc" as used herein is a reference to N-Acetylglucosamine.

"Gal" or "Galp" as used herein is a reference to D-galactopyranose.

"Galf" as used herein is a reference to D-galactofuranose.

"Man" as used herein is a reference to D-Mannopyranose.

As used herein, the term "conjugate" refers to carrier protein covalently linked to an antigen. For example, a *Klebsiella pneumoniae* O1v1 O-antigen polysaccharide conjugate comprises a carrier protein covalently linked to an *Klebsiella pneumoniae* O1v1 O-antigen polysaccharide. For example, a *Klebsiella pneumoniae* O2a O-antigen polysaccharide conjugate comprises a carrier protein covalently linked to an *Klebsiella pneumoniae* O2a O-antigen polysaccharide. For example, a *Klebsiella pneumoniae* O2afg O-antigen polysaccharide conjugate comprises a carrier protein covalently linked to an *Klebsiella pneumoniae* O2afg O-antigen polysaccharide. For example, a *Klebsiella pneumoniae*

O3b O-antigen polysaccharide conjugate comprises a carrier protein covalently linked to an *Klebsiella pneumoniae* O3b O-antigen polysaccharide.

As used herein, the term "bioconjugate" refers to conjugate between a protein (e.g. a carrier protein) and an antigen (e.g. a saccharide antigen, such as a bacterial polysaccharide antigen) prepared in a host cell background, wherein host cell machinery links the antigen to the protein (e.g. N-linked glycosylation).

As used herein an amino acid sequence may have a certain % identity to a reference amino acid sequence. Variants may differ from the reference amino acid sequence by the deletion and/or addition and/or substitution of one or more amino acids (e.g. 1, 2, 3, 4, 5, 6, 7, 8, 9, 10, 11 or 12 amino acids). Amino acid substitution may be conservative or non-conservative. In one aspect, amino acid substitution is conservative. Substitutions, deletions, additions or any combination thereof may be combined in a single variant so long as the variant is an immunogenic polypeptide. In an embodiment, 1 to 10, 5 to 10, 1 to 5, 1 to 3, 1 to 2 or 1 amino acids of the reference amino acid sequence may be substituted or deleted.

As used herein, the term "conservative amino acid substitution" involves substitution of a native amino acid residue with a non-native residue such that there is little or no effect on the size, polarity, charge, hydrophobicity, or hydrophilicity of the amino acid residue at that position, and without resulting in decreased immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

As used herein, the term "deletion" is the removal of one or more amino acid residues from the protein sequence. Typically, no more than about from 1 to 6 residues (e.g. 1 to 4 residues) are deleted at any one site within the protein molecule.

As used herein, the terms "insertion" or "addition" (including other tenses thereof such as "inserted") means the addition of one or more non-native amino acid residues in the protein sequence or, as the context requires, addition of one or more non-native nucleotides in the polynucleotide sequence. Typically, no more than about from 1 to 10 residues, (e.g. 1 to 7 residues, 1 to 6 residues, or 1 to 4 residues) are inserted at any one site within the protein molecule.

As used herein, the term "added next to" is the addition of one or more non-native amino acid residues in the protein sequence at a position adjacent to the referenced amino acid or amino acid region.

A "consensus sequence" is a sequence have a specific structure and/or function. As used herein, the term "consensus sequence" is a sequence comprising a glycosite. A consensus sequence may be selected from: a five amino acid consensus sequence D/E-X-N-Z-S/T (SEQ ID NO: 1), a seven amino acid consensus sequence K-D/E-X-N-Z-S/T-K (SEQ ID NO: 2) or an extended consensus sequence (e.g. J-D/E-X-N-Z-S/T-U (SEQ ID NO: 4)).

Unless specifically stated otherwise, providing a numeric range (e.g. "25-30") is inclusive of endpoints (i.e. includes the values 25 and 30).

The terms "identical" or percent "identity" refer to nucleotide sequences or amino acid sequences that are the same or have a specified percentage of nucleotide residues or amino acid residues that are the same (e.g. 80%, 85%, 90%, 92%, 95%, 96%, 97%, 98% or 99% identity over a specified region), when compared and aligned for maximum correspondence using, for example, sequence comparison algorithms or by manual alignment and visual inspection. Identity between polypeptides may be calculated by various algorithms. In general, when calculating percentage identity the two sequences to be compared are aligned to give a maximum correlation between the sequences. This may include inserting "gaps" in either one or both sequences, to enhance the degree of alignment. For example the Needleman Wunsch algorithm (Needleman and Wunsch 1970, J. Mol. Biol. 48:443-453) for global alignment, or the Smith Waterman algorithm (Smith and Waterman 1981, J. Mol. Biol. 147:195-197) for local alignment may be used, e.g. using the default parameters (Smith Waterman uses BLOSUM 62 scoring matrix with a Gap opening penalty of 10 and a Gap extension penalty of 1). A preferred algorithm is described by Dufresne et al. in Nature Biotechnology in 2002 (vol. 20, pp. 1269-71) and is used in the software GenePAST (Genome Quest Life Sciences, Inc. Boston, MA). The GenePAST "percent identity" algorithm finds the best fit between the query sequence and the subject sequence, and expresses the alignment as an exact percentage. GenePAST makes no alignment scoring adjustments based on considerations of biological relevance between query and subject sequences. Identity between two sequences is calculated across the entire length of both sequences and is expressed as a percentage of the reference sequence (e.g. SEQ ID NO: 16 of the present invention).

As used herein the term "recombinant" means artificial or synthetic. In an embodiment, a "recombinant protein" refers to a protein that has been made using recombinant nucleotide sequences (nucleotide sequences introduced into a host cell). In an embodiment, the nucleotide sequence that encodes a "recombinant protein" is heterologous to the host cell.

As used herein the terms "isolated" or "purified" mean a protein, conjugate (e.g. bioconjugate), polynucleotide, or vector in a form not found in nature. This includes, for example, a a protein, conjugate (e.g. bioconjugate), polynucleotide, or vector having been separated from host cell or organism (including crude extracts) or otherwise removed from its natural environment. In an embodiments, an isolated or purified protein is a protein essentially free from all other polypeptides with which the protein is innately associated (or innately in contact with).

As used herein, the term "subject" refers to an animal, in particular a mammal such as a primate (e.g. human).

As used herein, the term "effective amount," in the context of administering a therapy (e.g. an immunogenic composition or vaccine of the invention) to a subject refers to the amount of a therapy which has a prophylactic and/or therapeutic effect(s). In an embodiments, an "effective amount" refers to the amount of a therapy which is sufficient to achieve one, two, three, four, or more of the following effects: (i) reduce or ameliorate the severity of a bacterial infection or symptom associated therewith; (ii) reduce the duration of a bacterial infection or symptom associated therewith; (iii) prevent the progression of a bacterial infection or symptom associated therewith; (iv) cause regression of a bacterial infection or symptom associated therewith; (v) prevent the development or onset of a bacterial infection, or symptom associated therewith; (vi) prevent the recurrence of a bacterial infection or symptom associated therewith; (vii) reduce organ failure associated with a bacterial infection; (viii) reduce hospitalization of a subject having a bacterial infection; (ix) reduce hospitalization length of a subject having a bacterial infection; (x) increase the survival of a subject with a bacterial infection; (xi) eliminate a bacterial infection in a subject; (xii) inhibit or reduce a bacterial replication in a subject; and/or (xiii) enhance or improve the prophylactic or therapeutic effect(s) of another therapy.

As used herein, a "multivalent immunogenic composition" or "multivalent vaccine" is an immunogenic composition/vaccine that comprises two or more different antigens. In a particular embodiment, the multivalent immunogenic composition/vaccine comprises two or more different serotypes or subserotypes of a particular pathogen (e.g. against two or more different subserotypes of *Klebsiella pneumoniae*).

The term "comprises" is open-ended and means "includes." Thus, unless the context requires otherwise, the word "comprises" or "has", and variations thereof (including "comprise" and "comprising" or "have" and "having", respectively), will be understood to imply the inclusion of a stated compound(s), molecule(s), composition(s), or steps, but not to the exclusion of any other compound(s), molecule(s), composition(s), or steps. The terms "comprising" and "having" when used as a transition phrase herein are open-ended whereas the term "consisting of" when used as a transition phrase herein is closed (i.e., limited to that which is listed and nothing more). In an embodiments and for readability, the word "is" may be used as a substitute for "consists of" or "consisting of". The abbreviation, "e.g." is derived from the Latin exempli gratia, and is used herein to indicate a non-limiting example. Thus, the abbreviation "e.g." is synonymous with the term "for example".

Immunogenic Compositions

The present invention provides an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate. Each of the *Klebsiella pneumoniae* O1v1, O2a, O2afg and O3b O-antigen polysaccharides are individually conjugated to a carrier protein (e.g. a detoxified Exotoxin A of *Pseudomonas aeruginosa* (EPA)).

The present invention provides a multivalent immunogenic composition against subserotypes O1v1, O2a, O2afg and O3b of *Klebsiella pneumoniae*. In an embodiment, the immunogenic composition comprises O-antigens from subserotypes O1v1, O2a, O2afg and O3b of *Klebsiella pneumoniae*. Such O-antigens may be in the form of a polysaccharide conjugate where the O-antigen polysaccharide is conjugated (i.e. covalently linked) to a carrier protein. Polysaccharides comprise 2 or more monosaccharides, typically greater than 10 monosaccharides.

O1-antigens and O2-antigens are built of homopolymers of galactose, i.e. galactans. These O-antigen polysaccharides are part of a family of related structures, which share a D-galactan I backbone (gal-I). D-galactan I has the repeating unit structure: [→3)-$\beta$-D-Galf-(1→3)-$\alpha$-D-Galp-(1→ (FIG. 1 of Hsieh et al. 2014 Front. Microbiol. 5:608, doi: 10.3389/fmich.2014.00608) and is the core element of serotype O2a. The O-antigen polysaccharide of serotype O2afg differs from other known O-antigen polysaccharides in *Klebsiella* spp. in that each of the main-chain Galp residues in the O2afg O-antigen polysaccharide is substituted with an $\alpha$-(1→4)-linked D-Galp residue, to form a trisaccharide repeating unit, D-galactan III (gal-III) (Kelly et al. (1995) Innate Immun. 2, 131-140). D-galactan III has the repeating unit structure: →3)-β-D-Galf (1→3)-[α-D-Galp-(1→4)]-α-D-Galp-(1→ (Stojkovic et al. 2017 Front. Microbiol. 8:684, doi: 10.3389/fmicb.2017.00684). Kelly et al. J. Biol. Chem. (2019) 294(28) 10863-10876 further describes the repeat-unit structures of O1 and O2 serogroup antigens.

In the case of O1, gal-I is capped by repeats of an antigenically different galactose disaccharide termed D-galactan-II (gal-II). D-galactan II has the repeating unit structure: [→3)-α-D-Galp-(1→3)-β-D-Galp-(1→ (FIG. 1 of Hsieh et al. 2014 Front. Microbiol. 5:608, doi: 10.3389/fmicb.2014.00608.) The O-antigen O3b of *Klebsiella pneumoniae* is described in Guachalla et al. (2017) Scientific Reports 7:6635, 1-13. The O3b O-antigen, has a tri-mannose form, whereas O3 has a penta-mannose form and O3a has a tetra-mannose form. These subtypes have been shown by Guachalla et al. (2017) to be antigenically different.

In an immunogenic composition of the invention the *Klebsiella pneumoniae* O1v1 O-antigen polysaccharide may have the structure -(D-galactan II)n-(D-galactan I)n-GlcNAc:

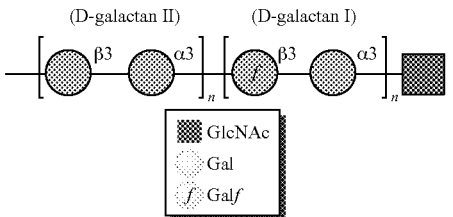

(D-galactan II)    (D-galactan I)

wherein n is the number of repeat units. This structure can also be written as: [→3)-β-D-Galp-(1→3)-α-D-Galp-(1→]n-[→3)-β-D-Galf-(1→3)-α-D-Galp-(1→]n→3)-D-GlcNAc. The number of repeat units for D-galactan II may be different from the number of repeat units for D-galactan I. Optionally the number of repeat units (n) ranges from 4 to 8 or 5 to 7, for example 6 for D-galactan II and the number of repeat units (n) ranges from 2 to 10, 3 to 6, for example 4 for D-galactan I. For example, the number of repeat units (n) may range from 5 to 7 for D-galactan II and the number of repeat units (n) may range from 3 to 5 for D-galactan I. Optionally the ratio of D-galactan II:D-galactan I ranges between 2:1 to 1:50 or 2:1 to 1:2 (e.g. between 1.5:1 to 2:1).

In an immunogenic composition of the invention the *Klebsiella pneumoniae* O2a O-antigen polysaccharide may have the structure -(D-galactan I)n-GlcNAc:

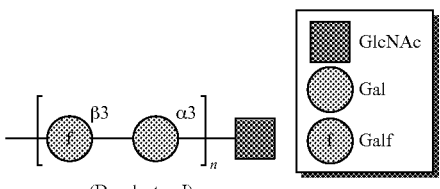

(D-galactan I)

wherein n is the number of repeat units. This structure can also be written as: [→3)-β-D-Galf (1→3)-α-D-Galp-(1→]n→3)-D-GlcNAc. Optionally the number of repeat units (n) ranges from 10 to 30, e.g. from 15 to 30.

An an immunogenic composition of the invention the *Klebsiella pneumoniae* O2afg O-antigen polysaccharide may have the structure -(D-galactan III)n-GlcNAc:

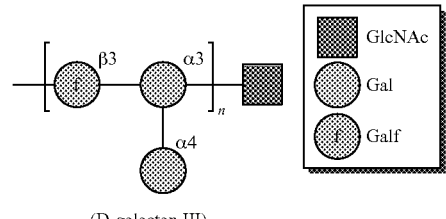

(D-galactan III)

wherein n is the number of repeat units. This structure can also be written as: [→3)-β-D-Galf-(1→3)-[α-D-Galp-(1→4)]-α-D-Galp-(1→]n→3)-D-GlcNAc. Optionally the number of repeat units (n) ranges from 5 to 25 (e.g. from 5 to 15). Optionally the degree of branching ranges from 90-100%.

In an immunogenic composition of the invention the *Klebsiella pneumoniae* O3b O-antigen polysaccharide may have the structure Me-P-3(Man-α2-Man-α3-Man-α3)n-Man-α3-Man-α3-GlcNAc:

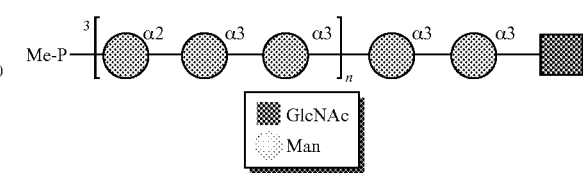

wherein n is the number of repeat units. This structure can also be written as: Me-P-[→3)-α-D-Man(1→2)-α-D-Man(1→3)-α-D-Man(1→]n→3)-α-D-Man(1→3)-α-D-Man(1→3)-D-GlcNAc. Optionally the number of repeat units (n) ranges from 5 to 25 (e.g. from 10 to 20).

An immunogenic composition of the invention may also comprise a pharmaceutically acceptable excipient and/or carrier. Pharmaceutically acceptable excipients and carriers are described, for example, in Remington's Pharmaceutical Sciences, by E. W. Martin, Mack Publishing Co. Easton, PA, 5th Edition (1975). Pharmaceutically acceptable excipients can include a buffer, such as a phosphate buffer (e.g. sodium phosphate). Pharmaceutically acceptable excipients can include a salt, for example sodium chloride. Pharmaceutically acceptable excipients can include a solubilizing/stabilizing agent, for example, polysorbate (e.g. TWEEN 80). Pharmaceutically acceptable excipients can include a preservative, for example 2-phenoxyethanol or thiomersal. Pharmaceutically acceptable excipients can include a carrier such as water or saline.

The present invention provides an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are individually conjugated to a carrier protein (e.g. a detoxified Exotoxin A of *Pseudomonas aeruginosa* (EPA)).

Also provided is a process for making an immunogenic composition of the invention comprising combining a *Kleb-*

*siella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, and optionally a pharmaceutically acceptable excipient and/or carrier.

Carrier Proteins

The present invention provides an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate.

Any carrier protein suitable for use in the production of conjugate vaccines (e.g. bioconjugates for use in vaccines) can be used herein. For example, a nucleotide sequence encoding the carrier protein can be introduced into a host provided herein for the production of a bioconjugate, e.g. a bioconjugate comprising a carrier protein linked to a *Klebsiella pneumoniae* O-antigen. Exemplary carrier proteins include, without limitation, detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, *Pseudomonas* PcrV protein, and *C. jejuni* natural glycoproteins.

In an embodiments, the carrier protein used in the generation of the bioconjugates described herein are modified, e.g. modified in such a way that the carrier protein is less toxic and/or more susceptible to glycosylation. In a specific embodiment, the carrier proteins used in the generation of the bioconjugates described herein are modified such that the number of glycosylation sites in the carrier proteins is increased in a manner that allows for lower concentrations of the protein to be administered, e.g. in an immunogenic composition, in its bioconjugate form.

The carrier protein may be modified to include 1, 2, 3, 4, 5, 6, 7, 8, 9, 10, or more glycosylation sites than would normally be associated with the carrier protein (e.g. relative to the number of glycosylation sites associated with the carrier protein in its native/natural, e.g. "wild-type" state). In specific embodiments, introduction of glycosylation sites is accomplished by insertion of glycosylation consensus sequences (as described in WO 2006/119987) anywhere in the primary structure of the protein. The carrier protein used herein may comprise a D/E-X-N-Z-S/T (SEQ ID NO: 1) consensus sequence, wherein X and Z are independently any amino acid except proline. Accordingly, the present invention provides an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are individually conjugated to a carrier protein comprising an inserted consensus sequence D/E-X-N-Z-S/T (SEQ ID NO: 1) wherein X and Z may be any natural amino acid except proline.

In certain embodiments, the classical 5 amino acid glycosylation consensus sequence (D/E-X-N-Z-S/T (SEQ ID NO: 1)) may be extended by lysine residues for more efficient glycosylation (e.g. K-D/E-X-N-Z-S/T-K (SEQ ID NO: 2)), wherein X and Z are independently any amino acid except proline (preferably wherein X is Q (glutamine), Z is A (alanine). In an embodiment of the invention, one or more amino acids (e.g. 1-7 amino acids, e.g. one amino acid) of the carrier protein amino acid sequence is/are substituted by a five amino acid D/E-X-N-Z-S/T (SEQ ID NO: 1) or by a seven amino acid K-D/E-X-N-Z-S/T-K (SEQ ID NO: 2) (e.g. K-D-Q-N-A-T-K (SEQ ID NO: 3) also referred to as "KDQNATK") consensus sequence, wherein X and Z are independently any amino acid except proline (preferably wherein X is Q (glutamine), Z is A (alanine)). For example, a single amino acid in the carrier protein amino acid sequence may be substituted (i.e. replaced) with a D/E-X-N-Z-S/T (SEQ ID NO: 1) or K-D/E-X-N-Z-S/T-K (SEQ ID NO: 2) (e.g. K-D-Q-N-A-T-K (SEQ ID NO: 3)) consensus sequence. Alternatively, 2, 3, 4, 5, 6 or 7 amino acids within the carrier protein amino acid sequence may be substituted (i.e. replaced) with a D/E-X-N-Z-S/T (SEQ ID NO: 1) or K-D/E-X-N-Z-S/T-K (SEQ ID NO: 2) consensus sequence, wherein X and Z are independently any amino acid except proline (preferably wherein X is Q (glutamine), Z is A (alanine)) (e.g. K-D-Q-N-A-T-K (SEQ ID NO: 3). The classical 5 amino acid glycosylation consensus sequence (D/E-X-N-Z-S/T (SEQ ID NO: 1)) may also be extended by 1-5 other amino acid residues either side of the consensus sequence for more efficient glycosylation J-D/E-X-N-Z-S/T-U (SEQ ID NO: 4) wherein J and U are independently 1 to 5 naturally occurring amino acid residues (preferably J and U are independently 1 to 5 amino acid residues independently selected from glycine and/or serine, e.g. G-S-G-G-G-D/E-X-N-Z-S/T-G-S-G-G (SEQ ID NO: 5)). Thus, the carrier protein as used herein may comprise consensus sequence(s) selected from: D/E-X-N-Z-S/T (SEQ ID NO: 1), K-D/E-X-N-Z-S/T-K (SEQ ID NO: 2) and/or J-D/E-X-N-Z-S/T-U (SEQ ID NO: 4) wherein X and Z are independently any amino acid except proline (preferably wherein X is Q (glutamine), Z is A (alanine)) and wherein J and U are independently 1 to 5 naturally occurring amino acid residues (preferably J and U are independently 1 to 5 amino acid residues independently selected from glycine and/or serine). For example, the carrier protein as used herein may comprise 3-7 consensus sequence(s) selected from: D/E-X-N-Z-S/T (SEQ ID NO: 1), K-D/E-X-N-Z-S/T-K (SEQ ID NO: 2) and/or J-D/E-X-N-Z-S/T-U (SEQ ID NO: 4) wherein X and Z are independently any amino acid except proline (preferably wherein X is Q (glutamine), Z is A (alanine)) and wherein J and U are independently 1 to 5 naturally occurring amino acid residues (preferably J and U are independently 1 to 5 amino acid residues independently selected from glycine and/or serine).

A combination of consensus sequences selected from: a five amino acid consensus sequence D/E-X-N-Z-S/T (SEQ ID NO: 1), a seven amino acid consensus sequence K-D/E-X-N-Z-S/T-K (SEQ ID NO: 2) and an extended consensus sequence (e.g. J-D/E-X-N-Z-S/T-U (SEQ ID NO: 4)) may be used. For example, a carrier protein may comprise 1, 2, 3, 4 or 5 consensus sequences selected from D/E-X-N-Z-S/T (SEQ ID NO: 1) and K-D/E-X-N-Z-S/T-K (SEQ ID NO: 2), wherein X and Z are independently any amino acid except proline (preferably wherein X is Q (glutamine), Z is A (alanine)), and the carrier protein may further comprise 1 or 2 extended consensus sequences J-D/E-X-N-Z-S/T-U (SEQ ID NO: 4) wherein J and U are independently 1 to 5 naturally occurring amino acid residues (preferably J and U are independently 1 to 5 amino acid residues independently selected from glycine and/or serine, e.g. G-S-G-G-G-D/E-X-N-Z-S/T-G-S-G-G (SEQ ID NO: 5)). Preferably, an extended consensus sequence, such as J-D/E-X-N-Z-S/T-U (SEQ ID NO: 4) or G-S-G-G-G-D/E-X-N-Z-S/T-G-S-G-G (SEQ ID NO: 5) is used where the consensus sequence is added next to the N-terminal or C-terminal amino acid of the EPA protein.

Thus, the present invention also provides an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are individually conjugated to a carrier protein comprising 3 to 7 consensus sequence(s) selected from: D/E-X-N-Z-S/T (SEQ ID NO: 1), K-D/E-X-N-Z-S/T-K (SEQ ID NO: 2) and/or J-D/E-X-N-Z-S/T-U (SEQ ID NO: 4), wherein X and Z are independently any amino acid except proline (preferably wherein X is Q (glutamine), Z is A (alanine)) (e.g. K-D-Q-N-A-T-K (SEQ ID NO: 3), and wherein J and U are independently 1 to 5 naturally occurring amino acid residues (preferably J and U are independently 1 to 5 amino acid residues independently selected from glycine and/or serine, e.g. G-S-G-G-G-D/E-X-N-Z-S/T-G-S-G-G (SEQ ID NO: 5)).

Introduction of such glycosylation sites can be accomplished by, e.g. adding new amino acids to the primary structure of the protein (i.e. the glycosylation sites are added, in full or in part), or by mutating existing amino acids in the protein in order to generate the glycosylation sites (i.e. amino acids are not added to the protein, but selected amino acids of the protein are mutated so as to form glycosylation sites). Those of skill in the art will recognize that the amino acid sequence of a protein can be readily modified using approaches known in the art, e.g. recombinant approaches that include modification of the nucleic acid sequence encoding the protein. In specific embodiments, glycosylation consensus sequences are introduced into specific regions of the carrier protein, e.g. surface structures of the protein, at the N or C termini of the protein, and/or in loops that are stabilized by disulfide bridges at the base of the protein.

In an embodiment, the carrier protein may be a detoxified Exotoxin A of *Pseudomonas aeruginosa* (EPA). Exotoxin A of *Pseudomonas aeruginosa* (also known as "EPA", or "ETA"), is a secreted bacterial toxin, a member of the ADP-ribosyltransferasetoxin family. An EPA protein useful in the invention can be produced by methods known in the art in view of the present disclosure, see for example Ihssen et al. (2010) Microbial Cell Factories 9:61, WO 2006/119987, WO 2009/104074 and WO2015124769A1. Exotoxin A from *Pseudomonas aeruginosa* strain PA103 was cloned and sequenced by Gray et al. (1984) Proc. Nati. Acad. Sci. USA Vol. 81, pp. 2645-2649. Comparison of the deduced $NH_2$-terminal amino acid sequence with that determined by sequence analysis of the secreted protein indicated that EPA was made as a 638 amino acid precursor from which a highly hydrophobic leader peptide of 25 amino acids is removed during the secretion process (see FIG. 1 of Gray et al. (1984)). SEQ ID NO: 16 provides the mature EPA amino acid sequence.

```
EPA amino acid sequence
                                                    SEQ ID NO: 16
AEEAFDLWNECAKACVLDLKDGVRSSRMSVDPAIADTNGQGVLHYSMVLEGGNDALKLAIDNALSITSDGLTIR

LEGGVEPNKPVRYSYTRQARGSWSLNWLVPIGHEKPSNIKVFIHELNAGNQLSHMSPIYTIEMGDELLAKLARDA

TFFVRAHESNEMQPTLAISHAGVSVVMAQAQPRREKRWSEWASGKVLCLLDPLDGVYNYLAQQRCNLDDTWE

GKIYRVLAGNPAKHDLDIKPTVISHRLHFPEGGSLAALTAHQACHLPLEAFTRHRQPRGWEQLEQCGYPVQRLV

ALYLAARLSWNQVDQVIRNALASPGSGGDLGEAIREQPEQARLALTLAAAESERFVRQGTGNDEAGAASADVVS

LTCPVAAGECAGPADSGDALLERNYPTGAEFLGDGGDVSFSTRGTQNWTVERLLQAHRQLEERGYVFVGYHGT

FLEAAQSIVFGGVRARSQDLDAIWRGFYIAGDPALAYGYAQDQEPDARGRIRNGALLRVYVPRWSLPGFYRTGL

TLAAPEAAGEVERLIGHPLPLRLDAITGPEEEGGRVTILGWPLAERTVVIPSAIPTDPRNVGGDLDPSSIPDKEQAI

SALPDYASQPGKPPREDLK

EPA sequence (amino acids 1 to 612 with numbering)
                                                    SEQ ID NO: 16
        10        20        30        40        50        60
AEEAFDLWNE CAKACVLDLK DGVRSSRMSV DPAIADTNGQ GVLHYSMVLE GGNDALKLAI 70        80        90       100       110       120
DNALSITSDG LTIRLEGGVE PNKPVRYSYT RqARGSWSLN WLVPIGHEKP SNIKVFIHEL 130       140       150       160       170       180
NAGNQLSHMS PIYTIEMGDE LLAKLARDAT FFVRAHESNE MQPTLAISHA GVSVVMAQAQ 190       200       210       220       230       240
PRREKRWSEW ASGKVLCLLD PLDGVYNYLA QQRCNLDDTW EGKIYRVLAG NPAKHDLDIK 250       260       270       280       290       300
PTVISHRLHF PEGGSLAALT AHQACHLPLE AFTRHRQPRG WEQLEQCGYP VQRLVALYLA 310 3     320       330       340       350       360
ARLSWNQVDQ VIRNALASPG SGGDLGEAIR EQPEQARLAL TLAAAESERF VRQGTGNDEA
```

```
-continued
        370        380        390        400        410        420
GAASADVVSL TCPVAAGECA GPADSGDALL ERNYPTGAEF LGDGGDVSFS TRGTQNWTVE 430        440        450        460        470        480
RLLQAHRQLE ERGYVFVGYH GTFLEAAQSI VEGGVRARSQ DLDAIWRGFY IAGDPALAYG 490        500        510        520        530        540
YAQDQEPDAR GRIRNGALLR VYVPRWSLPG FYRTGLTLAA PEAAGEVERL IGHPLPLRLD 550        560        570        580        590        600
AITGPEEEGG RVTILGWPLA ERTVVIPSAI PTDPRNVGGD LDPSSIPDKE QAISALPDYA

610
SQPGKPPRED LK
```

The numbering of the amino acid residues as specified herein, refers to the amino acid position in SEQ ID NO: 16 (or where an amino acid sequence is at least 80%, 85%, 90%, 92%, 95%, 96%, 97%, 98% or 99% identical to SEQ ID NO: 16 to an equivalent position to that of SEQ ID NO: 16 if this sequence was lined up with an amino acid sequence of SEQ ID NO: 16 in order to maximise the sequence identity between the two sequences using Needleman Wunsch algorithm).

Because EPA is a toxin, it needs to be detoxified (i.e. rendered non-toxic to a mammal, e.g. human, when provided at a dosage suitable for protection) before it can be administered in vivo. A detoxified EPA protein may be genetically detoxified (i.e. by mutation). The genetically detoxified sequences may remove undesirable activities such as ADP-ribosyltransferase activity, in order to reduce the toxicity, whilst retaining the ability to induce anti-EPA protective and/or neutralizing antibodies following administration to a human. The genetically detoxified sequences may maintain their immunogenic epitopes. A detoxified EPA protein may be genetically detoxified by one or more point mutations. For example, detoxification can be achieved by mutating and deleting catalytically essential residues, such as substitution of leucine 552 to valine (L552V) and by deletion of glutamic acid-553 (ΔE553), according to Lukac et al. (1988), Infect Immun, 56:3095-3098, and Ho et al. (2006), Hum Vaccin, 2:89-98. Detoxification can be achieved by mutating/deleting the catalytically essential residues L552V ΔE553 using quick change mutagenesis (Stratagene) and phosphorylated oligonucleotides 5'-GAA-GGCGGGCGCGTGACCA TTCTCGGC (SEQ ID NO: 40) and 5'-GCCGAGAATGGTCACGCGCCCGCCTTC (SEQ ID NO: 41) resulting in construct pGVXN70. Accordingly, the detoxified EPA protein as used herein may have an amino acid sequence comprising (or consisting) of an amino acid sequence at least 80%, 85%, 90%, 92%, 95%, 96%, 97%, 98% or 99% identical to SEQ ID NO: 16 and having a substitution of leucine 552 to valine (L552V) and deletion of glutamine 553 (ΔE553) with reference to the amino acid sequence of SEQ ID NO: 16 (or an equivalent position in an amino acid sequence at least 80%, 85%, 90%, 92%, 95%, 96%, 97%, 98% or 99% identical to SEQ ID NO: 16).

Detoxification can be measured by determining the inhibition of ADP-ribosyltransferase and cytotoxic activity according to the methodology described in Lukac et al. (1988), Infect Immun, 56:3095-3098, and references cited therein, namely Douglas et al (1987) J. Bacteriol 169:4962-4966 and Douglas et al (1987). A detoxified EPA has ADP-ribosyltransferase and cytotoxic activities lower than wild-type EPA, suitably the same as or less than that of the modified EPA described in Lukac et al (1988) i.e. ΔE553 EPA (EPA having deletion of glutamic acid-533).

Thus the present invention provides an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are individually conjugated to a detoxified Exotoxin A of *Pseudomonas aeruginosa* (EPA), e.g. a detoxified Exotoxin A of *Pseudomonas aeruginosa* (EPA) having an amino acid sequence comprising (or consisting) of an amino acid sequence at least 80%, 85%, 90%, 92%, 95%, 96%, 97%, 98% or 99% identical to SEQ ID NO: 16 and having a substitution of leucine 552 to valine (L552V) and deletion of glutamine 553 (ΔE553).

The detoxified Exotoxin A of *Pseudomonas aeruginosa* (EPA) as used herein may be further modified in that the amino acid sequence comprises one (or more) consensus sequence(s) selected from: D/E-X-N-Z-S/T (SEQ ID NO: 1), K-D/E-X-N-Z-S/T-K (SEQ ID NO: 2) or J-D/E-X-N-Z-S/T-U (SEQ ID NO: 4) wherein X is Q (glutamine), Z is A (alanine), J and U are independently 1 to 5 amino acid residues independently selected from glycine and/or serine, as described above. The one (or more) consensus sequences may each be added next to, or substituted for one or more amino acids selected from specific amino acid residues within the EPA protein (consensus sequence sites). For example, the detoxified Exotoxin A of *Pseudomonas aeruginosa* (EPA) may comprise 3 to 7 inserted consensus sequences D/E-X-N-Z-S/T, wherein X and Z may be any natural amino acid except proline. Thus the present invention provides an immunogenic composition comprising a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are individually conjugated to a detoxified Exotoxin A of *Pseudomonas aeruginosa* (EPA) comprises 3 to 7 inserted consensus sequences D/E-X-N-Z-S/T, wherein X and Z may be any natural amino acid except proline. For example, a detoxified Exotoxin A of *Pseudomonas aeruginosa* (EPA) having an amino acid sequence comprising (or consisting) of an amino acid sequence at least 80%, 85%, 90%, 92%, 95%, 96%, 97%, 98% or 99% identical to SEQ ID NO: 16 and having a substitution of leucine 552 to valine (L552V) and deletion of glutamine 553 (ΔE553) and comprising 3 to 7 inserted consensus sequences D/E-X-N-Z-S/T, wherein X and Z may be any natural amino acid except proline. Thus, the present invention also provides an immunogenic composition comprising a *Klebsiella*

*pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are individually conjugated to a detoxified Exotoxin A of *Pseudomonas aeruginosa* (EPA) carrier protein having an amino acid sequence comprising (or consisting) of an amino acid sequence at least 80%, 85%, 90%, 92%, 95%, 96%, 97%, 98% or 99% identical to SEQ ID NO: 16 modified in having a substitution of leucine 552 to valine (L552V) and deletion of glutamine 553 (ΔE553) and comprising 3 to 7 consensus sequence(s) selected from: D/E-X-N-Z-S/T (SEQ ID NO: 1), K-D/E-X-N-Z-S/T-K (SEQ ID NO: 2) and/or J-D/E-X-N-Z-S/T-U (SEQ ID NO: 4), wherein X and Z are independently any amino acid except proline (preferably wherein X is Q (glutamine), Z is A (alanine)) (e.g. K-D-Q-N-A-T-K (SEQ ID NO: 3), and wherein J and U are independently 1 to 5 naturally occurring amino acid residues (preferably J and U are independently 1 to 5 amino acid residues independently selected from glycine and/or serine, e.g. G-S-G-G-G-D/E-X-N-Z-S/T-G-S-G-G (SEQ ID NO: 5)).

The detoxified Exotoxin A of *Pseudomonas aeruginosa* (EPA) as used herein may contain four consensus sequences. The detoxified Exotoxin A of *Pseudomonas aeruginosa* (EPA) as used herein may have an amino acid sequence of SEQ ID NO: 16 or an amino acid sequence at least 80%, 85%, 90%, 92%, 95%, 96%, 97%, 98% or 99% identical to SEQ ID NO: 16 modified in that the amino acid sequence has a substitution of leucine 552 to valine (L552V), a deletion of glutamine 553 (ΔE553) and comprises four consensus sequences, e.g. wherein four consensus sequences are added next to or substituted for four independently selected amino acid residues of SEQ ID NO: 16 or an amino acid sequence at least 80%, 85%, 90%, 92%, 95%, 96%, 97%, 98% or 99% identical to SEQ ID NO: 16. The detoxified Exotoxin A of *Pseudomonas aeruginosa* (EPA) as used herein may contain four consensus sequences, optionally substituted for amino acid residues Y208, R274, A519 and added next to the N-terminal amino acid of SEQ ID NO: 16 or an amino acid sequence at least 80%, 85%, 90%, 92%, 95%, 96%, 97%, 98% or 99% identical to SEQ ID NO: 16. Preferably, the detoxified Exotoxin A of *Pseudomonas aeruginosa* (EPA) as used herein may comprise (or consist of) an amino acid sequence which is at least 95%, 96%, 97%, 98%, 99% or 100% identical to SEQ ID NO: 17.

In an embodiment, the carrier protein as used herein further comprises a signal sequence which is capable of directing the carrier protein to the periplasm of a host cell (e.g. bacterium). Signal sequences, including periplasmic signal sequences, are usually removed during translocation of the protein into, for example, the periplasm by signal peptidases (i.e., a mature protein is a protein from which at least the signal sequence has been removed). The signal sequence may be from *E. coli* flagellin (FlgI) [MIKFLSALILLLVTTAAQA (SEQ ID NO: 6)], *E. coli* outer membrane porin A (OmpA) [MKKTAIAIAVALAGFATVAQA (SEQ ID NO: 7)], *E. coli* maltose binding protein (MalE) [MKIKTGARILALSALTTMMFSASALA (SEQ ID NO: 8)], *Erwinia carotovorans* pectate lyase (PelB) [MKYLLPTAAAGLLLLAAQPAMA (SEQ ID NO: 9)], heat labile *E. coli* enterotoxin LTIIb [MSFKKIIKAFVIMAALVSVQAHA (SEQ ID NO: 10)], *Bacillus subtilis* endoxylanase XynA [MFKFKKKFLVGLTAAFMSISMFSATASA (SEQ ID NO: 11)], *E. coli* DsbA [MK- KIWLALAGLVLAFSASA (SEQ ID NO: 12)], TolB [MKQALRVAFGFLILWASVLHA (SEQ ID NO: 13)] or SipA [MKMNKKVLLTSTMAASLLSVASVQAS (SEQ ID NO: 14)]. In a specific embodiment, the signal sequence is from *E. coli* DsbA [MKKIWLALAGLVLAFSASA (SEQ ID NO: 12)]. Thus, the carrier protein may further comprise a signal sequence which is capable of directing the carrier protein to the periplasm of a host cell (e.g. bacterium), optionally said signal sequence being DsbA (SEQ ID NO: 12). A signal peptide of the protein DsbA from *E. coli* can be genetically fused to the N-terminus of the mature carrier protein sequence. For example, a plasmid derived from pEC415 [Schulz, H., Hennecke, H., and Thony-Meyer, L., Science, 281, 1197-1200, 1998] containing the DsbA signal peptide code followed by a RNase sequence can be digested (NdeI to EcoRI) to keep the DsbA signal and remove the RNase insert. EPA is then amplified using PCR (forward oligo 5'-AAGCTAGCGCCGCCGAGGAAGCCTTCGACC (SEQ. ID NO. 19) and reverse oligo 5'-AAGAA TTCTCAGTGGTGGTGGTGGTGGTGCTTCAGGTCCTCGCGCGGCGG (SEQ. ID NO. 20)) and digested NheI/ EcoRI and ligated to replace the RNase sequence removed previously. The resulting construct (pGVXN69) encodes a protein product with an DsbA signal peptide, the mature carrier sequence and a hexa-histag. For example, a detoxified Exotoxin A of *Pseudomonas aeruginosa* (EPA) with a DsbA signal sequence having an amino acid sequence comprising (or consisting of) an amino acid sequence which is at least 95%, 96%, 97%, 98%, 99% or 100% identical to SEQ ID NO: 18.

In specific embodiments, the carrier protein expressed by host cells of the invention are expressed from a nucleotide sequence that has been integrated into the genome of the host cell. That is, a nucleotide sequence encoding the carrier protein has been integrated into the host cell genome. Alternatively, the carrier protein expressed in the host cell of the invention is expressed from a plasmid that has been introduced into the host cell.

Conjugates

The present invention also provides a conjugate (e.g. bioconjugate) comprising a *Klebsiella pneumoniae* O-antigen polysaccharide selected from O1v1, O2a, O2afg or O3b conjugated to a carrier protein, e.g. wherein the carrier protein is a detoxified Exotoxin A of *Pseudomonas aeruginosa* (EPA).

In an embodiment, the conjugate (e.g. bioconjugate) comprises (or consists of) a *Klebsiella pneumoniae* O-antigen polysaccharide selected from O1v1, O2a, O2afg or O3b covalently linked (either directly or through a linker) to a carrier protein, e.g. a detoxified Exotoxin A of *Pseudomonas aeruginosa* (EPA). In an embodiment, the *Klebsiella pneumoniae* O-antigen polysaccharide selected from O1v1, O2a, O2afg or O3b is directly linked to the carrier protein, e.g. a detoxified Exotoxin A of *Pseudomonas aeruginosa* (EPA). In an embodiment, the *Klebsiella pneumoniae* O-antigen polysaccharide selected from O1v1, O2a, O2afg or O3b is directly linked to an amino acid residue of the carrier protein, e.g. a detoxified Exotoxin A of *Pseudomonas aeruginosa* (EPA).

In an embodiment, the *Klebsiella pneumoniae* O-antigen polysaccharide selected from O1v1, O2a, O2afg or O3b is covalently linked to the carrier protein, e.g. a detoxified Exotoxin A of *Pseudomonas aeruginosa* (EPA) through a chemical linkage obtainable using a chemical conjugation method (i.e. the conjugate is produced by chemical conjugation). The chemical conjugation method may be selected from the group consisting of carbodiimide chemistry, reductive animation, cyanylation chemistry (for example CDAP chemistry), maleimide chemistry, hydrazide chemistry, ester chemistry, and N-hydroysuccinimide chemistry. Conjugates can be prepared by direct reductive amination methods as described in, US200710184072 (Hausdorff) U.S. Pat. No. 4,365,170 (Jennings) and U.S. Pat. No. 4,673,574 (Anderson). Other methods are described in EP-O-161-188, EP-208375 and EP-O-477508. The conjugation method may alternatively rely on activation of the saccharide with 1-cyano-4-dimethylamino pyridinium tetrafluoroborate (CDAP) to form a cyanate ester. Such conjugates are described in PCT published application WO 93/15760 Uniformed Services University and WO 95/08348 and WO 96/29094. See also Chu C. et al. Infect. Immunity, 1983 245 256.

In general the following types of chemical groups on carrier protein, e.g. a detoxified Exotoxin A of *Pseudomonas aeruginosa* (EPA), can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments such as: periodate, acid hydrolysis, hydrogen peroxide, etc.

Conjugates can be purified by any method known in the art for purification of a protein, for example, by chromatography (e.g. ion exchange, anionic exchange, affinity, and sizing column chromatography), centrifugation, differential solubility, or by any other standard technique for the purification of proteins. See, e.g., Saraswat et al., 2013, Biomed. Res. Int. ID0312709 (p. 1-18); see also the methods described in WO 2009/104074. The actual conditions used to purify a particular conjugate will depend, in past, on the synthesis strategy (e.g., synthetic production vs. recombinant production) and on factors such as net charge, hydrophobicity, and/or hydrophilicity of the bioconjugate.

In an embodiment, the amino acid residue on the carrier protein, e.g. a detoxified Exotoxin A of *Pseudomonas aeruginosa* (EPA), to which the antigen is linked is selected from the group consisting of: Ala, Arg, Asp, Cys, Gly, Glu, Gln, His, Ile, Leu, Lys, Met, Phe, Pro, Ser, Thr, Trp, Tyr, and Val. Optionally, the amino acid is: an amino acid containing a terminal amine group, a lysine, an arginine, a glutaminic acid, an aspartic acid, a cysteine, a tyrosine, a histidine or a tryptophan. In an embodiment, the amino acid residue on the carrier protein, e.g. a detoxified Exotoxin A of *Pseudomonas aeruginosa* (EPA), to which the antigen is linked is not an asparagine residue and in this case, the conjugate is typically produced by chemical conjugation. Alternatively, the antigen is linked to an amino acid on the carrier protein, e.g. a detoxified Exotoxin A of *Pseudomonas aeruginosa* (EPA), selected from asparagine, aspartic acid, glutamic acid, lysine, cysteine, tyrosine, histidine, arginine or tryptophan (e.g. asparagine), and in the case of asparagine the conjugate may be a bioconjugate (for example an enzymatic conjugation using a oligosaccharyltransferase such as PglB). In an embodiment, the amino acid residue on the carrier protein, e.g. a detoxified Exotoxin A of *Pseudomonas aeruginosa* (EPA), to which the antigen is linked is an asparagine residue. Preferably, the amino acid residue on the modified EPA protein to which the antigen is linked is part of the consensus sequence, e.g. the asparagine in D/E-X-N-Z-S/T (SEQ ID NO: 1), K-D/E-X-N-Z-S/T-K (SEQ ID NO: 2) or J-D/E-X-N-Z-S/T-U (SEQ ID NO: 4) consensus sequence.

The conjugate of the invention may be a conjugate of a a *Klebsiella pneumoniae* O-antigen polysaccharide selected from O1v1, O2a, O2afg or O3b (e.g. chemical conjugate or bioconjugate). The conjugate of the invention may be a conjugate of an isolated recombinant carrier protein, e.g. a recombinant detoxified Exotoxin A of *Pseudomonas aeruginosa* (EPA), and a recombinant antigen, e.g. recombinant *Klebsiella pneumoniae* O-antigen polysaccharide selected from O1v1, O2a, O2afg or O3b (i.e. bioconjugate).

The present invention provides a conjugate (e.g. bioconjugate) wherein the *Klebsiella pneumoniae* O1v1 O-antigen polysaccharide has the structure -(D-galactan II)n-(D-galactan I)n-GlcNAc:

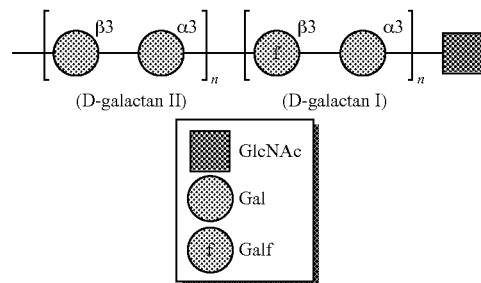

(D-galactan II)          (D-galactan I)

GlcNAc
Gal
Galf wherein n is the number of repeat units. This structure can also be written as: [→3)-β-D-Galp-(1→3)-α-D-Galp-(1→]n-[→3)-β-D-Galf-(1→3)-α-D-Galp-(1→]n→3)-D-GlcNAc. The number of repeat units for D-galactan II may be different from the number of repeat units for D-galactan I. Optionally the number of repeat units (n) ranges from 4 to 8, 5 to 7, for example 6 for D-galactan II and the number of repeat units (n) ranges from 2 to 10, 3 to 7, for example 4 for D-galactan I. For example, the number of repeat units (n) may range from 5 to 7 for D-galactan II and the number of repeat units (n) may range from 3 to 5 for D-galactan I. Optionally the ratio of D-galactan II:D-galactan I ranges between 2:1 to 1:50 or 2:1 to 1:2 (e.g. between 1.5:1 to 2:1).

The present invention provides a conjugate (e.g. bioconjugate) wherein the *Klebsiella pneumoniae* O2a O-antigen polysaccharide has the structure -(D-galactan I)n-GlcNAc:

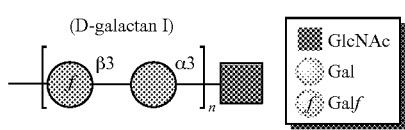

(D-galactan I)

wherein n is the number of repeat units. This structure can also be written as: [→3)-β-D-Galf-(1→3)-α-D-Galp-(1→]n→3)-D-GlcNAc. Optionally the number of repeat units (n) ranges from 10 to 30, e.g. from 15 to 30.

The present invention provides a conjugate (e.g. bioconjugate) wherein the *Klebsiella pneumoniae* O2afg O-antigen polysaccharide has the structure -(D-galactan III)n-GlcNAc:

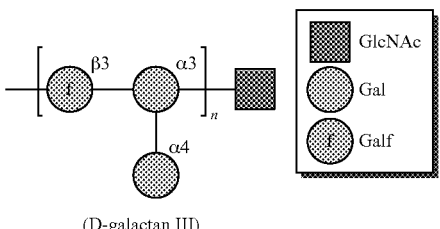

(D-galactan III)

wherein n is the number of repeat units. This structure can also be written as: [→3)-β-D-Galf-(1→3)-[α-D-Galp-(1→4)]-α-D-Galp-(1→]n→3)-D-GlcNAc. Optionally the number of repeat units (n) ranges from 5 to 25 (e.g. from 5 to 15). Optionally the degree of branching ranges from 90-100%.

The present invention provides a conjugate (e.g. bioconjugate) wherein the *Klebsiella pneumoniae* O3b O-antigen polysaccharide has the structure Me-P-3(Man-α2-Man-α3-Man-α3)n-Man-α3-Man-α3-GlcNAc:

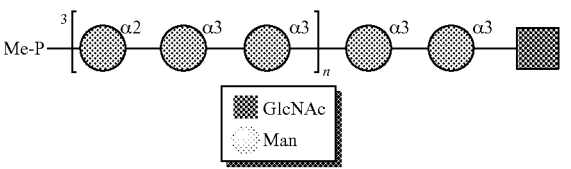

wherein n is the number of repeat units. This structure can also be written as: Me-P-[→3)-α-D-Man(1→2)-α-D-Man(1→3)-α-D-Man (1→]n→3)-α-D-Man(1→3)-α-D-Man(1→3)-D-GlcNAc. Optionally the number of repeat units (n) ranges from 5 to 25 (e.g. from 10 to 20).

The conjugates (e.g. bioconjugate), of the invention are particularly suited for inclusion in immunogenic compositions and vaccines. The present invention also provides an immunogenic composition comprising a conjugate (e.g. bioconjugate) of the invention, and optionally a pharmaceutically acceptable excipient and/or carrier.

Host Cell

The present invention provides a host cell comprising nucleotide sequences comprising polysaccharide synthesis genes for producing a *Klebsiella pneumoniae* O-antigen polysaccharide selected from O1v1, O2a, O2afg and O3b and a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aerugi-*

*nosa* (EPA) comprising an inserted consensus sequence D/E-X-N-Z-S/T wherein X and Z may be any natural amino acid except proline). Thus, the present invention provides a host cell comprising: i) nucleotide sequences comprising polysaccharide synthesis genes for producing a *Klebsiella pneumoniae* O-antigen polysaccharide selected from O1v1, O2a, O2afg and O3b, optionally integrated into the host cell genome; (ii) a nucleotide sequence encoding a heterologous oligosaccharyl transferase, optionally within a plasmid; (iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and optionally (iv) a nucleotide sequence encoding an ABC transporter, optionally *K. pneumoniae* genes wzm and wzt, optionally integrated into the host cell genome.

The present invention also provides a host cell comprising:

i) nucleotide sequences comprising polysaccharide synthesis genes for producing a *Klebsiella pneumoniae* O-antigen polysaccharide selected from O1v1, O2a, O2afg and O3b, optionally integrated into the host cell genome;

ii) a nucleotide sequence encoding a heterologous oligosaccharyl transferase, optionally within a plasmid;

iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and iv) a nucleotide sequence encoding an ABC transporter, optionally *K. pneumoniae* genes wzm and wzt, optionally integrated into the host cell genome.

Disclosures of methods for making such host cells which are capable of producing bioconjugates are found in WO 06/119987, WO 09/104074, WO 11/62615, WO 11/138361, WO 14/57109, WO14/72405 and WO16/20499.

Host cells that can be used to produce the bioconjugates of the invention, include archea, prokaryotic host cells, and eukaryotic host cells. In certain embodiments, the host cell is a non-human host cell. Exemplary prokaryotic host cells for use in production of the bioconjugates of the invention include *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. Preferably, the host cell is *E. coli* (e.g. *E. coli* K12 W3110).

Where the host cell is *E. coli* (e.g. *E. coli* K12 W3110), nucleotide sequences comprising polysaccharide synthesis genes for producing a *Klebsiella pneumoniae* O-antigen polysaccharide may be integrated into the *E. coli* O-antigen locus (e.g. the O16-antigen locus of *E. coli* K12 W3110), optionally in place of one or more genes of the *E. coli* O-antigen locus. The sequence of the O-antigen cluster of *E. coli* W3110 is reported in GenBank with accession number U03041 (rfb, GenBank U03041). For example, where the host cell is *E. coli* (e.g. *E. coli* K12 W3110), the *K. pneumoniae* genes wbbM, glf, wbbN, and wbbO, may be integrated into *E. coli* O-antigen locus (e.g. the O16-antigen locus of *E. coli* K12 W3110), optionally retaining the *E. coli* O-antigen promoter as a promoter for the polysaccharide synthesis genes. Where the host cell is *E. coli* (e.g. *E. coli* K12 W3110), nucleotide sequences comprising polysaccharide synthesis genes for producing a *Klebsiella pneumoniae* O-antigen polysaccharide may be integrated into the *E. coli* yeaS locus, optionally in place of the *E. coli* yeaS gene. The genome of *E. coli* K12 W3110 is reported in GenBank with accession number NC_007779. The YeaS gene occupies positions 1,881,835 to 1,882,473 (GenBank NC_007779 position 1,881,835 to 1,882,473). For example, where the host cell is *E. coli* (e.g. *E. coli* K12 W3110), the *K. pneumoniae* genes wbbY and wbbZ may be integrated into the *E. coli* yeaS locus. Thus, the present invention also provides a host cell wherein the host cell is *E. coli* (e.g. *E. coli* K12 W3110) and wherein *K. pneumoniae* genes wbbM, glf, wbbN, and wbbO are integrated into *E. coli* O-antigen locus (e.g. the O16-antigen locus of *E. coli* K12 W3110), optionally in place of one or more genes of the *E. coli* O-antigen locus, and the *K. pneumoniae* genes wbbY and wbbZ are integrated into the *E. coli* yeaSlocus, optionally in place of the *E. coli* yeaS gene.

Host cells may be modified to delete or modify genes in the host cell genetic background (genome) that compete or interfere with the synthesis of the polysaccharide of interest (e.g. compete or interfere with one or more heterologous polysaccharide synthesis genes that are recombinantly introduced into the host cell). These genes can be deleted or modified in the host cell background (genome) in a manner that makes them inactive/dysfunctional (i.e. the host cell nucleotide sequences that are deleted/modified do not encode a functional protein or do not encode a protein whatsoever). In an embodiment, when nucleotide sequences are deleted from the genome of the host cells of the invention, they are replaced by a desirable sequence, e.g. a sequence that is useful for polysaccharide synthesis. Exemplary genes that can be deleted in host cells (and, in some cases, replaced with other desired nucleotide sequences) include genes of host cells involved in glycolipid biosynthesis, such as waaL (see, e.g. Feldman et al. 2005, PNAS USA 102:3016-3021), the O-antigen cluster (rfb or wb), enterobacterial common antigen cluster (wec), the lipid A core biosynthesis cluster (waa), galactose cluster (gal), arabinose cluster (ara), colonic acid cluster (wc), capsular polysaccharide cluster, undecaprenol-pyrophosphate biosynthesis genes (e.g. uppS (Undecaprenyl pyrophosphate synthase), uppP (Undecaprenyl diphosphatase)), Und-P recycling genes, metabolic enzymes involved in nucleotide activated sugar biosynthesis, enterobacterial common antigen cluster, and prophage O antigen modification clusters like the gtrABS cluster. In an embodiment, one or more of the native waaL gene, gtrA gene, gtrB gene, gtrS gene, or a gene or genes from the enterobacterial common antigen cluster (ECA, wec), or a gene, or a gene or genes from the colonic acid cluster (wc) are deleted or functionally inactivated from the genome of a prokaryotic host cell of the invention. In a specific embodiment the host cell of the invention is *E. coli*, wherein the enterobacterial common antigen cluster (ECA, wec) with the exception of wecA, the colanic acid cluster (wca), and the O-antigen cluster (e.g. the O16-antigen cluster of *E. coli* K12 W3110) have been deleted. For example, in *E. coli* K12 W3110 the wec genes are as follows: wecA (UDP-N-acetylglucosamine transferase), wzzE (chain length regulator), wecB (UDP-N-acetylglucosamine epimerase), wecC (UDP-N-acetylmannosamine dehydrogenase), rlmB (TDP-glucose 4,6-dehydratase), rlmA (glucose-1-phosphate thymidylyltransferase), wecD (fucosamine acetyltransferase), wecE (TDP-4-oxo-6-deoxy-D-glucose transaminase), wzxE (ECA translocase), wecF (UDP-N-acetylfucosamine transferase), wzy (ECA polymerase), and wecG (UDP-N-acetylmannosaminuronic acid transferase). In a host cell of the invention, where the native enterobacterial common antigen cluster (ECA, wec) with the exception of wecA is deleted, the genes from wzzE to wecG (i.e. wzzE, wecB, wecC, rlmB, rimA, wecD, wecE, wzxE, wecF, wzy, and wecG) are deleted. In addition, the native lipopolysaccharide O-antigen ligase waaL may be deleted from the host cell of the invention. In addition, the native gtrA gene, gtrB gene and gtrS gene (e.g. the *E. coli* gtrABS genes) may be deleted from the host cell of the invention.

The host cells of the present invention are engineered to comprise heterologous nucleotide sequences. The host cells of the present invention are engineered to comprise a nucleotide sequence that encodes nucleotide sequences comprising polysaccharide synthesis genes for producing a *Klebsiella pneumoniae* O-antigen polysaccharide selected from O1v1, O2a, O2afg and O3b.

Polysaccharide synthesis genes encode proteins involved in synthesis of a polysaccharide. The host cells of the invention may comprise one or more nucleotide sequences sufficient for producing a *Klebsiella pneumoniae* O-antigen polysaccharide selected from O1v1, O2a, O2afg and O3b. Suitably, the present invention provides a host cell comprising nucleotide sequences for producing a *Klebsiella pneumoniae* O-antigen polysaccharide O1v1, O2a, O2afg or O3b, optionally integrated into the host cell genome. For example the present invention provides a host cell comprising nucleotide sequences for producing a *Klebsiella pneumoniae* O-antigen polysaccharide O1v1, optionally integrated into the host cell genome. For example the present invention provides a host cell comprising nucleotide sequences for producing a *Klebsiella pneumoniae* O-antigen polysaccharide O2a, optionally integrated into the host cell genome. For example the present invention provides a host cell comprising nucleotide sequences for producing a *Klebsiella pneumoniae* O-antigen polysaccharide O2afg, optionally integrated into the host cell genome. For example the present invention provides a host cell comprising nucleotide sequences for producing a *Klebsiella pneumoniae* O-antigen polysaccharide O3b, optionally integrated into the host cell genome.

Heterologous nucleotide sequences (e.g. nucleotide sequences that encode carrier proteins and/or nucleotide sequences that encode other proteins, e.g. proteins involved in glycosylation) can be introduced into the host cells of the invention using methods such as electroporation, chemical transformation by heat shock, natural transformation, phage transduction, and conjugation. In specific embodiments, heterologous nucleotide sequences are introduced into the host cells of the invention using a plasmid, e.g. the heterologous nucleotide sequences are expressed in the host cells by a plasmid (e.g. an expression vector). In another specific embodiment, heterologous nucleotide sequences are introduced into the host cells of the invention using the method of insertion described in WO14/037585. In an embodiment, the host cell of the present invention comprises one or more nucleotide sequences that comprise polysaccharide synthesis genes which are heterologous to the host cell. In an embodiment, one or more of said nucleotide sequences that comprise polysaccharide synthesis genes which are heterologous to the host cell are integrated into the genome of the host cell. The nucleotide sequences comprising polysaccharide synthesis genes for producing a *Klebsiella pneumoniae*

O-antigen polysaccharide selected from O1v1, O2a, O2afg and O3b may be integrated into the host cell genome.

The nucleotide sequences comprising polysaccharide synthesis genes for producing a *Klebsiella pneumoniae* O1v1, O2a or O2afg O-antigen polysaccharide may comprise *K. pneumoniae* genes wbbM, glf, wbbN and wbbO. The nucleotide sequences comprising polysaccharide synthesis genes for producing a *Klebsiella pneumoniae* O-antigen may comprise *K. pneumoniae* genes wbbM, glf, wbbN and wbbO from a *K. pneumoniae* strain which expresses an O1v1, O2a or O2afg O-antigen (the wbbM, glf, wbbN and wbbO sequences are identical among several isolates of O1v1, O2a, O2afg). For example, the nucleotide sequences comprising polysaccharide synthesis genes for producing a *Klebsiella pneumoniae* O-antigen may comprise *K. pneumoniae* genes wbbM, glf, wbbN and wbbO from a *K. pneumoniae* strain which expresses an O2a O-antigen. For example, the nucleotide sequences comprising polysaccharide synthesis genes for producing a *Klebsiella pneumoniae* O-antigen may comprise *K. pneumoniae* genes wbbM, glf, wbbN and wbbO from a *K. pneumoniae* strain which expresses an O2afg O-antigen. For example, the nucleotide sequences comprising polysaccharide synthesis genes for producing a *Klebsiella pneumoniae* O-antigen may comprise *K. pneumoniae* genes wbbM, glf, wbbN and wbbO from a *K. pneumoniae* strain which expresses an O1v1 O-antigen. Thus, the present invention provides a host cell wherein the nucleotide sequences comprising polysaccharide synthesis genes for producing a *Klebsiella pneumoniae* O-antigen polysaccharide comprise *K. pneumoniae* genes wbbM, glf, wbbN and wbbO. Preferably, the nucleotide sequence for *K. pneumoniae* gene wbbM comprises (or consists of) a nucleotide sequence at least 95%, 96%, 97%, 98%, 99% or 100% identical to SEQ ID NO: 23. Preferably, the nucleotide sequence for *K. pneumoniae* gene glf comprises (or consists of) a nucleotide sequence at least 95%, 96%, 97%, 98%, 99% or 100% identical to SEQ ID NO: 24. Preferably, the nucleotide sequence for *K. pneumoniae* gene wbbN comprises (or consists of) a nucleotide sequence at least 95%, 96%, 97%, 98%, 99% or 100% identical to SEQ ID NO: 25. Preferably, the nucleotide sequence for *K. pneumoniae* gene wbbO comprises (or consists of) a nucleotide sequence at least 95%, 96%, 97%, 98%, 99% or 100% identical to SEQ ID NO: 26.

In an embodiment, the present invention provides a host cell (e.g. *E. coli*) comprising:
  i) nucleotide sequences for producing a *Klebsiella pneumoniae* O2a O-antigen polysaccharide comprising *K. pneumoniae* genes wbbM, glf, wbbN and wbbO, optionally integrated into the host cell genome;
  ii) a nucleotide sequence encoding a heterologous oligosaccharyl transferase (e.g. pglB, optionally from *Campylobacter jejuni*), optionally within a plasmid;
  iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and
  iv) a nucleotide sequence encoding an ABC transporter, optionally *K. pneumoniae* genes wzm and wzt, optionally integrated into the host cell genome.

The nucleotide sequences comprising polysaccharide synthesis genes for producing a *Klebsiella pneumoniae* O2a O-antigen polysaccharide may comprise *K. pneumoniae* genes wbbM, glf, wbbN and wbbO. Thus, the present invention provides a host cell wherein the nucleotide sequences comprising polysaccharide synthesis genes for producing a *Klebsiella pneumoniae* O-antigen polysaccharide comprise *K. pneumoniae* genes wbbM, glf, wbbN and wbbO. The present invention provides a host cell wherein the nucleotide sequences comprising polysaccharide synthesis genes for producing a *Klebsiella pneumoniae* O2a O-antigen polysaccharide comprise *K. pneumoniae* genes wbbM, glf, wbbN and wbbO. The nucleotide sequences comprising polysaccharide synthesis genes for producing a *Klebsiella pneumoniae* O-antigen may comprise *K. pneumoniae* genes wbbM, glf, wbbN and wbbO from a *K. pneumoniae* strain which expresses an O2 O-antigen (e.g. from a *K. pneumoniae* strain which expresses a O2a O-antigen). Preferably wbbM, glf, wbbN and wbbO are from a *K. pneumoniae* strain which expresses an O2a O-antigen. Preferably, the nucleotide sequence for *K. pneumoniae* gene wbbM comprises (or consists of) a nucleotide sequence at least 95%, 96%, 97%, 98%, 99% or 100% identical to SEQ ID NO: 23. Preferably, the nucleotide sequence for *K. pneumoniae* gene glf comprises (or consists of) a nucleotide sequence at least 95%, 96%, 97%, 98%, 99% or 100% identical to SEQ ID NO: 24. Preferably, the nucleotide sequence for *K. pneumoniae* gene wbbN comprises (or consists of) a nucleotide sequence at least 95%, 96%, 97%, 98%, 99% or 100% identical to SEQ ID NO: 25. Preferably, the nucleotide sequence for *K. pneumoniae* gene wbbO comprises (or consists of) a nucleotide sequence at least 95%, 96%, 97%, 98%, 99% or 100% identical to SEQ ID NO: 26.

In an embodiment, the present invention provides a host cell (e.g. *E. coli*) comprising:
  i) nucleotide sequences for producing a *Klebsiella pneumoniae* O2afg O-antigen polysaccharide comprising *K. pneumoniae* genes wbbM, glf, wbbN, wbbO, gmlA, gmlB and gmlC, optionally integrated into the host cell genome;
  ii) a nucleotide sequence encoding a heterologous oligosaccharyl transferase (e.g. pglB, optionally from *Campylobacter jejuni*), optionally within a plasmid;
  iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and
  iv) a nucleotide sequence encoding an ABC transporter, optionally *K. pneumoniae* genes wzm and wzt, optionally integrated into the host cell genome.

The nucleotide sequences comprising polysaccharide synthesis genes for producing a *Klebsiella pneumoniae* O2afg O-antigen polysaccharide may comprise *K. pneumoniae* genes wbbM, glf, wbbN, wbbO, gmlA, gmlB and gmlC. Thus, the present invention provides a host cell wherein the nucleotide sequences comprising polysaccharide synthesis genes for producing a *Klebsiella pneumoniae* O-antigen polysaccharide comprise *K. pneumoniae* genes wbbM, glf, wbbN, wbbO, gmlA, gmlB and gmlC. The present invention provides a host cell wherein the nucleotide sequences comprising polysaccharide synthesis genes for producing a *Klebsiella pneumoniae* O2afg O-antigen polysaccharide comprise *K. pneumoniae* genes wbbM, glf, wbbN, wbbO, gmlA, gmlB and gmlC. The nucleotide sequences comprising polysaccharide synthesis genes for producing a *Klebsiella pneumoniae* O-antigen may comprise *K. pneumoniae* genes wbbM, glf, wbbN, wbbO, gmlA, gmlB and gmlC from a *K. pneumoniae* strain which expresses an O2 O-antigen (e.g. from a *K. pneumoniae* strain which expresses an O2afg O-antigen). Preferably at least gmlA, gmlB and gmlC are from a *K. pneumoniae* strain which expresses an O2afg O-antigen. Preferably, the nucleotide sequence encoding *K. pneumoniae* gene gmlA comprises (or consists of) a nucleotide sequence at least 95%, 96%, 97%, 98%, 99% or 100% identical to SEQ ID NO: 27. Preferably, the nucleotide sequence encoding *K. pneumoniae* gene gmlB comprises (or consists of) a nucleotide sequence at least 95%, 96%, 97%, 98%, 99% or 100% identical to SEQ ID NO: 28. Preferably, the nucleotide sequence encoding *K. pneumoniae* gene gmlC comprises (or consists of) a nucleotide sequence at least 95%, 96%, 97%, 98%, 99% or 100% identical to SEQ ID NO: 29.

In an embodiment, the present invention provides a host cell (e.g. *E. coli*) comprising:

i) nucleotide sequences for producing a *Klebsiella pneumoniae* O1v1 O-antigen polysaccharide comprising *K. pneumoniae* genes wbbM, glf, wbbN, wbbO, wbbY and wbbZ, optionally integrated into the host cell genome;

ii) a nucleotide sequence encoding a heterologous oligosaccharyl transferase (e.g. pglB, optionally from *Campylobacter jejuni*), optionally within a plasmid;

iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and iv) a nucleotide sequence encoding an ABC transporter, optionally *K. pneumoniae* genes wzm and wzt, optionally integrated into the host cell genome.

The nucleotide sequences comprising polysaccharide synthesis genes for producing a *Klebsiella pneumoniae* O1v1 O-antigen polysaccharide may comprise *K. pneumoniae* genes wbbM, glf, wbbN, wbbO, wbbY and wbbZ. Thus, the present invention provides a host cell wherein the nucleotide sequences comprising polysaccharide synthesis genes for producing a *Klebsiella pneumoniae* O-antigen polysaccharide comprise *K. pneumoniae* genes wbbM, glf, wbbN, wbbO, wbbY and wbbZ. The present invention provides a host cell wherein the nucleotide sequences comprising polysaccharide synthesis genes for producing a *Klebsiella pneumoniae* O1v1 O-antigen polysaccharide comprise *K. pneumoniae* genes wbbM, glf, wbbN, wbbO, wbbY and wbbZ. The nucleotide sequences comprising polysaccharide synthesis genes for producing a *Klebsiella pneumoniae* O1v1 O-antigen may comprise *K. pneumoniae* genes wbbM, glf, wbbN, wbbO, wbbY and wbbZ from a *K. pneumoniae* strain which expresses an O1 O-antigen (e.g. from a *K. pneumoniae* strain which expresses an O1v1 O-antigen). Preferably at least wbbY and wbbZ are from a *K. pneumoniae* strain which expresses an O1v1 O-antigen. Preferably, the nucleotide sequence encoding *K. pneumoniae* gene wbbY comprises (or consists of) a nucleotide sequence at least 95%, 96%, 97%, 98%, 99% or 100% identical to SEQ ID NO: 30. Preferably, the nucleotide sequence encoding *K. pneumoniae* gene wbbZ comprises (or consists of) a nucleotide sequence at least 95%, 96%, 97%, 98%, 99% or 100% identical to SEQ ID NO: 31.

In an embodiment, the present invention provides a host cell (e.g. *E. coli*) comprising:

i) nucleotide sequences for producing a *Klebsiella pneumoniae* O3b O-antigen polysaccharide comprising *K. pneumoniae* genes manC, manB, wbdD, wbdA, wbdB and wbdC, optionally integrated into the host cell genome;

ii) a nucleotide sequence encoding a heterologous oligosaccharyl transferase (e.g. pglB, optionally from *Campylobacter jejuni*), optionally within a plasmid;

iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and iv) a nucleotide sequence encoding an ABC transporter, optionally *K. pneumoniae* genes wzm and wzt, optionally integrated into the host cell genome.

The nucleotide sequences comprising polysaccharide synthesis genes for producing a *Klebsiella pneumoniae* O3b O-antigen polysaccharide may comprise *K. pneumoniae* genes manC, manB, wbdD, wbdA, wbdB and wbdC. Thus, the present invention provides a host cell wherein the nucleotide sequences comprising polysaccharide synthesis genes for producing a *Klebsiella pneumoniae* O-antigen polysaccharide comprise *K. pneumoniae* genes manC, manB, wbdD, wbdA, wbdB and wbdC.

The present invention provides a host cell wherein the nucleotide sequences comprising polysaccharide synthesis genes for producing a *Klebsiella pneumoniae* O3b O-antigen polysaccharide comprise *K. pneumoniae* genes manC, manB, wbdD, wbdA, wbdB and wbdC. The nucleotide sequences comprising polysaccharide synthesis genes for producing a *Klebsiella pneumoniae* O3b O-antigen may comprise *K. pneumoniae* genes manC, manB, wbdD, wbdA, wbdB and wbdC from a *K. pneumoniae* strain which expresses an O3 O-antigen (e.g. from a *K. pneumoniae* strain which expresses an O3b O-antigen). As described in Guachalla et al. (2017) variants in O3 subtypes carry mutations in the mannosyltransferase domains of wbdA. Thus, preferably at least wbdA is from a *K. pneumoniae* strain which expresses an O3b O-antigen. The nucleotide sequences comprising polysaccharide synthesis genes for producing a *Klebsiella pneumoniae* O-antigen may comprise *K. pneumoniae* genes manC, manB, wbdD, wbdA, wbdB and wbdC from a *K. pneumoniae* strain which expresses an O3b O-antigen. Preferably, the nucleotide sequence encoding *K. pneumoniae* gene manC comprises (or consists of) a nucleotide sequence at least 95%, 96%, 97%, 98%, 99% or 100% identical to SEQ ID NO: 32. Preferably, the nucleotide sequence encoding *K. pneumoniae* gene manB comprises (or consists of) a nucleotide sequence at least 95%, 96%, 97%, 98%, 99% or 100% identical to SEQ ID NO: 33. Preferably, the nucleotide sequence encoding *K. pneumoniae* gene wbdD comprises (or consists of) a nucleotide sequence at least 95%, 96%, 97%, 98%, 99% or 100% identical to SEQ ID NO: 36. Preferably, the nucleotide sequence for *K. pneumoniae* encoding wbdA comprises (or consists of) a nucleotide sequence at least 95%, 96%, 97%, 98%, 99% or 100% identical to SEQ ID NO: 37. Preferably, the nucleotide sequence encoding *K. pneumoniae* gene wbdB comprises (or consists of) a nucleotide sequence at least 95%, 96%, 97%, 98%, 99% or 100% identical to SEQ ID NO: 38. Preferably, the nucleotide sequence encoding *K. pneumo-*

*niae* gene wbdC comprises (or consists of) a nucleotide sequence at least 95%, 96%, 97%, 98%, 99% or 100% identical to SEQ ID NO: 39.

The host cells of the present invention are also engineered to comprise a nucleotide sequence that encodes a carrier protein comprising an inserted consensus sequence D/E-X-N-Z-S/T wherein X and Z may be any natural amino acid except proline (e.g. detoxified Exotoxin A of *Pseudomonas aeruginosa* (EPA) comprising an inserted consensus sequence D/E-X-N-Z-S/T wherein X and Z may be any natural amino acid except proline), optionally within a plasmid. For example, host cells of the present invention may comprise a nucleotide sequence that encodes a detoxi-fied Exotoxin A of *Pseudomonas aeruginosa* (EPA) having an amino acid sequence comprising (or consisting) of an amino acid sequence at least 80%, 85%, 90%, 92%, 95%, 96%, 97%, 98% or 99% identical to SEQ ID NO: 16 and having a substitution of leucine 552 to valine (L552V) and deletion of glutamine 553 (ΔE553) and comprising 3 to 7 inserted consensus sequences D/E-X-N-Z-S/T, wherein X and Z may be any natural amino acid except proline. For example, host cells of the present invention may comprise a nucleotide sequence that encodes a detoxified Exotoxin A of *Pseudomonas aeruginosa* (EPA) having an amino acid sequence comprising (or consisting of) an amino acid sequence which is at least 95%, 96%, 97%, 98%, 99% or 100% identical to SEQ ID NO: 17. For example, host cells of the present invention may comprise a nucleotide sequence that encodes a detoxified Exotoxin A of *Pseudomonas aeruginosa* (EPA) with a signal sequence having an amino acid sequence comprising (or consisting of) an amino acid sequence which is at least 95%, 96%, 97%, 98%, 99% or 100% identical to SEQ ID NO: 18.

Thus, host cells of the invention can produce a biocon-jugate comprising a *Klebsiella pneumoniae* O-antigen poly-saccharide selected from O1v1, O2a, O2afg or O3b which is attached to a carrier protein comprising an inserted consen-sus sequence D/E-X-N-Z-S/T wherein X and Z may be any natural amino acid except proline (e.g. detoxified Exotoxin A of *Pseudomonas aeruginosa* (EPA) comprising an inserted consensus sequence D/E-X-N-Z-S/T wherein X and Z may be any natural amino acid except proline.

In an embodiment, the host cells may also comprise heterologous nucleotide sequences that are located outside of an O-antigen cluster. For example, nucleotide sequences encoding glycosyltransferases and acetyltransferases that are found outside of O-antigen clusters and that modify recombinant polysaccharides can be introduced into the host cells.

Oligosaccharyl Transferase

N-linked protein glycosylation (the addition of carbohy-drate molecules to an asparagine residue in the polypeptide chain of the target protein) is the most common type of post-translational modification occurring in the endoplasmic reticulum of eukaryotic organisms. The process is accom-plished by the enzymatic oligosaccharyltransferase complex (OST) responsible for the transfer of a preassembled oligo-saccharide from a lipid carrier (dolichol phosphate) to an asparagine residue of a nascent protein within the conserved sequence Asn-X-Ser/Thr (where X is any amino acid except proline) in the Endoplasmic reticulum.

It has been shown that a bacterium, the food-borne pathogen *Campylobacter jejuni*, can also N-glycosylate its proteins (Wacker et al. Science. 2002; 298(5599): 1790-3) due to the fact that it possesses its own glycosylation machinery. The machinery responsible of this reaction is encoded by a cluster called "pgl" (for protein glycosylation).

The *C. jejuni* glycosylation machinery can be transferred to *E. coli* to allow for the glycosylation of recombinant proteins expressed by the *E. coli* cells. Previous studies have dem-onstrated how to generate *E. coli* strains that can perform N-glycosylation (see, e.g. Wacker et al. Science. 2002; 298 (5599): 1790-3; Nita-Lazar et al. Glycobiology. 2005; 15(4): 361-7; Feldman et al. Proc Natl Acad Sci USA. 2005; 102(8):3016-21; Kowarik et al. EMBO J. 2006; 25(9):1957-66; Wacker et al. Proc Natl Acad Sci USA. 2006; 103(18): 7088-93; International Patent Application Publication Nos. WO2003/074687, WO2006/119987, WO 2009/104074, and WO/2011/06261, and WO2011/138361).

The host cells of the present invention comprise a nucleo-tide sequence encoding a heterologous oligosaccharyl trans-ferase, optionally within a plasmid. In a specific embodi-ment, the oligosaccharyl transferase is an oligosaccharyl transferase from *Campylobacter*. In another specific embodiment, the oligosaccharyl transferase is a pglB, optionally from *Campylobacter jejuni* (i.e. pglB; see, e.g. Wacker et al. 2002, Science 298:1790-1793; see also, e.g. NCBI Gene ID: 3231775, UniProt Accession No. 086154) SEQ ID NO: 15:

```
                                            SEQ ID NO: 15
MLKKEYLKNPYLVLFAMIILAYVFSVFCRFYWVWWASEFNEYFFNNQLMI

ISNDGYAFAEGARDMIAGFHQPNDLSYYGSSLSALTYWLYKITPFSFESI

ILYMSTFLSSLVVIPTILLANEYKRPLMGFVAALLASIANSYYNRTMSGY

YDTDMLVIVLPMFILFFMVRMILKKDFFSLIALPLFIGIYLWWYPSSYTL

NVALIGLFLIYTLIFHRKEKIFYIAVILSSLTLSNIAWFYQSAIIVILFA

LFALEQKRLNFMIIGILGSATLIFLILSGGVDPILYQLKFYIFRSDESAN

LTQGFMYFNVNQTIQEVENVDLSEFMRRISGSEIVFLFSLFGFVWLLRKH

KSMIMALPILVLGFLALKGGLRFTIYSVPVMALGFGFLRYYSDVKTLVDG

GKHLGKDNFFPSFALSKDEQAAANMARLSVEYTEKSFYAPQNDILKTDIL

QAMMKDYNQSNVDLFLASLSKPDFKIDTPKTRDIYLYMPARMSLIFSTVA

SFSFINLDTGVLDKPFTFSTAYPLDVKNGEIYLSNGVVLSDDFRSFKIGD

NVVSVNSIVEINSIKQGEYKITPIDDKAQFYIFYLKDSAIPYAQFILMDK

TMFNSAYVQMFFLGNYDKNLFDLVINSRDAKVFKLKI
```

Thus host cells of the present invention may comprise a nucleotide sequence encoding pglB, optionally pglB from *Campylobacter jejuni*, optionally a nucleotide sequence encoding pglB from *Campylobacter jejuni* having a sequence at least 95%, 96%, 97%, 98%, 99% or 100% identical to SEQ ID NO: 15, optionally within a plasmid.

Chain Elongation

In host cells of the present invention chain elongation is carried out by multifunctional glycosyltransferases (i.e. the nucleotide sequences comprising polysaccharide synthesis genes for producing a *Klebsiella pneumoniae* O-antigen polysaccharide as described herein). Accordingly, there is no need for a polymerase and it is not necessary to introduce a heterologous polymerase. Thus host cells of the present invention may lack a nucleotide sequence encoding a het-erologous polymerase (e.g. wzy).

ABC Transporters

The host cells of the present invention may be engineered to comprise a nucleotide sequence that encodes an ABC transporter. The ABC transporter transfers the repeating units of a polysaccharide from the cytoplasm into the periplam of host cells (e.g. *E. coli*). For example, host cells of the present invention may comprise a nucleotide sequence encoding *K. pneumoniae* genes wzm and wzt. The nucleotide sequences encoding an ABC transporter may comprise *K. pneumoniae* genes wzm and wzt from a *K. pneumoniae* strain which expresses O2 O-antigen (e.g. from a *K. pneumoniae* strain which expresses an O2a O-antigen), e.g. for synthesis of a *Klebsiella pneumoniae* O2a O-antigen. The nucleotide sequences encoding an ABC transporter may comprise *K. pneumoniae* genes wzm and wzt from a *K. pneumoniae* strain which expresses O2 O-antigen (e.g. from a *K. pneumoniae* strain which expresses an O2afg O-antigen), e.g. for synthesis of a *Klebsiella pneumoniae* O2afg O-antigen. The nucleotide sequences encoding an ABC transporter may comprise *K. pneumoniae* genes wzm and wzt from a *K. pneumoniae* strain which expresses O1 O-antigen (e.g. from a *K. pneumoniae* strain which expresses an O1v1 O-antigen), e.g. for synthesis of a *Klebsiella pneumoniae* O1v1 O-antigen. For example, the amino acid sequence encoding *K. pneumoniae* gene wzm comprises (or consists of) a nucleotide sequence at least 95%, 96%, 97%, 98%, 99% or 100% identical to SEQ ID NO: 21. For example, the amino acid sequence encoding *K. pneumoniae* gene wzt comprises (or consists of) a nucleotide sequence at least 95%, 96%, 97%, 98%, 99% or 100% identical to SEQ ID NO: 22. The nucleotide sequences encoding an ABC transporter may comprise *K. pneumoniae* genes wzm and wzt from a *K. pneumoniae* strain which expresses O3 O-antigen (e.g. from a *K. pneumoniae* strain which expresses an O3b O-antigen), e.g. for synthesis of a *Klebsiella pneumoniae* O3b O-antigen. For example, the nucleotide sequence encoding *K. pneumoniae* gene wzm comprises (or consists of) a nucleotide sequence at least 95%, 96%, 97%, 98%, 99% or 100% identical to SEQ ID NO: 34. For example, the nucleotide sequence encoding *K. pneumoniae* gene wzt comprises (or consists of) a nucleotide sequence at least 95%, 96%, 97%, 98%, 99% or 100% identical to SEQ ID NO: 35. The nucleotide sequence that encodes an ABC transporter may be introduced as part of the *Klebsiella pneumoniae* O-antigen cluster for a particular serotype.

The nucleotide sequence encoding the ABC transporter may be integrated into the host cell genome. The nucleotide sequence encoding the ABC transporter may co-localised with the nucleotide sequences comprising polysaccharide synthesis genes for producing a *Klebsiella pneumoniae* O-antigen polysaccharide O1v1, O2a, O2afg or O3b within the host cell genome. Thus, the present invention provides a host cell wherein nucleotide sequences comprising polysaccharide synthesis genes for producing a *Klebsiella pneumoniae* O-antigen polysaccharide O1v1, O2a, O2afg or O3b and the nucleotide sequence encoding an ABC transporter are integrated into the host cell genome, optionally co-localized.

Accessory Enzymes

In an embodiment, nucleotide sequences encoding one or more accessory enzymes are introduced into the host cells of the invention. Thus, a host cell of the invention may further comprise one or more of these accessory enzymes. Such nucleotide sequences encoding one or more accessory enzymes can be either plasmid-borne or integrated into the genome of the host cells of the invention. Exemplary accessory enzymes include, without limitation, epimerases (see e.g. WO2011/062615), branching, modifying (e.g. to add cholins, glycerolphosphates, pyruvates), amidating, acetylating, formylating enzymes.

Bioconjugates

The present invention provides a bioconjugate comprising a *Klebsiella pneumoniae* O-antigen polysaccharide, in particular a *Klebsiella pneumoniae* O-antigen polysaccharide selected from O1v1, O2a, O2afg or O3b, conjugated to a carrier protein, wherein the carrier protein is a detoxified Exotoxin A of *Pseudomonas aeruginosa* (EPA).

The present invention provides a bioconjugate comprising a *Klebsiella pneumoniae* O-antigen polysaccharide O1v1 has the structure -(D-galactan II)n-(D-galactan I)n-GlcNAc:

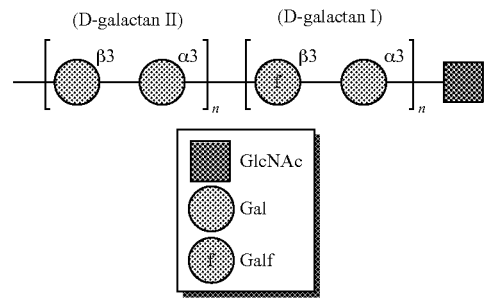

wherein n is the number of repeat units. This structure can also be written as: [→3)-β-D-Galp-(1→3)-α-D-Galp-(1→]n-[→3)-β-D-Galf-(1→3)-α-D-Galp-(1→]n→3)-D-GlcNAc. The number of repeat units for D-galactan II may be different from the number of repeat units for D-galactan I. Optionally the number of repeat units (n) ranges from 4 to 8 or 5 to 7, for example 6 for D-galactan II and the number of repeat units (n) ranges from 2 to 10 or 3 to 7, for example 4 for D-galactan I. For example, the number of repeat units (n) may range from 5 to 7 for D-galactan II and the number of repeat units (n) may range from 3 to 5 for D-galactan I. Optionally the ratio of D-galactan II:D-galactan I ranges between 2:1 to 1:50 or 2:1 to 1:2 (e.g. between 1.5:1 to 2:1).

The present invention provides a bioconjugate comprising a *Klebsiella pneumoniae* O-antigen polysaccharide O2a has the structure -(D-galactan I)n-GlcNAc:

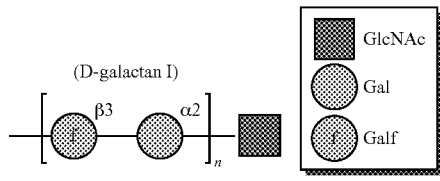

wherein n is the number of repeat units. This structure can also be written as: [→3)-β-D-Galf-(1→3)-α-D-Galp-(1→]n→3)-D-GlcNAc. Optionally the number of repeat units (n) ranges from 10 to 30, e.g. from 15 to 30.

The present invention provides a bioconjugate comprising a *Klebsiella pneumoniae* O-antigen polysaccharide O2afg has the structure -(D-galactan III)n-GlcNAc:

(D-galactan III)

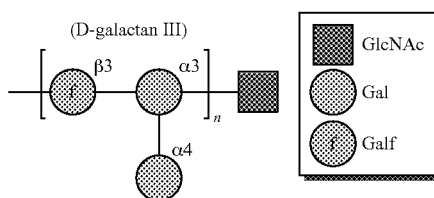

wherein n is the number of repeat units. This structure can also be written as: [→3)-β-D-Galf-(1→3)-[α-D-Galp-(1→4)]-α-D-Galp(1→]n→3)-D-GlcNAc. Optionally the number of repeat units (n) ranges from 5 to 25 (e.g. from 5 to 15). Optionally the degree of branching ranges from 90-100%.

The present invention provides a bioconjugate comprising a *Klebsiella pneumoniae* O-antigen polysaccharide O3b has the structure Me-P-3(Man-α2-Man-α3-Man-α3)n-Man-α3-Man-α3-GlcNAc:

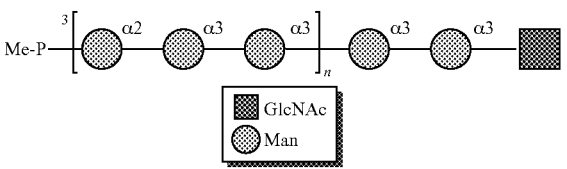

wherein n is the number of repeat units. This structure can also be written as: Me-P-[→3)-α-D-Man(1→2)-α-D-Man(1→3)-α-D-Man(1-]n→3)-α-D-Man(1→3)-α-D-Man(1→3)-D-GlcNAc. Optionally the number of repeat units (n) ranges from 5 to 25 (e.g. from 10 to 20).

The present invention provides a bioconjugate according to the invention wherein the detoxified Exotoxin A of *Pseudomonas aeruginosa* (EPA) comprises 3 to 7 inserted consensus sequences D/E-X-N-Z-S/T (SEQ ID NO. 1), wherein X and Z may be any natural amino acid except proline. For example, a detoxified Exotoxin A of *Pseudomonas aeruginosa* (EPA) having an amino acid sequence comprising (or consisting) of an amino acid sequence at least 80%, 85%, 90%, 92%, 95%, 96%, 97%, 98% or 99% identical to SEQ ID NO: 16 and having a substitution of leucine 552 to valine (L552V) and deletion of glutamine 553 (ΔE553) and comprising 3 to 7 inserted consensus sequences D/E-X-N-Z-S/T, wherein X and Z may be any natural amino acid except proline. For example, a detoxified Exotoxin A of *Pseudomonas aeruginosa* (EPA) having an amino acid sequence comprising (or consisting of) an amino acid sequence which is at least 95%, 96%, 97%, 98%, 99% or 100% identical to SEQ ID NO: 17. Thus, the present invention provides a bioconjugate wherein the detoxified Exotoxin A of *Pseudomonas aeruginosa* (EPA) comprises 3 to 7 inserted consensus sequences D/E-X-N-Z-S/T, wherein X and Z may be any natural amino acid except proline, optionally comprising (or consisting of) an amino acid sequence which is at least 95%, 96%, 97%, 98%, 99% or 100% identical to SEQ ID NO: 17.

The *Klebsiella pneumoniae* O-antigen may be linked to an amino acid on the modified EPA protein selected from asparagine, aspartic acid, glutamic acid, lysine, cysteine, tyrosine, histidine, arginine or tryptophan (e.g. asparagine). Bioconjugates, as described herein, have advantageous properties over chemical conjugates of antigen-carrier protein, in that they require less chemicals in manufacture and are more consistent in terms of the final product generated.

A further aspect of the invention is a process for producing a bioconjugate that comprises (or consists of) a *Klebsiella pneumoniae* O-antigen polysaccharide selected from O1v1, O2a, O2afg or O3b, conjugated to a carrier protein, wherein the carrier protein is a detoxified Exotoxin A of *Pseudomonas aeruginosa* (EPA), said process comprising (i) culturing the host cell of the invention under conditions suitable for the production of glycoproteins and (ii) isolating the bioconjugate produced by said host cell, optionally isolating the bioconjugate from a periplasmic extract from the host cell. There is thus provided a process for producing a bioconjugate comprising (i) culturing the host cell of the invention under conditions suitable for the production of glycoproteins and (ii) isolating the bioconjugate. There is also provided a process for producing a bioconjugate comprising (i) culturing the host cell of the invention under conditions suitable for the production of glycoproteins and (ii) isolating the bioconjugate from a periplasmic extract from the host cell.

For example, bioconjugates can be made using the shake flask process, e.g. in a LB shake flask. In aspect of the invention, a fed-batch process for the production of recombinant glycosylated proteins in bacteria can be used to produce bioconjugates of the invention. The aim is to increase glycosylation efficiency and recombinant protein yield per cell and while maintaining simplicity and reproducibility in the process. Bioconjugates of the present invention can be manufactured on a commercial scale by developing an optimized manufacturing method using typical *E. coli* production processes. Various types of feed strategies, such as batch, chemostat and fed-batch can be used.

The bioconjugates of the invention can be purified for example, by chromatography (e.g. ion exchange, anionic exchange, affinity, and sizing column chromatography), centrifugation, differential solubility, or by any other standard technique for the purification of proteins. See, e.g. Saraswat et al. 2013, Biomed. Res. Int. ID #312709 (p. 1-18); see also the methods described in WO 2009/104074. Further, the bioconjugates may be fused to heterologous polypeptide sequences described herein or otherwise known in the art to facilitate purification.

The present invention also provides an immunogenic composition comprising the conjugate (e.g. bioconjugate) of the invention, and optionally a pharmaceutically acceptable excipient and/or carrier. The invention provides an immunogenic composition comprising a *Klebsiella pneumoniae* O1v1 O-antigen polysaccharide conjugate (e.g. bioconjugate) of the invention. The invention provides an immunogenic composition comprising a *Klebsiella pneumoniae* O2a O-antigen polysaccharide conjugate (e.g. bioconjugate) of the invention. The invention provides an immunogenic composition comprising a *Klebsiella pneumoniae* O2afg O-antigen polysaccharide conjugate (e.g. bioconjugate) of the invention. The invention provides an immunogenic composition comprising a *Klebsiella pneumoniae* O3b O-antigen polysaccharide conjugate (e.g. bioconjugate) of the invention.

Analytical Methods

Various methods can be used to analyze the structural compositions and sugar chain lengths of the bioconjugates of the invention and to determine glycosylation site usage.

Hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide. See Bigge J C, Patel T P, Bruce J A, Goulding P N, Charles S M, Parekh R B: Nonselective and efficient fluorescent labeling of glycans using 2-amino benzamide and anthranilic acid. Anal Biochem 1995, 230(2):229-238. The labeled polysaccharides are separated on a GlycoSep-N column (GL Sciences) according to the HPLC protocol of Royle et al., See Royle L, Mattu T S, Hart E, Langridge J I, Merry A H, Murphy N, Harvey D J, Dwek R A, Rudd P M: An analytical and structural database provides a strategy for sequencing O-glycans from microgram quantities of glycoproteins. Anal Biochem 2002, 304(1):70-90. The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit can be confirmed and additionally in homogeneity of the polysaccharide composition can be identified. Alternatively, high mass MS and size exclusion HPLC can be applied to measure the size of the complete bioconjugates.

Yield may be measured as carbohydrate amount derived from a liter of bacterial production culture grown in a bioreactor under controlled and optimized conditions. After purification of bioconjugate, the carbohydrate yields can be directly measured by either the anthrone assay or ELISA using carbohydrate specific antisera. Indirect measurements are possible by using the protein amount (measured by BCA, Lowry, or bardford assays) and the glycan length and structure to calculate a theoretical carbohydrate amount per gram of protein. In addition, yield can also be measured by drying the glycoprotein preparation from a volatile buffer and using a balance to measure the weight.

Various methods can be used to analyze the conjugates of the invention including, for example, SDS-PAGE or capillary gel electrophoresis. Polymer length is defined by the number of repeat units that are linearly assembled. This means that the typical ladder like pattern is a consequence of different repeat unit numbers that compose the glycan. Thus, two bands next to each other in SDS PAGE (or other techniques that separate by size) differ by only a single repeat unit. These discrete differences are exploited when analyzing glycoproteins for glycan size: the unglycosylated carrier protein and the bioconjugate with different polymer chain lengths separate according to their electrophoretic mobilities. The first detectable repeat unit number ($n_1$) and the average repeat unit number ($n_{average}$) present on a bioconjugate are measured. These parameters can be used to demonstrate batch to batch consistency or polysaccharide stability, for example.

Glycosylation site usage may be quantified by, for example, glycopeptide LC-MS/MS: conjugates are digested with protease(s), and the peptides are separated by a suitable chromatographic method (C18, Hydrophilic interaction HPLC HILIC, GlycoSepN columns, SE HPLC, AE HPLC), and the different peptides are identified using MS/MS. This method can be used with or without previous sugar chain shortening by chemical (smith degradation) or enzymatic methods. Quantification of glycopeptide peaks using UV detection at 215 to 280 nm allows relative determination of glycosylation site usage. In another embodiment, site usage may be quantified by size exclusion HPLC: Higher glycosylation site usage is reflected by an earlier elution time from a SE HPLC column. In yet another embodiment, site usage may be quantified by quantitative densitometry of purified bioconjugates stained with Coomassie Briliant Blue following sodium dodecyl sulfate-polyacrylamide gel electrophoresis (SDS-PAGE).

Vaccines

The present invention also provides an immunogenic composition (e.g., a vaccine composition) optionally comprising an adjuvant.

The term "adjuvant" refers to a compound that when administered in conjunction with or as part of an immunogenic composition of vaccine of the invention augments, enhances and/or boosts the immune response to a conjugate (e.g. bioconjugate) of the invention, but when the compound is administered alone does not generate an immune response to the conjugate (e.g. bioconjugate). Adjuvants can enhance an immune response by several mechanisms including, e.g. lymphocyte recruitment, stimulation of B and/or T cells, and stimulation of macrophages. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS01 (GlaxoSmithKline), and saponins, such as QS21 (see Kensil et al. in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al. N. Engl. J. Med. 336, 86-91 (1997)).

Also provided is a method of making the immunogenic composition of the invention comprising the step of mixing the conjugate (e.g. bioconjugate) of the invention with a pharmaceutically acceptable excipient and/or carrier and an adjuvant. Vaccine preparation is generally described in Vaccine Design ("The subunit and adjuvant approach" (eds Powell M. F. & Newman M. J.) (1995) Plenum Press New York).

The immunogenic compositions of the invention can be included in a container, pack, or dispenser together with instructions for administration.

The immunogenic compositions or vaccines of the invention can be stored before use, e.g. the compositions can be stored frozen (e.g. at about −20° C. or at about −70° C.); stored in refrigerated conditions (e.g. at about 4° C.); or stored at room temperature. The immunogenic compositions or vaccines of the invention may be stored in solution or lyophilized. In an embodiment, the solution is lyophilized in the presence of a sugar such as sucrose, trehalose or lactose. In another embodiment, the vaccines of the invention are lyophilized and extemporaneously reconstituted prior to use.

Administration and Dosage

Immunogenic compositions or vaccines of the invention may be used to protect or treat a subject (e.g. mammal), by means of administering said immunogenic composition or vaccine via systemic or mucosal route. These administrations may include injection via the intramuscular (IM), intraperitoneal, intradermal (ID) or subcutaneous (SC) routes; or via mucosal administration to the oral/alimentary, respiratory, genitourinary tracts.

In one aspect, the immunogenic composition or vaccine of the invention is administered by the intramuscular delivery route. Intramuscular administration may be to the thigh or the upper arm. Injection is typically via a needle (e.g. a hypodermic needle), but needle-free injection may alternatively be used. A typical intramuscular dose is 0.5 ml.

In another aspect, the immunogenic composition or vaccine of the invention is administered by the intradermal administration. Human skin comprises an outer "horny" cuticle, called the stratum corneum, which overlays the epidermis. Underneath this epidermis is a layer called the dermis, which in turn overlays the subcutaneous tissue. The conventional technique of intradermal injection, the "mantoux procedure", comprises steps of cleaning the skin, and then stretching with one hand, and with the bevel of a narrow gauge needle (26 to 31 gauge) facing upwards the needle is inserted at an angle of between 10 to 15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

In another aspect, the immunogenic composition or vaccine of the invention is administered by the intranasal administration. Typically, the immunogenic composition or vaccine is administered locally to the nasopharyngeal area, e.g. without being inhaled into the lungs. It is desirable to use an intranasal delivery device which delivers the immunogenic composition or vaccine formulation to the nasopharyngeal area, without or substantially without it entering the lungs. Suitable devices for intranasal administration of the vaccines according to the invention are spray devices. Suitable commercially available nasal spray devices include ACCUSPRAY™ (Becton Dickinson).

Immunogenic compositions comprise an immunologically effective amount of one or more *Klebsiella pneumoniae* polysaccharide conjugates (e.g. bioconjugates) of the invention, as well as any other components. By "immunologically effective amount", it is meant that the administration of that amount to an individual, either as a single dose or as part of a series is effective for treatment or prevention of a *Klebsiella pneumoniae* infection, disease or condition. This amount varies depending on the health and physical condition of the individual to be treated, age, the degree of protection desired, the formulation of the vaccine and other relevant factors.

The amount of conjugate (e.g. bioconjugate) in each immunogenic composition or vaccine dose is selected as an amount which induces an immunoprotective response without significant, adverse side effects in typical vaccines. Such amount will vary depending upon which specific immunogen is employed and how it is presented. The content of conjugate (e.g. bioconjugate) will typically be in the range 1-100 µg, suitably 5-50 µg.

Prophylactic and Therapeutic Uses

The present invention also provides an immunogenic composition of the invention, or the vaccine of the invention, for use in medicine.

Provided herein are methods (and uses) of inducing an immune response in a subject against *Klebsiella pneumoniae*, comprising administering to the subject a conjugate (e.g. bioconjugate) of the invention an immunogenic composition of the invention or a vaccine of the invention. The immunogenic composition of the invention or the vaccine of the invention comprises conjugate(s) (e.g. bioconjugate(s)) of *Klebsiella pneumoniae* O1v1 O-antigen polysaccharide, *Klebsiella pneumoniae* O2a O-antigen polysaccharide conjugate, *Klebsiella pneumoniae* O2afg O-antigen polysaccharide and/or a *Klebsiella pneumoniae* O3b O-antigen polysaccharide, wherein each of the *Klebsiella pneumoniae*

O1v1, O2a, O2afg and O3b O-antigen polysaccharides are individually conjugated to a carrier protein. In an embodiment, the conjugate(s) is/are bioconjugate(s). In one embodiment, said subject has bacterial infection at the time of administration. In another embodiment, said subject does not have a bacterial infection at the time of administration.

Thus, the present invention provides a method of inducing an immune response to *Klebsiella pneumoniae* in a subject, the method comprising administering a therapeutically or prophylactically effective amount of the immunogenic composition of the invention, or the vaccine of the invention, to a subject (e.g. human) in need thereof. The present invention also provides an immunogenic composition of the invention, or the vaccine of the invention, for use in inducing an immune response to *Klebsiella pneumoniae* in a subject (e.g. human). The present invention also provides an immunogenic composition of the invention for use in the manufacture of a medicament for inducing an immune response to *Klebsiella pneumoniae* in a subject (e.g. human). Also provided herein are methods (and uses) of inducing the production of opsonophagocytic antibodies in a subject (e.g. human) against *Klebsiella pneumoniae*, comprising administering to the subject a conjugate (e.g. bioconjugate) of the invention an immunogenic composition of the invention or a vaccine of the invention. In an embodiment, the conjugate (e.g. bioconjugate) of the invention an immunogenic composition of the invention or a vaccine of the invention can be used to induce the production of opsonophagocytic antibodies in a subject (e.g. human) against *Klebsiella pneumoniae*.

The present invention also provides methods of treating and/or preventing a *Klebsiella pneumoniae* infection in a subject comprising administering to the subject a conjugate (e.g. bioconjugate) of the invention. The conjugate (e.g. bioconjugate) may be in the form of an immunogenic composition or vaccine. Thus, the present invention provides a method of treating or preventing a *Klebsiella pneumoniae* infection, disease or condition in a subject, the method comprising administering a therapeutically or prophylactically effective amount of the immunogenic composition of the invention, or the vaccine of the invention, to a subject (e.g. human) in need thereof. The present invention also provides an immunogenic composition of the invention, or the vaccine of the invention, for use in treating or preventing a *Klebsiella pneumoniae* infection, disease or condition in a subject (e.g. human). The present invention also provides an immunogenic composition of the invention for use in the manufacture of a medicament for treating or preventing a *Klebsiella pneumoniae* infection, disease or condition in a subject (e.g. human).

Cross-Reactivity

The present inventors have found that sera obtained by immunization with certain *Klebsiella* O-antigen serotypes are cross-reactive and can thus provide cross-protection against other *Klebsiella* O-antigen serotypes despite the antigenic differences between the serotypes. The present inventors have found that antisera generated by immunization with a conjugate of *Klebsiella pneumoniae* O1v1 O-antigen polysaccharide bind the corresponding subserotype *Klebsiella pneumoniae* O1v2 O-antigen polysaccharide and that antisera generated by immunization with a conjugate of *Klebsiella pneumoniae* O1v2 O-antigen polysaccharide bind the corresponding subserotype *Klebsiella pneumoniae* O1v1 O-antigen polysaccharide. The cross protection between these two distinct subserotypes allows a vaccine comprising either an O1v1 or O1v2 serotype to protect against the other serotype. This means that the multivalent immunogenic composition or vaccine of the invention can offer a broader protection against the range of *Klebsiella pneumoniae* sero-types, covering greater than 60% of non-resistant strains and greater than 75% of resistant strains (with cross-reactivity it is estimated to cover 80.4% of non-resistant strains and 81.9% of resistant strains). The advantages of such an immunogenic composition/vaccine include minimizing the cost of goods and minimizing the likelihood of interference of one antigen over another.

Thus the present invention provides a method of treating or preventing a *Klebsiella pneumoniae* infection, disease or condition associated with an O1v2 strain of *Klebsiella pneumoniae* in a subject, the method comprising adminis-tering a therapeutically or prophylactically effective amount of an immunogenic composition of the invention or the vaccine of the invention, comprising a conjugate (e.g. bio-conjugate) of a *Klebsiella pneumoniae* O1v1 O-antigen polysaccharide, to a subject (e.g. human) in need thereof. The present invention also provides an immunogenic com-position of the invention or a vaccine of the invention, comprising a conjugate (e.g. bioconjugate) of a *Klebsiella pneumoniae* O1v1 O-antigen polysaccharide, for use in treating or preventing a *Klebsiella pneumoniae* infection, disease or condition associated with an O1v2 strain of *Klebsiella pneumoniae* in a subject (e.g. human). The pres-ent invention also provides an immunogenic composition of the invention comprising a conjugate (e.g. bioconjugate) of a *Klebsiella pneumoniae* O1v1 O-antigen polysaccharide, for use in the manufacture of a medicament for treating or preventing a *Klebsiella pneumoniae* infection, disease or condition associated with an O1v2 strain of *Klebsiella pneumoniae* in a subject (e.g. human).

In an embodiment, the immunogenic composition of the invention, or vaccine of the invention comprising a conju-gate (e.g. bioconjugate of *Klebsiella pneumoniae* O1v1 O-antigen polysaccharide), when administered to a subject (e.g. human), is able to induce the formation of antibodies capable of binding to *Klebsiella pneumoniae* O1v2 as mea-sured by ELISA assay. In the ELISA (Enzyme-linked Immu-nosorbent Assay) method, antibodies from the sera of vac-cinated subjects are incubated with polysaccharides which have been adsorbed to a solid support. The bound antibodies are detected using enzyme-conjugated secondary detection antibodies.

In an embodiment, the immunogenic composition of the invention, or the vaccine of the invention, does not comprise *Klebsiella pneumoniae* O1v2 O-antigen polysaccharide. Thus the present invention provides a method of treating or preventing a *Klebsiella pneumoniae* infection, disease or condition associated with an O1v2 strain of *Klebsiella pneumoniae* in a subject, the method comprising adminis-tering a therapeutically or prophylactically effective amount of an immunogenic composition of the invention or a vaccine of the invention, comprising a conjugate (e.g. bio-conjugate) of a *Klebsiella pneumoniae* O1v1 O-antigen polysaccharide and which does not comprise *Klebsiella pneumoniae* O1v2 O-antigen polysaccharide, to a subject (e.g. human) in need thereof. The present invention also provides an immunogenic composition of the invention or a vaccine of the invention, comprising a conjugate (e.g. bio-conjugate) of a *Klebsiella pneumoniae* O1v1 O-antigen polysaccharide and which does not comprise *Klebsiella pneumoniae* O1v2 O-antigen polysaccharide, for use in treating or preventing a *Klebsiella pneumoniae* infection, disease or condition associated with an O1v2 strain of *Klebsiella pneumoniae* in a subject (e.g. human). The pres-ent invention also provides an immunogenic composition of the invention comprising a conjugate (e.g. bioconjugate) of a *Klebsiella pneumoniae* O1v1 O-antigen polysaccharide and which does not comprise *Klebsiella pneumoniae* O1v2 O-antigen polysaccharide, for use in the manufacture of a medicament for treating or preventing a *Klebsiella pneumo-niae* infection, disease or condition associated with an O1v2 strain of *Klebsiella pneumoniae* in a subject (e.g. human).

Embodiments of the invention are further described in the subsequent numbered paragraphs:

1. An immunogenic composition comprising a *Klebsiella pneumoniae* O1v1 O-antigen polysaccharide conju-gate, a *Klebsiella pneumoniae* O2a O-antigen polysac-charide conjugate, a *Klebsiella pneumoniae* O2afg O-antigen polysaccharide conjugate and a *Klebsiella pneumoniae* O3b O-antigen polysaccharide conjugate, wherein each of the *Klebsiella pneumoniae* O1v1, O2a, O2afg and O3b O-antigen polysaccharides are indi-vidually conjugated to a carrier protein (e.g. a detoxi-fied Exotoxin A of *Pseudomonas aeruginosa* (EPA)).

2. The immunogenic composition according to paragraph 1 wherein the carrier protein comprises an inserted consensus sequence D/E-X-N-Z-S/T wherein X and Z may be any natural amino acid except proline.

3. The immunogenic composition according to paragraph 1 or paragraph 2 wherein the carrier protein is a detoxified Exotoxin A of *Pseudomonas aeruginosa* (EPA).

4. The immunogenic composition according to paragraph 3 wherein the detoxified Exotoxin A of *Pseudomonas aeruginosa* (EPA) comprises 3 to 7 inserted consensus sequences D/E-X-N-Z-S/T, wherein X and Z may be any natural amino acid except proline, optionally com-prising (or consisting of) an amino acid sequence which is at least 95%, 96%, 97%, 98%, 99% or 100% identical to SEQ ID NO: 17.

5. The immunogenic composition according to any of paragraphs 1 to 4 wherein the *Klebsiella pneumoniae* O1v1 O-antigen polysaccharide has the structure: -(D-galactan II)n-(D-galactan I)n-GlcNAc

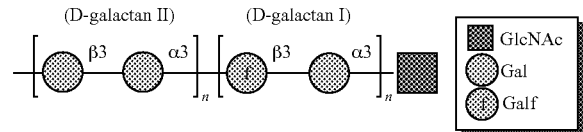

optionally wherein the number of repeat units n ranges from 5 to 7 for D-galactan II and the number of repeat units n ranges from 2 to 10 for D-galactan I and optionally wherein the ratio of D-galactan II:D-galactan I ranges between 2:1 to 1:50.

6. The immunogenic composition according to any of paragraphs 1 to 5 wherein the *Klebsiella pneumoniae* O2a O-antigen polysaccharide has the structure -(D-galactan I)n-GlcNAc:

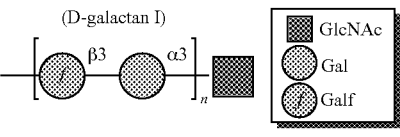

optionally wherein the number of repeat units n ranges from 10 to 30.

7. The immunogenic composition according to any of paragraphs 1 to 6 wherein the *Klebsiella pneumoniae* O2afg O-antigen polysaccharide has the structure -(D-galactan III)n-GlcNAc:

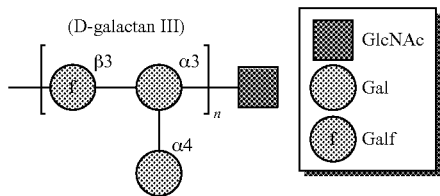

optionally wherein the number of repeat units n ranges from 5 to 25 and optionally wherein the degree of branching ranges from 90-100%.

8. The immunogenic composition according to any of paragraphs 1 to 7 wherein the *Klebsiella pneumoniae* O3b O-antigen polysaccharide has the structure Me-P-3(Man-α2-Man-α3-Man-α3)n-Man-α3-Man-α3-GlcNAc:

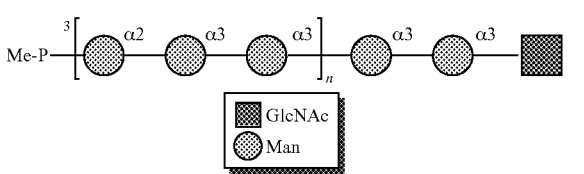

optionally wherein the number of repeat units n ranges from 5 to 25.

9. A process for making an immunogenic composition of any of paragraphs 1 to 8, comprising combining a *Klebsiella pneumoniae* O1v1 O-antigen polysaccharide conjugate, a *Klebsiella pneumoniae* O2a O-antigen polysaccharide conjugate, a *Klebsiella pneumoniae* O2afg O-antigen polysaccharide conjugate and a *Klebsiella pneumoniae* O3b O-antigen polysaccharide conjugate, and optionally a pharmaceutically acceptable excipient and/or carrier.

10. A host cell comprising:
   i) nucleotide sequences comprising polysaccharide synthesis genes for producing a *Klebsiella pneumoniae* O-antigen polysaccharide selected from O1v1, O2a, O2afg and O3b, optionally integrated into the host cell genome;
   ii) a nucleotide sequence encoding a heterologous oligosaccharyl transferase, optionally within a plasmid;
   iii) a nucleotide sequence that encodes a carrier protein comprising an inserted consensus sequence D/E-X-N-Z-S/T wherein X and Z may be any natural amino acid except proline (e.g. detoxified exotoxin A of *Pseudomonas aeruginosa* (EPA) comprising an inserted consensus sequence D/E-X-N-Z-S/T wherein X and Z may be any natural amino acid except proline), optionally within a plasmid; and
   iv) a nucleotide sequence encoding an ABC transporter, optionally *K. pneumoniae* genes wzm and wzt, optionally integrated into the host cell genome.

11. The host cell according to paragraph 10 wherein nucleotide sequences comprising polysaccharide synthesis genes for producing a *Klebsiella pneumoniae*

O-antigen polysaccharide O1v1, O2a, O2afg or O3b and the nucleotide sequence encoding an ABC transporter are integrated into the host cell genome, optionally co-localized.

12. The host cell according to paragraph 10 wherein the nucleotide sequences comprising polysaccharide synthesis genes for producing a *Klebsiella pneumoniae* O-antigen polysaccharide comprise *K. pneumoniae* genes wbbM, glf, wbbN and wbbO.

13. The host cell according to paragraph 10 wherein the nucleotide sequences comprising polysaccharide synthesis genes for producing a *Klebsiella pneumoniae* O-antigen polysaccharide comprise *K. pneumoniae* genes wbbM, glf, wbbN, wbbO, gmlA, gmlB and gmlC.

14. The host cell according to paragraph 10 wherein the nucleotide sequences comprising polysaccharide synthesis genes for producing a *Klebsiella pneumoniae* O-antigen polysaccharide comprise *K. pneumoniae* genes wbbM, glf, wbbN, wbbO, wbbY and wbbZ.

15. The host cell according to paragraph 10 wherein the nucleotide sequences comprising polysaccharide synthesis genes for producing a *Klebsiella pneumoniae* O-antigen polysaccharide comprise *K. pneumoniae* genes manC, manB, wbdD, wbdA, wbdB and wbdC.

16. The host cell according to any of paragraphs 10 to 15 wherein the host cell is *E. coli* (e.g. *E. coli* K12 W3110).

17. The host cell according to paragraphs 12, 13 or 14 wherein the host cell is *E. coli* (e.g. *E. coli* K12 W3110) and wherein *K. pneumoniae* genes wbbM, glf, wbbN, wbbO are integrated into the *E. coli* O-antigen locus (e.g. the O16-antigen locus of *E. coli* K12 W3110), optionally in place of one or more genes of the *E. coli* O-antigen locus.

18. The host cell according to paragraph 14 wherein the host cell is *E. coli* (e.g. *E. coli* K12 W3110) and wherein *K. pneumoniae* genes wbbM, glf, wbbN, wbbO are integrated into *E. coli* O-antigen locus (e.g. the O16-antigen locus of *E. coli* K12 W3110), optionally in place of one or more genes of the *E. coli* O-antigen locus, and the *K. pneumoniae* genes wbbY and wbbZ are integrated into the *E. coli* yeaS locus, optionally in place of the *E. coli* yeaS gene.

19. The host cell according to any of paragraphs 10 to 18 wherein the heterologous oligosaccharyl transferase is a PgIB, optionally derived from *Campylobacter jejuni*.

20. The host cell according to any of paragraphs 10 to 19 wherein the host cell is *E. coli* and the native enterobacterial common antigen cluster (ECA, wec) with the exception of wecA, the colanic acid cluster (wca), and the O-antigen cluster (e.g. the O16-antigen cluster of *E. coli* K12 W3110) have been deleted.

21. The host cell according to paragraph 20 wherein the *E. coli* lipopolysaccharide O-antigen ligase waaL has been deleted.

22. The host cell according to paragraph 20 or paragraph 21 wherein the *E. coli* gtrABS genes have been deleted.

23. A process for producing a bioconjugate comprising (i) culturing the host cell of any of paragraphs 10 to 22 under conditions suitable for the production of glycoproteins and (ii) isolating the bioconjugate.

24. A process for producing a bioconjugate according to paragraph 23 comprising isolating the bioconjugate from a periplasmic extract from the host cell.

25. A conjugate (e.g. bioconjugate) comprising a *Klebsiella pneumoniae* O-antigen polysaccharide selected from O1v1, O2a, O2afg or O3b conjugated to a carrier protein, wherein the carrier protein is a detoxified Exotoxin A of *Pseudomonas aeruginosa* (EPA).

26. A conjugate (e.g. bioconjugate) according to paragraph 25 wherein the *Klebsiella pneumoniae* O-antigen polysaccharide is O1v1 has the structure -(D-galactan II)n-(D-galactan I)n-GlcNAc:

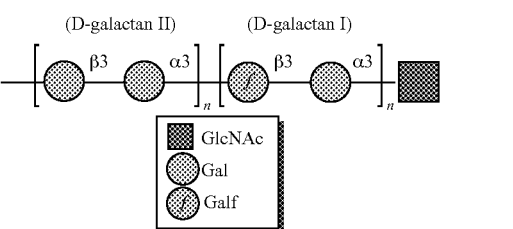

optionally wherein the number of repeat units n ranges from 5 to 7 for D-galactan II and the number of repeat units n ranges from 3 to 5 for D-galactan I and optionally wherein the ratio of D-galactan II:D-galactan I ranges between 2:1 to 1:50.

27. A conjugate (e.g. bioconjugate) according to paragraph 25 wherein the *Klebsiella pneumoniae* O-antigen polysaccharide is O2a has the structure -(D-galactan I)n-GlcNAc:

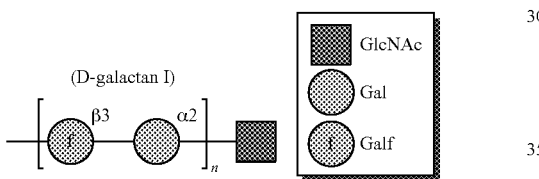

optionally wherein the number of repeat units n ranges from 15 to 30.

28. A conjugate (e.g. bioconjugate) according to paragraph 25 wherein the *Klebsiella pneumoniae* O-antigen polysaccharide is O2afg has the structure -(D-galactan III)n-GlcNAc:

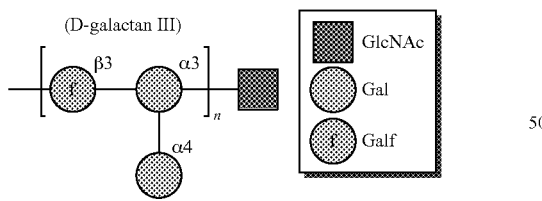

optionally wherein the number of repeat units n ranges from 5 to 15 and optionally wherein the degree of branching ranges from 90-100%.

29. A conjugate (e.g. bioconjugate) according to paragraph 25 wherein the *Klebsiella pneumoniae* O-antigen polysaccharide is O3b has the structure Me-P-3(Man-α2-Man-α3-Man-α3)n-Man-α3-Man-α3-GlcNAc:

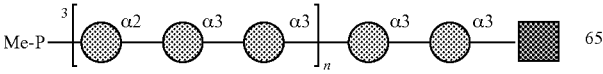

44

-continued

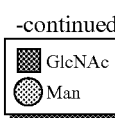

optionally wherein the number of repeat units n ranges from 10 to 20.

30. A bioconjugate according to any of paragraphs 25 to 29 wherein the detoxified Exotoxin A of *Pseudomonas aeruginosa* (EPA) comprises 3 to 7 inserted consensus sequences D/E-X-N-Z-S/T, wherein X and Z may be any natural amino acid except proline, optionally comprising (or consisting of) an amino acid sequence which is at least 95%, 96%, 97%, 98%, 99% or 100% identical to SEQ ID NO: 17.

31. An immunogenic composition comprising the conjugate (e.g. bioconjugate) of any of paragraphs 25 to 30, and optionally a pharmaceutically acceptable excipient and/or carrier.

32. A vaccine comprising the immunogenic composition of any of paragraphs 1 to 8 or paragraph 31 and optionally an adjuvant.

33. A method of inducing an immune response to *Klebsiella pneumoniae* in a subject, the method comprising administering a therapeutically or prophylactically effective amount of the immunogenic composition of paragraphs 1 to 8 or 31, or the vaccine of paragraph 32, to a subject (e.g. human) in need thereof.

34. A method of treating or preventing a *Klebsiella pneumoniae* infection, disease or condition in a subject, the method comprising administering a therapeutically or prophylactically effective amount of the immunogenic composition of paragraphs 1 to 8 or 31, or the vaccine of paragraph 32, to a subject (e.g. human) in need thereof.

35. A method of treating or preventing a *Klebsiella pneumoniae* infection, disease or condition associated with an O1v2 strain of *Klebsiella pneumoniae* in a subject, the method comprising administering a therapeutically or prophylactically effective amount of the immunogenic composition of paragraphs 1 to 8 or 31 or the vaccine of paragraph 32, comprising a conjugate (e.g. bioconjugate) of a *Klebsiella pneumoniae* O1v1 O-antigen polysaccharide, to a subject (e.g. human) in need thereof.

36. The immunogenic composition of paragraphs 1 to 8 or 31, or the vaccine of paragraph 32, for use in inducing an immune response to *Klebsiella pneumoniae* in a subject (e.g. human).

37. The immunogenic composition of paragraphs 1 to 8 or 31, or the vaccine of paragraph 32, for use in treating or preventing a *Klebsiella pneumoniae* infection, disease or condition in a subject (e.g. human).

38. The immunogenic composition of paragraphs 1 to 8 or 31 or the vaccine of paragraph 32, comprising a conjugate (e.g. bioconjugate) of a *Klebsiella pneumoniae* O1v1 O-antigen polysaccharide, for use in treating or preventing a *Klebsiella pneumoniae* infection, disease or condition associated with an O1v2 strain of *Klebsiella pneumoniae* in a subject (e.g. human).

39. The immunogenic composition of paragraphs 1 to 8 or 31 for use in the manufacture of a medicament for inducing an immune response to *Klebsiella pneumoniae* in a subject (e.g. human).

40. The immunogenic composition of paragraphs 1 to 8 or 31 for use in the manufacture of a medicament for treating or preventing a *Klebsiella pneumoniae* infection, disease or condition in a subject (e.g. human).

41. The immunogenic composition of paragraphs 1 to 8 or 31 comprising a conjugate (e.g. bioconjugate) of a *Klebsiella pneumoniae* O1v1 O-antigen polysaccharide, for use in the manufacture of a medicament for treating or preventing a *Klebsiella pneumoniae* infection, disease or condition associated with an O1v2 strain of *Klebsiella pneumoniae* in a subject (e.g. human).

In order that this invention may be better understood, the following examples are set forth. These examples are for purposes of illustration only, and are not to be construed as limiting the scope of the invention in any manner.

EXAMPLES

Example 1: Generation of *Klebsiella pneumoniae* O1v1, O2a, O2afg, O3b O-Antigen-EPA Bioconjugates Bioconjugate-Producing Strains' Construction In order to be able to produce glycan-protein bioconjugates, *E. coli* K12 W3110 requires the following genetic modifications: i. deletion of genomic cluster involved in glycan biosynthesis and transport which could potentially negatively affect the expression of recombinant glycans; ii. introduction of the target glycan's biosynthetic genes; iii. introduction of the protein carrier's encoding gene; iv. introduction of the olygosaccharyl transferase PgIB encoding gene. The construction of glycan-production strains for the four *K. pneumoniae* serotypes varies therefore only with respect of the genes required for the glycan biosynthesis.

An *E. coli* K12 W3110-derivative strain devoid of potential interfering pathways was constructed by subsequent replacements of the targeted gene clusters with an FRT sites-flanked selection marker via A-Red homologous recombination followed by FLP recombinase-catalysed marker removal as described by Kuhlman and Cox (Nucleic Acids Res. 2010 April; 38(6): e92; also described in WO 19/30234). Five homologous recombination/marker removal steps were carried out, removing genomic sequences of:

i. O16 O-antigen cluster (rfb or wb, GenBank NCBI Reference Sequence NC_007779.1 (dated Jun. 7, 2020) position 2,114,113 to 2,103,814), ii. colanic acid cluster (wca, GenBank NCBI Reference Sequence NC_007779.1 (dated Jun. 7, 2020) position 2,138,241 to 2,118,033), iii. ECA cluster retaining wecA (wec, GenBank NCBI Reference Sequence NC_007779.1 (dated Jun. 7, 2020) position 3,666,604 to 3,656,725), iv. O16wzz2 or cld (GenBank NCBI Reference Sequence NC_007779.1 (dated Jun. 7, 2020) position 2,099,458 to 2,100,438), and v. gtrABS or yfdGHI (GenBank NCBI Reference Sequence NC_007779.1 (dated Jun. 7, 2020) position 2,473,301 to 2,475,908).

This strain is here referred as "clean strain".

This "clean strain" was the target for the insertion of the clusters. Genes wzm, wzt, wbbM, glf, wbbN, wbbO from *K. pneumoniae* (GenBank Accession No. CP052562.1 (dated May 4, 2020) position 1,695,622 to 1,702,243) were inserted into the O16 O-antigen cluster together with a selection marker (which was later removed) using known techniques (T E Kuhlman and E C Cox. Nucleic Acids Res. 2010 April; 38(6): e92.), originating the O2a glycan-producing strain.

The transcription of the inserted genes was driven by the native *E. coli* O-antigen cluster promoter and was therefore constitutive.

Genes gmlABC as in *K. pneumoniae* (GenBank Accession No. CP052562.1 (dated May 4, 2020) position 1,706, 431 to 1,703,615) were inserted into the ECA cluster (retaining wecA) of the O2a glycan-producing strain together with a selection marker (which was later removed) using known techniques (T E Kuhlman and E C Cox. Nucleic Acids Res. 2010 April; 38(6): e92.), originating the O2afg glycan-producing strain. The transcription of the inserted genes was driven by the native *E. coli* ECA cluster promoter and was therefore constitutive.

Genes wbbY and wbbZ and the DNA region in between them featuring a transcription promoter as in *K. pneumoniae* (GenBank Accession No. LT174607.1 (dated May 9, 2017) position 5,605 to 8,734) were used to replace the gene yeaS (GenBank NCBI Reference Sequence NC_007779.1 (dated Jun. 7, 2020) position 1,881,835 to 1,882,473) of the O2a glycan-producing strain together with a selection marker (which was later removed) using known techniques (T E Kuhlman and E C Cox. Nucleic Acids Res. 2010 April; 38(6): e92.), originating the O1v1 glycan-producing strain. The transcription of the inserted genes was driven by the *K. pneumoniae* promoters which are included in the inserted DNA and was constitutive.

Genes manC, manB, wzm, wzt, wbdD, wbdA, wbdB, wbdC as in *K. pneumoniae* (GenBank Accession No. LT174604.1 (dated Jun. 13, 2016)) were inserted into the O16 O-antigen cluster of the "clean strain" together with a selection marker (which was later removed) using known techniques (T E Kuhlman and E C Cox. Nucleic Acids Res. 2010 April; 38(6): e92.), originating the O3b glycan-producing strain. The transcription of the inserted genes was driven by the native *E. coli* O-antigen cluster promoter and was therefore constitutive.

The four strains were transformed with plasmids encoding the inducible expression of the oligosaccharyl transferase PgIB, the carrier protein EPA (detoxified exotoxin A from *Pseudomonas aeruginosa*) containing four PgIB glycosylation consensus sequences, and, for O3b, a further copy of the genes manC and manB, generating the respective conjugate-producing strains. The expression of these genes was inducibly expressed by isopropyl β-D-1-thiogalactopyranoside (IPTG). The used plasmids vary among the four strain due to their specific better performance in terms of bioconjugate production. The amino acid sequences of the introduced EPA (e.g. SEQ ID NO: 18) and PgIB proteins (e.g. SEQ ID NO: 15) are nevertheless identical among the four strains.

Expression of the Bioconjugates

The ability of the four strains in producing the wanted bioconjugates was assessed in protein glycosylation experiments. The experiments consist in inoculating a liquid TBdev medium culture containing the appropriate antibiotics with the conjugate-production strain, incubating it in the optimal identified temperature until optimal OD, inducing the plasmid-encoded genes with optimal Ara and/or IPTG concentration, further incubate it until the optimal harvesting time, where the optimal parameters were identified after screening several alternatives in previous experiments. Such experiments are carried out earlier in shaking flasks and later in fed-batch bioreactors. The conjugate production was assessed by extracting the periplasm's content and analysing it on SDS page which was either stained with coomassie staining or transferred on blotting membranes for the execution of Western Blot analyses.

In FIG. 1 are reported analyses of conjugates extracted from Research-level shaking flasks experiment where EPA carrier with different numbers of PglB consensus glycosylation sequences were compared. The indicated glycan-producing strains were transformed with plasmids carrying an EPA variant and a plasmid expressing PglB. To prepare a pre-culture, 5 ml TB (Terrific Broth) medium containing 10 mM MgCl$_2$ and appropriate antibiotics was inoculated with a streak of colonies from the transformation plate and grown at 37° C. o/n (overnight). The pre-culture was used to inoculate 50 ml of supplemented TB medium in a shake flask to give a starting OD600=0.1. The cultures were grown at 37° C., with 200 rpm shaking until reaching OD600=0.8-1 and then induced by addition of 0.1 mM IPTG (PglB). The expression and glycosylation of EPA variants was continued at 37° C. o/n.

A periplasmic extraction procedure was carried out. The amount of cells from o/n cultures corresponding to OD600=60 (measured using a spectrophotometer) was harvested by centrifugation. The cell pellets were resuspended in 1.5 ml of lysis buffer (30 mM Tris-HCl pH 8.5, 1 mM EDTA (Ethylenediaminetetraacetic acid), 20% sucrose) and lysozyme was added to a final concentration of 1 mg/ml. The suspensions were incubated with slight shaking for 25 minutes at 4° C. and then centrifuged at 16,000 rcf for 10 min. After centrifugation, the supernatant corresponding to periplasmic extract (PPE) was transferred to a fresh tube. Samples were detected on the gel by Coomassie staining (Fazekas de St. Groth, S.; Webster, R. G.; Datyner, A. (1963). "Two new staining procedures for quantitative estimation of proteins on electrophoretic strips". Biochimica et Biophysica Acta. 71:377-391. doi: 10.1016/0006-3002(63) 91092-8. PMID 18421828).

In order to enrich periplasmic extracts with EPA variants and allow more direct read-out by SDS-PAGE, the His-tagged EPA variants were purified using one-step purification on Ni-NTA (Nickel Nitrilo-triacetic Acid) agarose. 1 ml of PPE was mixed with 200 μl of pre-equilibrated Ni-NTA slurry and incubated with slight shaking for 30 min. After that the resin was washed and the bound protein eluted with elution buffer (30 mM Tris pH 8.0, 500 mM imidazole, 50 mM NaCl). The IMAC enriched PPE was analysed by SDS-PAGE (Laemmli, U. K. (1970). "Cleavage of Structural Proteins during the Assembly of the Head of Bacteriophage T4". Nature. 227 (5259): 680-685. Bibcode: 1970Natur.227 . . . 680L. doi: 10.1038/227680a0. ISSN 0028-0836. PMID 5432063). Samples were detected on the gel by Coomassie staining (Fazekas de St. Groth, S.; Webster, R. G.; Datyner, A. (1963). "Two new staining procedures for quantitative estimation of proteins on electrophoretic strips". Biochimica et Biophysica Acta. 71:377-391. doi:10.1016/0006-3002(63)91092-8. PMID 18421828).

The bioreactor testing of the conjugate-producing strains was carried out as follows. pH 7 phosphate-buffered TBdev medium with 50 g/L glycerol, 10 mM MgCl$_2$, antibiotics, was inoculated with the appropriate strain and stirred at 37° C. (or 35° C. for O2a) in a bioreactor vessel. Temperature was shifted to 30° C. (or kept at 37° C. for O3b) ahead of induction. Induction was carried out with 0.1 mM IPTG, and a feed was started at OD 25-40. Feed medium was phosphate-buffered at pH 7 and consists of yeast extract 67 g/L, Soy peptone 33 g/L, glycerol 250 to 300 g/L, 0.1 mM IPTG, antibiotics. Cells were harvested at 42-46 h after induction (or at 22-26 h for O3b). Samples for analyses were withdrawn at harvest.

Figure 2C:
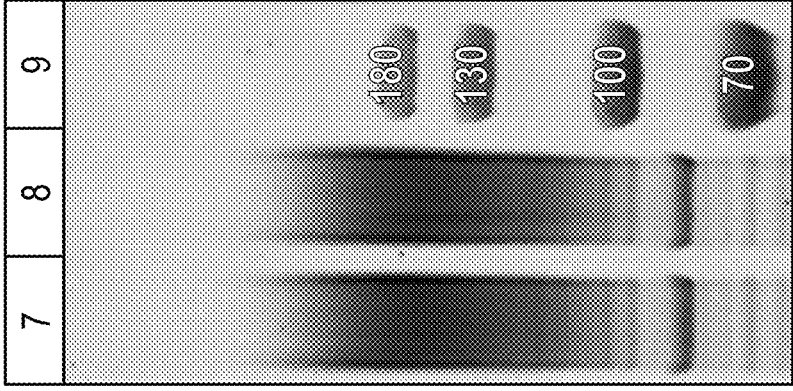

A periplasmic extraction procedure was carried out, followed by SDS-PAGE and Coomassie staining. Periplasmic extracts were also analysed by immunoblots using anti-serum raised against K. pneumoniae killed whole cells exposing the O-antigen of interest (FIG. 2).

Purified Bioconjugates

Periplasmic extraction was applied to the totality of the material harvested at the end of the growth protocol and the extracted solution was loaded into a series of chromatographic columns in order to separate contaminants and obtain a pure conjugate (FIG. 3).

Example 2: Structural Comparisons Between K. pneumoniae Natural O-Antigens and Glycan Part of Recombinantly Produced Bioconjugates NMR Analyses of LPS from K. pneumoniae Wild Type Strains The O-antigen is a part of the lipopolysaccharide (LPS). The cluster encoding the K-antigen (capsular polysaccharide) of K. pneumoniae isolates National Collection of Type Cultures (NCTC) Numbers: NCTC 13439, NCTC 9147, NCTC 11682, and NCTC 9163, expressing O-antigens O3b, O2afg, O1v1, and O2a, respectively was replaced by a kanamycin resistance cassette via homologous recombination as described (Datsenko, A. and Wanner, L. 2000, PNAS, 97 (12) 6640-6645) in order to minimize the likelihood of co-purification of the K-antigen together with the LPS. Fed-batch bioreactor cultivation was carried out for the obtained strains in order to maximize the biomass production. Cells were harvested and the LPS was extracted as described in Apicella M. A. 2008, Methods in Molecular Biology, 431:3-13 and a follow-up size exclusion chromatography was applied as described in Perdomo R. and Montero V. 2006, Biotecnología Aplicada 23:124-129.

Samples were prepared for NMR as follows. 80 mg LPS was suspended in 2 mL of 2% v/v acetic acid and hydrolyzed at 100° C. until precipitate formed. After removal of the precipitate by centrifugation and washing the pellet in 2% acetic acid, the pooled supernatant was subjected to size exclusion chromatography. Polysaccharide was separated on a Sephadex G-50 superfine column and fractions corresponding to the early peak (major) were pooled, evaporated to reduce the volume, and lyophilized. Dried polysaccharide was deuterium-exchanged by lyophilizing twice from 99.9% D$_2$O. For the NMR measurements polysaccharide was dissolved in 560 μL 99.9% D$_2$O and 4 μL 1% TSP in DO was added. The sample was centrifuged at 4,600×g for 5 min and placed into 5 mm NMR tube. $^1$H NMR and $^1$H,$^{13}$C HSQC experiments were obtained using a Bruker Avance III 600 MHz spectrometer equipped with a 5 mm TXI probe. $^{13}$C NMR spectrum was obtained using a Bruker Avance III 400 MHz spectrometer equipped with a 5 mm broadband cryo-probe Prodigy. TSP was used as a chemical shift reference in the $^1$H and $^{13}$C dimensions ($\delta_H$=0 ppm, δc=−1.6 ppm). $^1$H NMR spectrum was recorded at 30° C. and 50° C. $^{13}$C NMR and HSQC were recorded at 30° C. Results are summarized in Table 1.

NMR Analyses of the Purified Conjugates

The O1v1-EPA conjugate sample was exchanged twice with D$_2$O and then dissolved in 0.6 mL D$_2$O and transferred to a 5 mm NMR tube. NMR spectra were recorded at 323K. 1D ($^1$H & DOSY) and 2D, TOCSY and HSQC-DEPT NMR spectra were obtained using a Bruker Avance III 600 MHz NMR spectrometer equipped with a BBO Prodigy cryo-probe. The spectra were recorded and processed using standard Bruker software (Topspin 3.2). The 1D proton spectra were recorded using a 30 degree pulse and a D1 of 5 s. The 2D DOSY-TOCSY experiments was performed using a mixing time of 180 ms. The $^1$H-$^{13}$C HSQC experiment was optimized for J=145 Hz, 2D experiments were recorded using non-uniform sampling: 50% for homonuclear and 20% for heteronuclear experiments. Spectra were referenced relative to β-Galf: $^1$H at 5.21 ppm, $^{13}$C at 110.2 ppm [Vinogradov et al. Structures of Lipopolysaccharides from *Klebsiella pneumoniae*, JBC, 2002, 277, 25070-25081].

The O2a-EPA cobjugate sample was exchanged twice with $D_2O$ and then dissolved in 0.6 mL $D_2O$ and transferred to a 5 mm NMR tube. NMR spectra were recorded at 323K. 1D ($^1$H) and 2D, DOSY-TOCSY and HSQC-DEPT NMR spectra were obtained using a Bruker Avance III 600 MHz NMR spectrometer equipped with a BBO Prodigy cryoprobe. The spectra were recorded and processed using standard Bruker software (Topspin 3.2). The 1D proton spectra were recorded using a 30 degree pulse and a D1 of 5 s. 2D DOSY-TOCSY experiments were performed using a mixing time of 180 ms, the $^1$H-$^{13}$C HSQC experiment was optimized for J=145 Hz, 2D experiments were recorded using non-uniform sampling: 50% for homonuclear and 25% for heteronuclear experiments. Spectra were referenced relative to β-Galf: $^1$H at 5.22 ppm, $^{13}$C at 110.6 ppm [Clarke et al. "Molecular basis for the structural diversity in serogroup O2-antigen polysaccharides in *Klebsiella pneumoniae*." Journal of Biological Chemistry 293.13 (2018): 4666-4679].

The O2afg-EPA conjugate sample was exchanged twice with DO and then dissolved in 0.6 mL $D_2O$ and transferred to a 5 mm NMR tube. NMR spectra were recorded at 323K. 1D ($^1$H). DOSY and 2D, DOSY-TOCSY and HSQC-DEPT NMR spectra were obtained using a Bruker Avance III 600 MHz NMR spectrometer equipped with a BBO Prodigy cryoprobe. The spectra were recorded and processed using standard Bruker software (Topspin 3.2). The 1D proton spectra were recorded using a 30 degree pulse and a D1 of 5 s. The 2D DOSY-TOCSY experiment was performed using a mixing time of 180 ms; the $^1$H-$^{13}$C HSQC experiment was optimized for J=145 Hz, 2D experiments were recorded using non-uniform sampling: 50% for homonuclear and 20% for heteronuclear experiments. Spectra were referenced relative to b-Galf: $^1$H at 5.22 ppm, $^{13}$C at 110.9 ppm [Clarke et al. "Molecular basis for the structural diversity in serogroup O2-antigen polysaccharides in *Klebsiella pneumoniae*." Journal of Biological Chemistry 293.13 (2018): 4666-4679].

The O3b-EPA conjugate sample was exchanged twice with $D_2O$ then dissolved in 0.6 mL $D_2O$ and transferred to a 5 mm NMR tube for analysis. NMR spectra were recorded at 323K. 1D ($^1$H and DOSY and $^{31}$P) and 2D, COSY, DOSY-TOCSY, NOESY, HSQC-DEPT and $^1$H-$^{31}$P HMBC NMR spectra were obtained using a Bruker Avance III 600 MHz NMR spectrometer equipped with a BBO Prodigy cryoprobe. The spectra were recorded and processed using standard Bruker software (Topspin 3.2). The 1D proton spectra were recorded using a 30 degree pulse and a D1 of 5 s. The 2D DOSY-TOCSY experiment were performed using mixing time of 180 ms (1D using 200 ms) and the 2D NOESY recorded using a mixing time of 300 ms. The $^1$H-$^{13}$C HSQC-DEPT experiment was optimized for J=145 Hz and the $^1$H-$^{31}$P HMBC experiment for J=50 Hz. Spectra were referenced relative to H1/C1 of 2-α-Man: $^1$H at 5.36 ppm, $^{13}$C at 101.4 ppm and $^{31}$P at 2.08 ppm (Scientific reports 2017, 7, 6635). Results are summarized in Table 1.

TABLE 1

Comparison of relevant parameter determined by NMR studies on wild type *K. pneumoniae* LPS and on purfide glycoconjugates.

| Sero-type | Source | Structure | Degree of polymeriza-tion (average repeat units) | Degree of Gal branching[1] | Ratio gal-II vs gal-I or gal-I + gal-III |
|---|---|---|---|---|---|
| O1v1 | LPS | Confirmed | N/P | N/A | 60:40 (II:I) |
| | Conjugate | Confirmed | Gal-II: 6.1 Gal-I: 3.8 | N/A | 62:38 (II:I) |
| O2a | LPS | Confirmed | 34 | N/A | N/A |
| | Conjugate | Confirmed | 17 | N/A | N/A |
| O2afg | LPS | Confirmed | N/P | 93% | N/A |
| | Conjugate | Confirmed | 7 | 100% | N/A |
| O3b | LPS | Confirmed | 12 | N/A | N/A |
| | Conjugate | Confirmed | 12 | N/A | N/A |

[1]Percentage of Gal-III on Gal-I + Gal-III.
N/A = Not Applicable.
N/P = Not Possible.

Example 3: Animal Studies on the Conjugates: Immunogenicity of the Conjugates, Functionality and Crossreactivity of the Generated Antisera Rabbits Immunogenicity Studies The immunogenicity of the purified conjugates has been assessed in rabbit immunization studies. Monovalent and polyvalent compositions were tested for all the O-antigen-EPA conjugates. In general, groups of 5 or 6 New Zealand rabbits were immunized with monovalent or polyvalent (mixture of O1v1, O1v2, O2a, O2afg, O3 EPA conjugates, named Kp5v, or mixture of O1v1, O1v2, O2afg, O3, O3b EPA conjugates, named Kp5v1) compositions in 10 mM Na-phosphate pH 6.5, 150 mM NaCl buffer without adjuvants. Buffer only was used as control. 1 μg of total polysacchide was used for each injection. Three immunizations were carried out at day 0, 14, and 28 of the protocol. Pre-immunization, Post-II. and Post-III bleeds were harvested at day 0, 28, and 42 of the protocol, respectively, and sera were obtained. The specific antibody content of each serum was measured via enzyme-linked immunosorbent assay (ELISA) using LPS purified as described above from *K. pneumoniae* strains expressing the O-antigen of interest as coating antigen. Microtiter 96-well plates (flat-bottom polystyrene medium binding plate, Greiner cat #655001) were coated with 100 μl LPS solution per well, dilution buffer was PBS. After incubation overnight at 4° C., the plates were washed 4 times with TBS. Then 50 μl of serial three-fold dilutions (in PBS TWEEN®20 0.05% starting at 1/500) of test sera were added to each well. The plates were sealed (Alpha Labs cat #LW2770) and incubated for 2 hours at room temperature under shaking. After washing, 100 μl alkaline phosphatase conjugated goat anti-rabbit IgG (whole molecule) antibodies (Sigma cat #A3687 diluted 1:15,000) were added for 2 hours at room temperature. Plates were washed as above, and p-nitrophenyl phosphate (Sigma cat #P4744) solution in 1M diethanolamine (DEA), 0.5 mM $MgCl_2$ was added to each well (100 μl/well); plates were sealed and incubated for 1 hour at room temperature. The reaction was stopped by addition of 50 μl of 3N NaOH for 5 min and the optical density (OD) was read at 450 nm with a reference filter of 620 nm. The individual OD were referred to the endpoint titers were determined as the highest dilution above the mean OD value+10 serial dilutions of the buffer only controls. In FIG. 4 a summary of the results for polyvalent composition is reported for the conjugates of interest. Conjugates were able to elicit the production of O-antigen specific antibodies.

Functionality of the Anti O2a Conjugate Antisera

The anti-O2a antisera obtained from monovalent or polyvalent rabbit immunizations were tested for their ability to kill *Klebsiella pneumoniae* O2 in vitro with a view to using this as a proxy of the likely efficacy of specific antibodies to protect in vivo. O2a clinical isolate was grown on horse blood agar overnight at 37° C., 5% $CO_2$. The following day, single colonies were inoculated into Todd-Hewitt broth (THB) and grown at 37° C., 5% $CO_2$ to an $A_{600}$ of 0.5-0.7. Bacteria were stored at −80° C. in Tryptone Soya Broth, 10% Glycerol and washed in opsonisation buffer (OPS buffer: Hank's balanced salt solution HBSS, gelatin, fetal bovine serum FBS) prior to use. Serum samples were heat inactivated at 56° C. for 30 mins and serially diluted in OPS buffer in a 96 well round bottom plate, bacteria were incubated with serum for 30 mins at room temperature on an orbital shaker at 700 rpm. Baby rabbit complement was added to each well with human promyelocytic leukemia cells (HL-60) as the exogenous source of phagocytic cells at a concentration of $1 \times 10^7$ cells/ml and incubated for 45 mins at 37° C., 5% $CO_2$ on an orbital shaker at 680 rpm. Each plate was run with two complement controls, a heat-inactivated (control A) and an active complement control (control B); the difference between the numbers of colony forming units (CFU) for each complement control was calculated as the percentage of non-specific killing (NSK). A level of NSK below 35% was considered acceptable. The reaction was stopped by incubating on ice for 20 mins, the mixture was then spotted on to THB agar (without yeast extract) and allowed to dry. THB overlay agar (without yeast extract) was then poured over each plate and plates were inverted and incubated at 37° C., 5% $CO_2$ for 16-18 hours. CFU are counted using an automated colony counter. The opsonisation index (OI) of a sample was calculated as the dilution of serum that kills 50% of bacteria. For a sample to be considered positive, the maximum killing must be greater than 70% (samples with a maximum killing between 40% and 70% are usually repeated). Results are reported in FIG. 5. Both antisera form polyvalent and monovalent immunizations are able to bridge the killing of *K. pneumoniae* wild type strains in vitro.

Crossreactivity of Generated Antisera

Antisera obtained from rabbits' monovalent immunizations with each conjugate were tested for their ability in binding the surfaces of *K. pneumoniae* cells expressing different O-antigens by means of a flow cytometry-based assay described below. *K. pneumoniae* strains NCTC 11682, NCTC 9127, NCTC 9163, NCTC 9147, NCTC 9178, NCTC 13439, expressing O-antigen O1v1, O1v2, O2a, O2afg, O3, and O3b, respectively, were streaked on Luria-Bertani broth (LB) agar plates (Sigma-Aldrich) and were grown over night at 37° C. in a 5% $CO_2$ atmosphere. On the following day, a few colonies were re-suspended in 7 ml sterile liquid LB medium to reach an $OD_{600}$ of 0.13-0.15. The bacteria were incubated for 1 hour under rotation at 37° C. 5% $CO_2$. When the culture had reached an OD of 0.6-0.7, the bacterial suspension was diluted 5× in Dulbecco's phosphate-buffered saline (DPBS, Sigma-Aldrich) with 1% bovine serum albumin (DPBS-BSA; Sigma-Aldrich). 250 µl of this culture were transferred into the working Eppendorf tubes and spun with 13,000 rpm for 5 minutes. The supernatant was discarded and 250 µl of 1% formalin in PBS (Sigma-Aldrich) was added to fix the cells for 15 minutes at 37° C. Fixed bacteria were washed with DPBS-BSA before proceeding with any of the following steps. Fixed and washed *K. pneumoniae* cells were re-suspended in 100 µl DPBS-BSA. To each sample 2 µl of heat-inactivated anti-rabbit serum from monovalent immunizations (1:50 dilution) was added, and the samples subsequently vigorously vortexed. After 1 hour of incubation at room temperature, bacteria were spun, washed with DPBS-BSA and re-suspended in 100 µl of DPBS-BSA containing Alexa 488-conjugated secondary goat-anti-rabbit IgG antibody (1:500 dilution, SouthernBiotech, cat-nr. 4030-30, USA). After incubation for 30 minutes at room temperature in the dark, the cells were washed and re-suspended in 400 µl BD FACSFLOW™ (Thermo Fisher Scientific) before analysing the fluorescence intensities on a BD FACSCALIBUR™ (Becton Dickinson Holdings Pte. Ltd) with the FL-2 channel. Each *K. pneumoniae* strain tested for binding to antisera generated against O1v1, O1v2, O2a, O2afg, O3, and O3b conjugates. Results are reported in FIG. 6. The antibodies generated in each monovalent immunization are able to bind the *K. pneumoniae* strain expressing the corresponding O-antigen. Moreover antibodies generated by immunizing with O1v1-EPA conjugate are able to bind O1v2-expressing cells and the opposite is also true, indicating the dominance of the galactan-II antigen in eliciting antibodies. No other cross reactivities were observed. Despite the structural similarity between the O3 and the O3b O-antigens, no significant binding of anti-O3b antisera to O3b-expressing cells and the opposite was observed.

```
SEQUENCES:
SEQ ID NO: 1 Consensus sequence (artificial sequence)
D/E-X-N-Z-S/T SEQ ID NO: 2 Consensus sequence (artificial sequence)
K-D/E-X-N-Z-S/T-K SEQ ID NO: 3 Consensus sequence (artificial sequence)
K-D-Q-N-A-T-K SEQ ID NO: 4 Consensus sequence (artificial sequence)
J-D/E-X-N-Z-S/T-U SEQ ID NO: 5 Consensus sequence (artificial)
G-S-G-G-G-D/E-X-N-Z-S/T-G-S-G-G SEQ ID NO: 6 E. coli flagellin (FlgI) signal sequence
MIKFLSALILLLVTTAAQA SEQ ID NO: 7 E. coli outer membrane porin A (OmpA) signal sequence
MKKTAIAIAVALAGFATVAQA
```

-continued

SEQ ID NO: 8 *E. coli* maltose binding protein (MalE) signal sequence
MKIKTGARILALSALTTMMFSASALA SEQ ID NO: 9 *Erwinia carotovorans* pectate lyase (PelB) signal sequence
MKYLLPTAAAGLLLLAAQPAMA SEQ ID NO: 10 heat labile *E. coli* enterotoxin LTIIb signal sequence
MSFKKIIKAFVIMAALVSVQAHA SEQ ID NO: 11 *Bacillus subtilis* endoxylanase XynA signal sequence
MFKFKKKFLVGLTAAFMSISMFSATASA SEQ ID NO: 12 *E. coli* DsbA signal sequence
MKKIWLALAGLVLAFSASA SEQ ID NO: 13 *E. coli* TolB signal sequence
MKQALRVAFGFLILWASVLHA SEQ ID NO: 14 *Streptococcus agalactiae* SipA signal sequence
MKMNKKVLLTSTMAASLLSVASVQAS SEQ ID NO: 15 pglB from *Campylobacter jejuni*
MLKKEYLKNPYLVLFAMIILAYVFSVFCRFYWVWWASEFNEYFFNNQLMIISNDGYAFAEGARDMIAGFHQPND

LSYYGSSLSALTYWLYKITPFSFESIILYMSTFLSSLVVIPTILLANEYKRPLMGFVAALLASIANSYYNRTMSGYYD

TDMLVIVLPMFILFFMVRMILKKDFFSLIALPLFIGIYLWWYPSSYTLNVALIGLFLIYTLIFHRKEKIFYIAVILSSLT

LSNIAWFYQSAIIVILFALFALEQKRLNFMIIGILGSATLIFLILSGGVDPILYQLKFYIFRSDESANLTQGFMYFNVN

QTIQEVENVDLSEFMRRISGSEIVFLFSLFGFVWLLRKHKSMIMALPILVLGFLALKGGLRFTIYSVPVMALGFGFL

LSEFKAIMVKKYSQLTSNVCIVFATILTLAPVFIHIYNYKAPTVFSQNEASLLNQLKNIANREDYVVTWWDYGYPV

RYYSDVKTLVDGGKHLGKDNFFPSFALSKDEQAAANMARLSVEYTEKSFYAPQNDILKTDILQAMMKDYNQSNV

DLFLASLSKPDFKIDTPKTRDIYLYMPARMSLIFSTVASFSFINLDTGVLDKPFTFSTAYPLDVKNGEIYLSNGVVLS

DDFRSFKIGDNVVSVNSIVEINSIKQGEYKITPIDDKAQFYIFYLKDSAIPYAQFILMDKTMFNSAYVQMFFLGNY

DKNLFDLVINSRDAKVFKLKI

SEQ ID NO: 16 EPA sequence from *Pseudomonas aeruginosa*
AEEAFDLWNECAKACVLDLKDGVRSSRMSVDPAIADTNGQGVLHYSMVLEGGNDALKLAIDNALSITSDGLTIR

LEGGVEPNKPVRYSYTRQARGSWSLNWLVPIGHEKPSNIKVFIHELNAGNQLSHMSPIYTIEMGDELLAKLARDA

TFFVRAHESNEMQPTLAISHAGVSVVMAQAQPRREKRWSEWASGKVLCLLDPLDGVYNYLAQQRCNLDDTWE

GKIYRVLAGNPAKHDLDIKPTVISHRLHFPEGGSLAALTAHQACHLPLEAFTRHRQPRGWEQLEQCGYPVQRLV

ALYLAARLSWNQVDQVIRNALASPGSGGDLGEAIREQPEQARLALTLAAAESERFVRQGTGNDEAGAASADVVS

LTCPVAAGECAGPADSGDALLERNYPTGAEFLGDGGDVSFSTRGTQNWTVERLLQAHRQLEERGYVFVGYHGT

FLEAAQSIVFGGVRARSQDLDAIWRGFYIAGDPALAYGYAQDQEPDARGRIRNGALLRVYVPRWSLPGFYRTGL

TLAAPEAAGEVERLIGHPLPLRLDAITGPEEEGGRVTILGWPLAERTVVIPSAIPTDPRNVGGDLDPSSIPDKEQAI

SALPDYASQPGKPPREDLK

SEQ ID NO: 17 Modified EPA sequence with consensus sequences inserted at N-
terminal + Y208 + R274 + A519 (artificial sequence)
GSGGGDQNATGSGGGKLAEEAFDLWNECAKACVLDLKDGVRSSRMSVDPAIADTNGQGVLHYSMVLEGGNDA

LKLAIDNALSITSDGLTIRLEGGVEPNKPVRYSYTRQARGSWSLNWLVPIGHEKPSNIKVFIHELNAGNQLSHMS

PIYTIEMGDELLAKLARDATFFVRAHESNEMQPTLAISHAGVSVVMAQAQPRREKRWSEWASGKVLCLLDPLDG

VYNKDQNATKLAQQRCNLDDTWEGKIYRVLAGNPAKHDLDIKPTVISHRLHFPEGGSLAALTAHQACHLPLEAF

TKDQNATKHRQPRGWEQLEQCGYPVQRLVALYLAARLSWNQVDQVIRNALASPGSGGDLGEAIREQPEQARLA

LTLAAAESERFVRQGTGNDEAGAASADVVSLTCPVAAGECAGPADSGDALLERNYPTGAEFLGDGGDVSFSTRG

TQNWTVERLLQAHRQLEERGYVFVGYHGTFLEAAQSIVFGGVRARSQDLDAIWRGFYIAGDPALAYGYAQDQE

PDARGRIRNGALLRVYVPRWSLPGFYRTGLTLKDQNATKAPEAAGEVERLIGHPLPLRLDAITGPEEEGGRVTILG

WPLAERTVVIPSAIPTDPRNVGGDLDPSSIPDKEQAISALPDYASQPGKPPREDLK

-continued

SEQ ID NO: 18 Modified EPA sequence with consensus sequences inserted at N-
terminal + Y208 + R274 + A519 and *E. coli* DsbA signal sequence (artificial
sequence)
MKKIWLALAGLVLAFSASAGSGGGDQNATGSGGGKLAEEAFDLWNECAKACVLDLKDGVRSSRMSVDPAIADT

NGQGVLHYSMVLEGGNDALKLAIDNALSITSDGLTIRLEGGVEPNKPVRYSYTRQARGSWSLNWLVPIGHEKPS

NIKVFIHELNAGNQLSHMSPIYTIEMGDELLAKLARDATFFVRAHESNEMQPTLAISHAGVSVVMAQAQPRREKR

WSEWASGKVLCLLDPLDGVYNKDQNATKLAQQRCNLDDTWEGKIYRVLAGNPAKHDLDIKPTVISHRLHFPEG

GSLAALTAHQACHLPLEAFTKDQNATKHRQPRGWEQLEQCGYPVQRLVALYLAARLSWNQVDQVIRNALASPG

SGGDLGEAIREQPEQARLALTLAAAESERFVRQGTGNDEAGAASADVVSLTCPVAAGECAGPADSGDALLERNY

PTGAEFLGDGGDVSFSTRGTQNWTVERLLQAHRQLEERGYVFVGYHGTFLEAAQSIVFGGVRARSQDLDAIWR

GFYIAGDPALAYGYAQDQEPDARGRIRNGALLRVYVPRWSLPGFYRTGLTLKDQNATKAPEAAGEVERLIGHPLP

LRLDAITGPEEEGGRVTILGWPLAERTVVIPSAIPTDPRNVGGDLDPSSIPDKEQAISALPDYASQPGKPPREDLK

SEQ ID NO. 19 Forward primer (artificial sequence)
AAGCTAGCGCCGCCGAGGAAGCCTTCGACC SEQ ID NO. 20 Reverse primer (artificial sequence)
AAGAATTCTCAGTGGTGGTGGTGGTGGTGCTTCAGGTCCTCGCGCGGCGG SEQ ID NO: 21 *Klebsiella pneumoniae* Wzm:
ATGAAGTACAATTTAGGGTATTTATTTGATTTACTTGTTGTCATAACAAATAAAGATCTAAAAGTGCGCTATA

AGAGCAGCATGCTAGGCTATTTATGGTCAGTAGCAAATCCATTGCTTTTTGCCATGATTTATTATTTTATATT

TAAGCTGGTAATGAGAGTACAAATTCCAAATTATACCGTTTTCCTCATTACCGGCTTGTTTCCGTGGCAATGG

TTTGCCAGTTCGGCCACTAACTCATTATTTTCATTCATCGCTAACGCTCAAATTATCAAGAAGACAGTTTTTC

CCCGGTCCGTGATTCCGCTAAGTAATGTAATGATGGAAGGGTTGCATTTTCTTTGTACCATCCCGGTTATTG

TTGTCTTTCTTTTTGTTTATGGCATGACGCCGTCCTTGTCCTGGGTTTGGGGTATACCTCTCATTGCTATTGG

CCAGGTGATTTTCACCTTTGGTGTTTCAATCATCTTTTCAACGCTGAACCTGTTTTTCCGTGACCTGGAGCGC

TTTGTCAGTCTGGGGATTATGCTGATGTTTTATTGTACGCCGATTTTATATGCGTCTGATATGATTCCGGAAA

AATTTAGCTGGATAATTACCTACAATCCGCTAGCGAGTATGATTCTTAGTTGGCGTGATTTATTCATGAATGG

GACTCTTAATTATGAGTATATTTCTATACTCTATTTTACGGGAATCATTTTGACGGTTGTCGGTTTGTCTATT

TTCAATAAATTAAAATATCGATTTGCAGAGATCTTGTAA

SEQ ID NO: 22 *Klebsiella pneumoniae* Wzt:
ATGCACCCAGTTATTAACTTCAGTCATGTTACAAAAGAGTATCCTCTGTACCATCATATTGGCTCAGGAATCA

AAGATTTAATTTTCCATCCGAAACGCGCTTTTCAATTGCTGAAGGGGCGGAAATATTTAGCTATCGAAGACGT

ATCCTTTACAGTTGGCAAAGGTGAGGCTGTTGCTCTGATTGGACGTAATGGGGCAGGAAAGAGTACCTCTCT

TGGCCTGGTTGCCGGCGTGATTAAGCCAACTAAGGGAACCGTCACCACTGAAGGACGGGTGGCATCGATGC

TTGAACTCGGCGGAGGCTTTCATCCGGAACTTACCGGGCGTGAGAATATTTACCTGAATGCTACTCTGCTGG

GCCTTCGGCGTAAAGAGGTCCAGCAACGTATGGAACGTATTATTGAATTTTCGGAACTGGGAGAATTCATAG

ACGAGCCAATCAGAGTGTACTCAAGCGGAATGCTAGCTAAGTTAGGTTTTTCGGTCATCAGTCAGGTTGAAC

CGGATATTTTAATTATTGATGAAGTTCTGGCAGTAGGTGATATCGCTTTTCAGGCAAATGTATTCAGACCAT

AAGAGATTTTAAGAAAGAGGCGTGACAATATTGTTTGTTAGCCACAATATGAGTGACGTTGAAAAAATCTG

CGACAGAGTCATCTGGATCGAAATCATAGGCTCAGAGAAGTGGGGTCTGCAGAGCGAATCATTGAACTGTA

CAAGCAAGCAATGGCTTAA

SEQ ID NO: 23 *Klebsiella pneumoniae* WbbM:
ATGAACAATAGCGTTAAAATCTATACCAGCCACCATAAGCCTAGTGCTTTTCTTAATGCTGCAATTATCAAAC

CTCTGCATGTCGGCAAAGCTAATTCTTGTAATGAAATTGGTTGTCCAGGAGATGACACTGGCGATAATATTT

CCTTTAAGAATCCGTTTTATTGCGAACTTACTGCGCATTATTGGGTTTGGAAAAACGAAGAGCTGGCAGACT

ATGTCGGTTTCATGCACTATCGCCGTCATCTTAATTTTTCCGAAAAACAAACTTTTTCTGAGGATACGTGGGG

-continued

GGTCGTGAACCATCCATGCATTGATGAAGAATATGAGGAGATCTTTGGATTAAACGAAGAAACAATTCAACG

GTGTGTCGAAGGTATTGACATCTTGCTGCCCAAAAAATGGTCTGTCACTGCGGCGGGAAGTAAAAATAATTA

CGATCACTATGAACGAGGTGAATACTTACACATTCGTGATTATCAGGCTGCCATTGCCACCGTTGAAAAACTA

TATCCAGAGTATAGCACGGCAATAAAAACGTTTAATGATGCCAGTGATGGCTATTACACAAATATGTTTGTCA

TGCGCAAAGATATTTTTGTTAACTATTCTGAGTGGCTCTTTTCTATTCTGGATAATCTCGAAGATGCCATCTC

GATGAACAATTATAATGCTCAGGAAAAACGCGTTATTGGGCATATAGCAGAACGGCTGTTTAATATTTACATT

ATTAAGTTGCAACAAGATGGTGAGCTTAAGGTAAAAGAATTACAGCGTACTTTTGTCAGCAATGAAACATTCA

ATGGTGCACTGAATCCAGTTTTTGATTCTGCGGTTCCAGTGGTTATCAGTTTCGATGATAATTACGCAGTCA

GCGGTGGTGCATTAATTAATTCCATTGTCCGGCATGCGGATAAAAATAAAAATTATGATATCGTCGTGCTCG

AAAACAAAGTAAGCTATTTGAATAAAACGCGGTTAGTAAATCTAACCTCGGCTCATCCGAATATTTCTCTTCG

TTTTTTTGACGTTAATGCCTTCACTGAAATAAACGGTGTGCATACCCGAGCGCATTTTAGCGCATCAACGTAT

GCCCGTCTTTTTATTCCTCAACTGTTCAGACGATACGATAAAGTCGTATTTATTGATTCGGATACCGTTGTAA

AGGCTGACCTGGGTGAACTGCTTGATGTCCCTCTGGGCAACAATTTAGTTGCAGCGGTTAAGGATATCGTCA

TGGAAGGTTTTGTAAAATTTTCTGCAATGTCGGCATCAGATGATGGCGTTATGCCGGCAGGCGAATATTTAC

AGAAAACCTTAAATATGAATAACCCTGATGAATATTTTCAGGCAGGGATTATTGTTTTTAATGTCAAACAAAT

GGTCGAAGAAAATACTTTTGCTGAATTGATGCGGGTATTAAAGGCAAAAAAATACTGGTTCCTCGACCAGGA

TATCATGAATAAAGTATTCTACTCTCGAGTCACATTTCTGCCATTAGAGTGGAACGTTTATCATGGTAATGGC

AACACGGATGATTTCTTCCCTAATCTTAAGTTTGCAACGTATATGAAATTTTTAGCAGCTCGCAAGAAGCCTA

AAATGATTCATTATGCGGGTGAGAACAAACCATGGAATACCGAAAAAGTCGATTTTTATGACGACTTTATTGA

AAACATCGCTAACACTCCATGGGAGATGGAAATCTATAAACGTCAGATGTCGTTAGCGGCTTCGATTGGTTT

AACCCATAGCGAGCCGCAACAACAAATCTTGTTCCAGACCAAAATCAAGAACGTACTGATGCCTTATGTTAAT

AAATATGCACCAATAGGCACGCCAAGAAGAAACATGATGACTAAATATTATTACAAAGTACGCCGTGCTATTC

TTGGATAA

SEQ ID NO: 24 *Klebsiella pneumoniae* Glf:
ATGAAAAGAAAAAAAATATTGATCGTAGGCGCTGGCTTCTCTGGTGCAGTTATCGGTCGCCAACTTGCTGAG

AAGGGACATCAAGTCCATATTATCGATCAGCGTGATCATATTGGGGGGAATTCTTATGATGCACGCGACTCT

GAAACGAATGTGATGGTACATGTTTATGGACCCCATATTTTCCATACTGACAATGAATCAGTGTGGAACTATG

TCAACAAGCATGCAGAGATGATGCCCTATGTGAACCGGGTTAAAGCGACAGTTAATGGTCAGGTATTTTCCC

TGCCTATTAATTTGCATACTATCAATCAGTTTTTTCTCAAAAACTTGTTCGCCTGATGAGGCCAGAGCGCTCAT

TGCTGAGAAAGGGGACAGCACTATTGCTGATCCACAAACTTTTGAAGAGCAAGCGTTACGCTTTATTGGTAA

AGAGTTATATGAGGCCTTTTTTAAAGGATATACGATTAAACAGTGGGGGATGCAACCCTCGGAACTGCCCGC

ATCTATTCTTAAACGTCTTCCTGTTCGTTTTAACTATGACGATAATTATTTTAACCACAAATTTCAGGGCATG

CCGAAATGTGGTTATACGCAGATGATTAAGTCAATTCTTAAGCATGAGAATATCAAGGTTGACTTACAGCGG

GAATTTATCGTTGACGAGCGAACTCATTACGATCACGTATTCTATAGCGGTCCATTAGATGCGTTTTATGGCT

ACCAATATGGCCGTCTGGGCTATCGAACATTAGATTTTAAAAAGTTTATCTATCAGGGTGATTACCAGGGAT

GCGCAGTGATGAACTATTGTTCTGTGGATGTGCCCTATACTCGCATCACTGAACATAAATATTTTTCTCCCTG

GGAACAACACGACGGCTCTGTTTGTTATAAAGAGTATAGCCGTGCTTGTGAAGAAAATGATATTCCTTACTAT

CCTATTCGCCAGATGGGAGAGATGGCTCTTCTTGAAAAATATTTGTCATTGGCCGAGAATGAAACCAACATC

ACTTTTGTCGGTCGTCTTGGAACCTACCGTTACCTTGATATGGATGTGACCATCGCCGAAGCATTGAAAACG

GCAGAAGTCTATTTAAATTCACTCACTGAAAATCAGCCAATGCCTGTGTTTACGGTTTCTGTACGATGA

-continued

SEQ ID NO: 25 *Klebsiella pneumoniae* wbbN:
ATGAAATATACGGCATTGATAGTGACATTCAATCGTCTCGGCAAACTGAAAAAAACGGTTGAAGAGACCCTC

AAACTTGAATTCACTAATATTGTTATTGTCAATAACGGGTCCACGGATGGGACCCAAGCCTGGCTTTCGTCAA

TTGTTGATACACGAGTCATTGTATTAACCCTCACCGAGAATACCGGTGGGGCGGGGGGCTTTAAAACCGGTA

GTCAGTATATCTGTGAACAGCTGGCAAGTGATTGGGTATTTTTCTACGATGACGATGCTTACCCCTATCCAG

ACACGTTGAAGTCCTTTTCACAGCTGGATAAGCAGGGATGTCGGGTATTTAGTGGACTGGTGAAAGATCCGC

AAGGAAAACCGTGTCCGATGAATATGCCGTTCTCGCGTGTGCCAACTTCCCTTGGCGACACTGTACGCTATT

TACGCTACCCTGCAGAGTTTATCCCGGCAGCTAATCGTTCTATGTTCGTACAAACGGTTTCATTTGTTGGGAT

GGTCATACATCGTGATCTGCTCGCGACCAGTCTTGACCACATCCATGAACAGCTCTTTATCTACTTTGATGAT

CTTTACTTTGGCTATCAGCTATCATTAGCTGGTGAGCAAATTATGTATAGCCCGGAGTTGCTTTTTTATCATG

ATGTGAGTATTCAGGGCAAACTTATTGCCCCTGAATGGAAGGTTTACTATCTATGCCGTAATTTGATCCTGTC

GAAGAAAATATTCCAGAAAAATGCCGTATATAGCAATTCAGCGATAGCGATACGCATCCTAAAATATATATTA

ATCCTGCCATGGCAACGTCAAAAATATTCCTATATGAAATTTATTCTTCGTGGAATTTCACATGGCATAAAAG

GTATTAGTGGTAAGTATCATTAA

SEQ ID NO: 26 *Klebsiella pneumoniae* wbbO:
ATGAGAAAATTGTGTTATTTCATAAATTCGGATTGGTACTTCGATTTACACTGGATCGATCGTGCCATCGCCT

CCCGTGATGCAGGTTATGAGATTCACATCATCAGCCATTTTATTGATGACAACATAATAAATAAATTTAAAAC

ATTTGGCTTTATTTGCCATAATGTTACTCTTGATGCTCAATCTTTTAATGCATTAGTTTTCTTTCGTACTTACC

ATGATGTGCAAAAAATTATTAAAAATATAAAACCGGATCTCTTGCATTGCATCACTATCAAGCCATGTTTGAT

TGGTGGTGTGCTCGCGAAGAAATTTAATCTGCCGGTCATCGTAAGTTTTGTTGGGCTTGGAAGAGTATTTTC

TTCTGACAGCATGCCTTTAAAATTATTGCGGCAGTTTACTATTGCTGCATATAAATATATTGCCAGTAATAAG

CGCTGTATATTTATGTTTGAACATGACCGCGACAGAAAAAAACTGGCTAAGTTGGTTGGACTCGAAGAACAA

CAGACTATTGTTATTGATGGTGCAGGCATTAATCCAGAGATATACAAATATTCTCTTGAACAGGATCACGATG

TCCCTGTTGTATTGTTTGCCAGCCGTATGTTGTGGAGTAAAGGACTGGGCGACTTAATTGAAGCGAAGAAAA

TATTACGCAGTAAGAATATTCACTTTACTTTGAATGTTGCTGGAATTCTGGTCGAAAATGATAAAGATGCAAT

TTCCCTTCAGGTCATTGAAAATTGGCATCAGCAAGGATTAATTAACTGGTTAGGTCGTTCGAATAACGTTTGC

GATCTTATTGAGCAATCAAATATCGTTGCTTTGCCGTCAGTTTATTCTGAAGGTGTTCCGCGAATTCTTCTGG

AAGCATCTTCTGTGGGGCGCGCTTGTATTGCTTATGATGTTGGTGGTTGTGATAGCCTTATTATTGATAACG

ATAATGGAATTATTGTTAAAAGCAATTCACCTGAAGAGCTGGCTGATAAACTTGCCTTTTTGCTTAGCAATCC

TAAAGCACGCGTTGAAATGGGTATTAAGGGGAGGAAACGTATACAAGATAAATTTTCTAGTGTTATGATTAT

CGATAAAACATTGCAAATATATCATGATGTAGTTCGATGA

SEQ ID NO: 27 *Klebsiella pneumoniae* gmlA:
ATGCCAAGTTCAGGCCCATTATGGCAACTAATGAAATATGGGTTAGTTGGGATAGTCAATACACTAATTACG

GCAGTTGTAATTTTCCTGCTAATGCATTTGGGTCTTGGCATTTATCTGTCCAATGCGATGGGTTATGTTGTA

GGTATTGTTTTCAGCTTTATAGCAAACACAATATTTACATTTACGCAACCAATCAGTATCAATAGACTAATAA

AATTTTTATGTGTTTGCTTCATTTGTTATGTGGCAAATATCATTGTCATAAAAATATTTTTCGTTTTTATGCCA

GAAAAAATATATTCAGCACAAATCCTTGGGATGTTCACATACACTATCACAGGTTTTATTTTAAACAAGTTCT

GGGCGATGAAATGA

SEQ ID NO: 28 *Klebsiella pneumoniae* gmlB:
ATGACAACCTCAACTGATATAAAAAGCACTCCTTCTTTAGCTATTGTGGTACCTTGCTATAATGAACAAGAGG

CTTTTCCTTTCTGTCTCGAAAAGCTTTCGAATGTACTAAATTCATTGATAGCCAGAAATAAAATTAATAACAAT

AGTTATCTTTTGTTTGTCGATGATGGTAGTCGTGACAATACTTGGGCACAAATTAAAGATGCCTCGACCGCT

TATCACTATGTGCGAGGAATAAAATTATCAAGAAATAAAGGACATCAAATTGCGTTGATGGCAGGGTTACGC

-continued

TCGGTCGATACAGACGTAAGCATTAGCATCGATGCGGATCTACAAGACGATGTAAATTGCATCGAAAAAATG

ATTGACGCTTACAGCCAGGGATATGACATAGTATACGGCGTAAGAGGTAATCGAGACAGTGACACGTTTTTT

AAACGTACAACAGCTAATGCATTTTACGCAATAATGTCCCACTTGGGAGTAAATCAAACTCCAAATCATGCAG

ATTATCGATTATTAAGTAATCGAGCATTGGAGGCTCTTAAACAATATAAAGAGCAAAATATATATTTACGTGG

ATTAGTGCCTCTTGTGGGATACCCCTCGATCGAGGTGCAATATAGCCGTGAAGAAAGAATTGCAGGTGAATC

AAAATATCCAATTAAAAAAATGCTTGCGCTGGCTCTCGAGGGAATTACCTCATTATCAGTTACACCGTTACGA

ATTATAGCTATGACAGGTTTTATAACTTGCATCATATCAACCATCGCTGCGATTTATGCTTTAATTCAAAAAA

CAACAGGTACTACAGTTGAGGGATGGACATCAGTCATGATCGCTATATTCTTTCTTGGCGGCGTGCAAATGC

TTTCTTTAGGTATTATAGGAGAATATGTCGGAAAAATTTATATAGAGACGAAAAATAGACCTAAATATTTCAT

TGACGAAAGCGTAGGTAATGATAGCAATGGAAAATAA

SEQ ID NO: 29 *Klebsiella pneumoniae* gmlC:
ATGCAAAATCTGATCAATCCTTTAGCAGAGGGAAATAAAAAAAACGTTTACATTTTTTATTTCTTTTTGCTTAT

GTTAACATTTTCACCGGTAATTTTCTTTTCATATGCATTTTCAGACGACTGGTCAACACTCTTTGATGCTATA

ACAAGAAACGGCTCTTCGTTTCAGTGGGATGTCCAATCTGGTCGTCCCGTTTATGCTGTGTTCCGTTACTAT

GGAAAAATGTTAATTAATGATATTTCTTCATTTTCGTATTTGCGGCTTTTTAATATATTAAGTCTTGTTGTCT

TAAGTTGTTTTATTTACAACTTCATAGACAGCAGAAAAATATTTGATAACCCCGTATTCAAAATAACATTTCCG

CTGTTAATTTGCTTACTCCCTGCGTTTCAAGTTTATGCTTCATGGGCAACATGTTTCCCGTTCACTATTTCAG

TATTGCTGGCAGGTATTAGTTATAATAAATGTTTCCCACATTCGAAGCAGCGGTCGTCATTGTCAGAAAAATT

AGCATCCATTGTTGTCTTATGGGTGGCATTTGCAATATATCAACCGACAGCAATTACATTCTTATTCTTTTTT

ATGCTTGATAGTTGTATAAAAAAAGAAAGTAGTTTAACTGTGAAAAAAGTTGCGACATGTTTTATCATTTTAG

TTATCGGTGTTGCAGGCAGTTTTATAATGTCAAAAGTACTTCCTGTCTGGCTATATGGGGAATCATTATCGA

GAGCCGAGTTAACCGCAGATATCGGTGGAAAGATGAAATGGTTCATAAATGAATCACTAATAAACGCTGTAA

ATAACTATAACATACAACCAGTAAAAATATATTCTTGGTTCTCCTCGCTTGCAATTTTAATCGGCTTATACACT

ATTTTTGTGGGAAAATCAGGCAGATGGAAAACGTTCATAGTCATAGCGATCGGGATAGGTTCCTACGCTCCA

AATTTAGCGACAAAAGAGAATTGGGCAGCATTCCGCTCGTTAGTGGCCTTAGAACTTATTATATCAACTCTAT

TTCTTATTGGCATAAATAGCCTTGTCAGTAGAATTTTTAAGCAAGCATTTGTCTGGCCTCTTATCGCTTTAAC

AATTATGATAATAGCTCAGTATAATATTATAAATGGATTTATTATTCCTCAACGCTCTGAAATTCAGGCACTT

GCTGCGGAAATAACTAATAAAATACCTAAGAATTACACAGGAAAATTAATGTTCGATCTCACAGATCCCGCTT

ACAATGCCTTTACAAAAACACAGAGATATGATGAATTTGGGAATATTTCATTAGCAGCACCCTGGGCGCTCAA

AGGTATGGCTGAAGAGATCAGAATTATGAAAGGATTTAATTTCAAACTATCTAACAACGTTATAGTTTCTGAG

ACCAATCGATGTATTGATGATTGTATGGTTATCAAAACGTCAGATGCAATGCGAAGGTCAACGATAAATTATT

AG

SEQ ID NO: 30 *Klebsiella pneumoniae* wbbY:
ATGAAGAAAATTCTTATAATGACGCCGGACATTGAGGGGCCTGTCCGTAACGGCGGTATTGGTACTGCTTTC

ACTGCCCTTGCCACTACTTTGGCAAAAAAGGGGTATGATGTTGATGTATTGTATACATGTGGCGACTATTCT

GAATCATCTGTATCGAAATTTAGCGACTGGTCACGTATTTATAGTACCTTTGGTATCAATCTGCTAAGAACCG

GACTGATAAAAGAGATTAATATTGATGCACCGTATTTTAGAAGGAAAAGTTATTCAATTTATCTCTGGTTGAA

AGAAAATAACACCTATGACACTGTTATTTCTTGTGAGTGGCAGGCAGATCTTTATTACACTTTATTAAGCAAA

AAGAATGGAACGGATTTTGAAAATACAAAGTTCATTGTAAATACTCACAGTTCAACGTTATGGGCTGATGAA

GGTAATTACCAGCTTCCATATGATCAGAACCATCTTGAACTCTATTATATGGAGAAAATGGTGGTTGAAATGG

CGGATGAAGTTGTTAGTCCGTCTCAGTATTTAATTGATTGGATGTTGAGTAAGCACTGGAATGTTCCTGAAG

-continued

```
AACGTCATGTAATTTTAAATTGCGAGCCATTTCAAGGGTTTGTGACGAGAGATGATGTTACAGTTAAAATAAA

TGAAAAGCCAGCTTCTGGCGTTGAGCTTGTATTTTTCGGCCGCCTTGAAACCCGTAAAGGACTTGACATATT

CCTGCGTGCATTAAGAAAACTATCTGATGAAGATAAAGAGAGCATTTCTGGAGTAACCTTCCTCGGAAAAAT

GTCACTATGGGGAAAACTGATTCATTTACTTATATTATGAATCAGACTAAAAATTTGGGACTCGCAGTTAATG

TCATCAGCGACTATGATCGTACCAACGCTAATGAATATATAAAAAGAAAAAATGTATTAGTCATCATTCCATC

ACTTGTAGAAAACTCACCCTATACTGTTTATGAATGTTTGATTAATAACGTTAATTTTCTCGCTTCAAACGTT

GGTGGAATTCCAGAGCTTATTCCGCAGGAGCATCATGCGGAAGTTCTATTTATTCCTACACCTGCCGATTTAT

ACGGAAAAATCCACTATCGCTTAAAAAATATAAATATAAAACCAGGGCTTGCTGAATCACAAGACAATATTAA

AGAAGCTTGGTTTGTCGCAGTTGAACGAAAAAACAACCGCACATTCAAGAAATCGATGAAGCTAACAGCCC

GTTAGTTAGCGTGTGTATAACTCACTTCGAACGTCACCATTTGCTTCAGCAAGCACTCGCATCAATAAAATCT

CAGACGTACCAAAATATTGAGGTCATCTTGGTTGATGATGGAAGTACGACAGAAGATTCTCATCGTTATTTG

AATCTCATCGAGAATGATTTTAACTCTCGAGGCTGGAAAATTGTCCGTAGTTCTAATAACTATCTGGGTGCTG

CAAGGAATTTGGCTGCGCGACACGCCTCTGGCGAATATCTGATGTTTATGGACGATGATAATGTTGCTAAGC

CTTTTGAGGTAGAAACGTTTGTTACTGCAGCATTAAACTCTGGGGCCGATGTGTTAACCACACCAAGCGATC

TTATTTTTGGTGAGGAGTTCCCTTCTCCGTTCCGTAAAATGACGCACTGCTGGCTTCCGTTAGGGCCTGATT

TAAATATCGCCAGCTTTAGTAACTGCTTTGGCGATGCTAATGCGCTGATCAGAAAAGAGGTTTTCGAAAAAG

TAGGCGGATTTACTGAAGATTACGGTTTAGGTCATGAAGACTGGGAGTTTTTTGCCAAAATATCATTACAGG

GATATAAATTGCAAATCGTCCCGGAACCTCTATTTTGGTATAGAGTTGCAAACTCCGGCATGTTGTTAAGTG

GAAATAAGAGTAAAAATAACTACCGCAGTTTCCGTCCTTTTATGGATGAGAATGTTAAATATAACTATGCAAT

GGGGTTGATACCTTCCTACCTCGAGAAGATTCAAGAACTTGAGAGTGAAGTGAATCGCTTGCGGAGCATCAA

TGGTGGTCATTCTGTCAGTAACGAGTTACAACTTTTAAATAATAAGGTTGATGGTCTTATTTCTCAGCAAAGA

GATGGCTGGGCCCATGACCGTTTTAATGCTCTGTATGAAGCAATTCATGTCCAAGGCGCAAAACGAGGCACC

AGCCTGGTTCGCCGGGTTGCCCGGAAAGTGAAATCAATGTTAAAATAA
```

SEQ ID NO: 31 *Klebsiella pneumoniae* wbbZ:
```
ATGACCAATATGAAGTTAAAATTTGATTTGCTTCTAAAATCTTATCATCTATCTCATCGATTTGTCTATAAGGC

AAACCCTGGTAATGCTGGTGATGGTGTAATTGCATCTGCGACGTATGACTTTTTTGAACGAAATGCTCTTAC

CTATATCCCTTACAGAGATGGCGAGCGCTACAGTTCTGAAACTGATATTTTAATTTTTGGAGGCGGAGGAAA

CCTGATAGAAGGATTGTATTCTGAAGGTCATGACTTTATCCAGAATAATATTGGGAAGTTTCATAAAGTAATA

ATAATGCCGTCGACAATCAGAGGGTATAGCGATTTATTCATCAACAATATTGATAAGTTTGTTGTTTTTTGTC

GCGAAAATATCACCTTCGATTATATTAAATCTCTCAACTACGAACCAAACAAGAACGTATTCATTACTGATGA

TATGGCATTTTATCTCGATCTTAATAAATACCTGTCACTTAAACCCGTCTATAAAAAACAGGCCAACTGCTTC

AGAACGGACTCCGAATCTCTAACTGGAGACTACAAAGAAAACAATCATGATATTTCGCTCACCTGGAATGGC

GATTATTGGGATAATGAATTTCTGGCGCGTAATTCTACCCGTTGCATGATAAACTTTCTTGAAGAGTATAAAG

TTGTCAATACCGACAGGCTGCATGTGGCAATTTTAGCATCTCTGCTTGGCAAAGAAGTCAACTTCTATCCTAA

CTCATATTACAAAAATGAAGCTGTTTACAATTATTCACTTTTTAATCGTTATCCAAAAACATGCTTTATTACGG

CAAGTTGA
```

SEQ ID NO: 32 *Klebsiella pneumoniae* manC:
```
ATGTTGCTTCCTGTGATCATGGCTGGTGGTACCGGCAGTCGTCTCTGGCCGATGTCTCGCGAGCTTTACCCG

AAACAGTTCCTCCGCCTGTTCGGGCAGAACTCCATGCTGCAGGAAACCATCACCCGACTCTCGGGCCTTGAA

ATCCATGAACCGATGGTCATCTGTAACGAAGAGCACCGCTTCCTGGTGGCCGAACAGCTGCGCCAGCTCAAC

AAGCTGTCGAACAACATTATTCTTGAGCCGGTCGGGCGCAACACCGCCCCGGCCATCGCCCTGGCGGCCCTC

CAGGCCACCCGCCACGGCGACGACCCGCTGATGCTGGTCCTCGCCGCCGACCATATCATCAATAACCAGCCG
```

-continued

GTCTTCCACGACGCCATCCGCGTCGCCGAGCAGTATGCCGATGAAGGCCATCTGGTCACCTTCGGTATCGTG

CCGAACGCCCCGGAAACCGGCTACGGCTACATCCAGCGCGGCGTGGCCCTCACCGACAGCGCCCACACCCCG

TACCAGGTGGCCCGCTTCGTGGAGAAGCCGGACCGCGAGCGCGCCGAGGCCTACCTCGCCTCCGGGGAGTA

CTACTGGAACAGCGGCATGTTTATGTTCCGCGCCAAAAAATACCTCTCCGAGCTGGCCAAATTCCGCCCGGA

TATCCTCGAAGCCTGCCAGGCCGCGGTCAATGCCGCCGATAACGGCAGCGACTTCATCAGCATCCCGCATGA

CATTTTCTGTGAGTGCCCGGACGAGTCCGTGGACTACGCCGGTGATGGAGAAAACCGCCGACGCGGTGGTGG

TCGGTCTCGATGCCGACTGGAGCGACGTCGGCTCCTGGTCCGCCCTGTGGGAGGTCAGCCCGAAAGATGAG

CAGGGTAACGTCCTCAGCGGCGACGCGTGGGTGCACAACAGCGAAAACTGCTACATCAACAGCGACGAGAA

GCTGGTGGCGGCCATCGGCGTGGAGAACCTGGTGATTGTCAGCACCAAGGACGCCGTGCTGGTGATGAACC

GTGAGCGTTCCCAGGACGTGAAGAAGGCGGTCGAGTTCCTCAAGCAGAACCAGCGCAGCGAGTACAAGCGC

CACCGCGAGATTTACCGTCCCTGGGGCCGCTGCGACGTGGTGGTCCAGACCCCGCGCTTCAACGTCAACCGT

ATTACGGTGAAACCGGGCGGCGCGCCTTCTCGATGCAGATGCACCACCACCGTGCCGAGCACTGGGTCATTCTC

GCCGGCACCGGCCAGGTGACGGTCAACGGCAAGCAGTTCCTGCTGACCGAGAACCAGTCCACCTTTATTCCG

ATTGGCGCCGAGCACAGCCTGGAAAACCCGGGCCGCATTCCGCTGGAAGTGCTGGAGATCCAGTCGGGGTC

GTACCTCGGCGAGGACGACATTATTCGTATTAAAGACCAGTATGGTCGTTGCTAA

SEQ ID NO: 33 *Klebsiella pneumoniae* manB:
ATGACACAGTTAACATGCTTTAAGGCTTATGACATCCGTGGTGAACTGGGCGAGGAGCTGAACGAGGACATC

GCCTACCGTATCGGCCGCGCCTATGGCGAATTTCTGAAACCCGGGAAGATAGTGGTGGGGGGCGATGTGCG

CCTCACCAGCGAGTCGCTGAAGCTGGCGCTGGCCCGCGGGCTGATGGACGCCGGCACCGACGTGCTGGATA

TTGGCCTGAGCGGCACGGAAGAGATTTACTTCGCCACTTTCCACCTCGGGGTGGACGGCGGTATCGAGGTG

ACGGCGAGCCATAACCCGATGAACTACAACGGCATGAAGCTGGTGCGCGAGAACGCGAAGCCCATCAGCGG

CGACACCGGCCTGCGGGATATCCAGCGCCTGGCGGAGGAGAATCAGTTCGCGCCGGTAGACCCGGCGCGTC

GCGGGACCCTGCGCCAGATATCGGTGCTGAAGGAGTACGTCGACCACCTGATGGGCTATGTGGACCTGGCG

AACTTCACCCGTCCGCTGAAGCTGGTGGTGAACTCCGGCAACGGGCGGCGGGGCACGTGATTGATGAAGT

GGAGAAACGCTTCGCGGCGGCCGGGGCGCCGGTGACCTTTATCAAGGTGCATCACCAGCCGGACGGCCATT

TCCCGAACGGTATCCCGAACCCGCTGCTGCCGGAGTGCCGCCAGGACACCGCCGACGCGGTGCGTGCGCAT

CAGGCGGACATGGGGATCGCCTTTGACGGCGACTTCGACCGCTGCTTCCTGTTCGATGACGAGGCGTCGTTT

ATCGAGGGGTACTACATTGTCGGCCTGCTGGCGGAGGCGTTCCTGCAGAAACAGCCGGGGGCGAAAATCAT

TCACGACCCGCGTCTGACGTGGAACACGGTGGACATCGTGACCCGCAGCGGCGGCCAGCCGGTGATGTCGA

AGACGGGGCATGCGTTCATCAAGGAGCGGATGCGCCAGGAAGACGCCATCTACGGCGGGGAAATGAGTGCG

CACCATTACTTCCGCGACTTCGCCTACTGCGACAGCGGGATGATCCCGTGGCTGCTGGTGGCGGAGCTGCTG

TGCCTGAAGAACAGTTCGCTGAAATCGCTGGTGGCGGACCGCCAGGCGGCGTTCCCGGCGTCGGGGGAGAT

CAACCGCAAGCTGGGGAATGCGGCGGAGGCGATAGCGCGCATCCGGGCGCAGTATGAGCGGGCCGCCGCAC

ACATCGACACAACGGACGGTATCAGTATTGAATACCCTGAGTGGCGCTTTAACCTGCGCACGTCCAACACGG

AGCCGGTGGTGCGTCTGAACGTTGAGTCCAGAGCGGATACTGCGTTAATGAATGAGAAAACCGCCGAGCTG

CTCAACCTGTTAAAAGAGGAATCGCTTTGA

SEQ ID NO: 34 *Klebsiella pneumoniae* wzm:
ATGGTTTTCAGCGATCTATCGCTACCGTGGCTTTATTATTGACAGCGTCAAACGGGACTTTCAGTCCCGTTACC

AGACTAGCTTCTTAGGCGCGGCATGGCTGATCTTACAGCCGATCGCCATGATTTCCGTATATACATTAATCTT

TTCTGAGTTAATGCGTGCCCGCCTGGCGGGCATGGACGGCCCTTTTGCCTACAGTATCTACCTCTGTTCCGG

GGTGTTAACCTGGGGGCTGTTTACGGAAACGCTCGGCAATCTGGTCAACGTTTTTCTGACCAACGCCAACAT

-continued

TCTTAAAAAGCTTAGCTTTCCGCGGATCTGTTTACCGATCATTGTCACCGCCTCGGCGTTCATTAACTTCCTG

ATCATTTTTGGTCTGTTTGTACTGTTTCTGATCGTCACGGGCAATTTCCCGGGCATGATTTTCTTTGAAATCA

TTCCGGTGCTGATCGTTCAGATGCTGTTCACCCTCGGCCTCGGGATCATCCTCGGGGTGCTGAACGTTTTTG

TCCGCGACGTCGGGCAGTTCGTGAATATCCTGCTGCAGTTTTGGTTCTGGTTTACGCCCATTGTCTACGTGT

CCAAAACGCTGCCGGAGTGGGTCTCTGGTCTGCTGGCGTATAACCCGATGGCGACCATTATCGGTTCATACC

AGAACGTGATGCTCTATCACCAGAGCCCTAACTGGCTGGCGCTGCTTCCGGTCACGGTGCTGTCCGTCATTC

TGTTTTTATTTGCCTGGCGTTTATTTAAAAAACATGCCGCTGATATTGTGGACGAGATTTAA

SEQ ID NO: 35 *Klebsiella pneumoniae* Wzt:
ATGAGTATCAAAGTTCAGCACGTCGGCAAGGCGTATAAATATTATCCCTCCAAATGGAACCGGGTCATTGAG

AAACTTCTGCCGGGCGATAAGCCGCGGCACAGCAAGAAATGGGTATTGAAAGATATCAATTTCAGTATTGAA

CCCGGTGAAGCGGTCGGCATTGTTGGGGTGAACGGCGCAGGTAAAAGTACGTTACTGAAGCTGCTGACTGG

CACCACTCAGCCGACCAAAGGCAGCATTGAGATCCAGGGGCGTGTCGCTGCGCTGCTGGAGCTGGGCATGG

GCTTCCATCCTGACTTTACCGGTCGGCAGAACGTGTATATGTCCGGGCTGATGATGGGCCTGAGCCGGGAA

GAGATTGAGCGCTTAATGCCGGAGATCGAAGCCTTTGCGGATATCGGTGACTACATTGAAGAGCCCGTGCGC

ATCTACTCCAGCGGGATGCAAATGCGCCTGGCGTTCGCCGTGGCCACGGCCTCACGCCCGGATATTCTGATC

GTCGATGAAGCGCTTTCCGTTGGTGACTCCCGCTTTCAGGCGAAGTGCTATGCCCGTATTGCGGACTTCAAA

AAGCAGGGCACCACGCTGCTGCTGGTCTCCCACAGCGCCGGGGATATCGTCAAACACTGTGACCGCGCCATT

TTCCTCAAAAATGGTGATATCTGTATGGACGGCACCGCCCGTGACGTGACCAACCGTTATCTGGATGAGCTG

TTTGGCAAAGCCGACAAAAACAGCGCGCCAAAAAGCGAAACGGCAACCTCGTCAGCCAGCGGCGAAAGTCAG

ATGTCTCTCGATGAGATTGAAGATGTGTACCACACGCGCCCAGGCTACCGTCCGGAAGAGTACCGTTGGGGG

CAGGGGGGTGCAAAAATCATTGATTATCACATCCAAAGCGCCGGGGGTTGATTTTCCGCCTTCACTGACGGGC

AATCAGCAGACCGATTTCCTGATGAAAGTCGTATTTGAATATGACTTTGATTGCGTGGTACCGGGTTTGTTA

ATCAAAACTCTGGATGGCTTATTTCTATATGGTACCAACTCTTTCCTGGCCTCGGAAGGCCGGGAAAACATTT

CGGTATCACGTGGGGACGTTAGAGTATTTAAATTCAGTTTTCCGGTTGATTTAAATAGCGGTGACTATCTTC

TGTCGTTTGGTATTTCAGAGGGAAGCCCGCAAACCGAAATGACGCCGCTCGATCGTCGCTATGACTCCATCA

TTTTGCATGTAACTAAGAGCATGGATTTCTGGGGAGTGATTGACCTGAAGTCGACTTTCAATAGTTACAAAT

GA

SEQ ID NO: 36 *Klebsiella pneumoniae* wbdD
ATGACTACTAATACACATAAATTGGTTAGCGAATTACCTGAAATTTATCAGACTATTTTTGGGCATCCTGAGT

GGGATGGCGATGCTGCACGAGACTGTAATGAACGGCTCGCGCTAATTAGTGAACAATATGACAGCTTGTCCA

GAGAGTTAGGAAGGCCACTACGGGTTCTCGACCTGGGCTGTGCTCAGGGGTTCTTCAGTTTAAGTTTGGCAA

GCAAGGGTGCCAGCGTATTAGGTATCGACTTTTTGCAGCAGAACATTGATGTTTGTCAGGCGCTTGCTGAAG

AAAATCCACATTGTGATGTTAAATTTCAAGTCGGGCGGATAGAAGACATTGTCAGCACTCTGGAAGAAACC

AATTTGATCTCGCCATTGGACTAAGTGTTTTTCACCACATTGTTCATCTGCATGGGGTTGCTGAAGTCAGATC

GCTGTTAGAGCGTTTGGCAAATCTGACGCAGGCGATGATTCTCGAGCTCGCTGTCAAGGAGGAACCACTCTA

TTGGGGGAAATCTCAGCCTGAAGATCCGCGTGAACTTATTGACCAATGTGCTTTCTATCGATTGATTGGAAG

ATTTGACACTCATCTGTCTAATATTTCACGTCCGATGTATATTATCAGTAACCACAGGGTTATTCTTCCGGAA

TTTAATCAGCCTTTTACTTCATGGCGCGACAGTCCTTACACCGGAGCAGGCTTTGCGCATAAACAGAGCCGT

CGCTATTATTTCTCTTCGGAGTTCATATGTAAGTTCTATCGTTTTAGTACAGTAAGTTGCTTACTAACTGATA

AGGAGAGCGAGCGTAATCGTACTGAACTCGCCCATGAAGAAGCTTTTCTTAAATCTCCACCATCTGGCTTAAA

AGTGCCGGCGTTGTTTACTGCAGGGGGGAATGGAGAAGCGGGATGGTGGTAATGGAAAAAATTCCCGGAG

AGCTGTTAAACGACGTTCTGGCCAGTGAACGGCATATTGATCGGGAAAAAGTTATTTCCGATCTCCTCGACC

-continued

```
AATTAGTTATTTTGGAAGAACATGGTCTATATCATGATGATTTCAGAACATGGAATGTTTTAATTGACGATAA

TGACAGCGCTCGTTTAATAGATTTTGGTTCGATTGGCGATGTACAACAAGACTGCAGCTGGCCAGTTAATAT

TTTCCAGTCGTTCATTATTTTTGTAAATGAAATATTTTGTGAAAATAAATCCTGGAGGGGCTTCTGGCGTTCC

GCACCATTAAGTCCTTTCCAGTTGCCTGAACCGTATTCAAATTGGTTGACAGCATTCTGGAAACATCCTGTTG

GTGAGTGGAGTTTTGCTTTACTCCAACAACTCTTTTCAACCAAAGATGCTCTACCGGCTGCGAGTTCCATTAT

GGACGCTTCTGATCTATGGGTCCGGGCTCAGGAGCCCGTATTGTTGGAAAGTCAAACGCAAATACGCAATAC

GGATGCGCGGGTAGTCCGTCTCGAGTCGCAAATCAATGAACTCACCTCCCTGATTAATATTATGGGTGAGAG

CATTCAGACGTTTGAGAAGCGTGAGTATCCGCCACAAGACGTTACTACTAATGTACAGCCGCGTATCGAGAT

TGAGCAGAGTAAAGCCGTTGATTCAGAAGAGATTATGCGACTTCATACGCAGCTCAATGATGCTCAGCAAGA

AATAGAGAATCTACGTCATGAGATTGCTAAAATTCATTATAGTCGCTCATGGAAAATGACCAAGTGGTATCG

GTACGCTGGCTTACAGTACTATCTGCTTCGTCAGTACGGCTTCAAACAGCGTTTTAAGCATTTACTCAAACGA

GTGCTTAGCAACGTAATTTATTTTTTGCGTGCACATCCACGACTAAAGCAGAAGGTGATCAATCTACTGCGTA

CAATTGGAATTTATGACTTTGCTTATCGTATGCATCGTCGTATGAATCCTGGTTCACATAACCCTTATCCAAA

CGACCCACAATACCAGTCGCAGACTGAAAAGCAGATCTTACATCCAGAGTTATTGCCTCCGGAAGTTAACTCA

ATTTTTAGCGAGCTTAAAAACAAAAGATAA
```

SEQ ID NO: 37 *Klebsiella pneumoniae wbdA*:
```
TTGCATATTTTGATTGACGTACAAGGATATCAATCGGAAAGTAAATTCCGTGGAGTTGGTCGCAGCACCTAT

GAAATGAGTCGTGCGATCATAAAAAATGCTGGCCAGCATCGAGTAAGCATTTTAATGAATGGCATGTATTCG

ATTGATAGTATAAATGAAATTAAAAAAAGCTGGGGTGATATATTACCGCAGGAAGAAATGTTTATTTTTTCAG

CTGCTGGCCCTACAGCTCTTCGCGACTGTGAAAACCATCCCCGGAGTGTTGCCGCCACACTAGCTCGTGAAC

TTGCTATTGCTAATATCAATCCCGACGTTGTTTTTATTATTAATTTCTACGAAGGTTTTGACGATAGTTATAC

CGTCTCAATTCCTCAAACTACAGTACCATGGAAAACAGTTTGTGTTTGTCACGATCTAATTCCGTTACTGAAT

AAAGAACGCTATCTGGGCGAACCAAACTTCCGTCAGTATTATTATGATAAACTAGCTCAATACGAAAGGGCG

GACGCTATTTTTGCTATTTCCAGATCATCCATGCAGGAAGTTATCGATTACACATCGATTCCGGCAGAAAAAA

TTATTAATATTTCATCTGGAGTAAGCGATTCATTTAAAATTAAAGATTATACTCACGATGAAATCAAAGACTT

ACGTAATAAATATCATCTTCCTCAAGAGTTTATTCTTTCTTTGGCAATGATAGAGCCACGTAAAAATATTGAA

GCGCTGATTCATGCATATAGTTTATTACCGCATGCCCTGCAACAGAGTTATCCCTTAGTTTTAGCCTATAAAA

TTAGCACCGATGAAAAGGAAAGGCTGTACCGAGTTGCAGAGAACTATGGTTTATCTCGTAATCAGCTTATTT

TTACAGGCTTCTTAAACGATAGTGACCTTATCGCACTTTACAATTTGTGCAAAATTTTCGTTTTCCCCTCTAT

ACATGAAGGGTTTGGCCTGCCGCCACTAGAAGCTATGCGTTGTGGTGCAGCTACGCTGGGTTCAAATGTGAC

CAGCTTACCCGAGGTCATCGGTATGGAAGAGGCTTTATTTAATCCTCTGGATGTCCCCGACATTTGCCGTGT

TATGCAAAGGGCCTTGACTGACAGTGAGTTCTACTCAGCATTAAAAGCTCATGCTCCGGCGCAGGCGGCAAA

GTTCACATGGGATCACACCGCGCAGCTCGCGTTAAAGGGATTTGAGAGGCTTGTAGATAAGGCTTCCGCATC

AGAACCTCTGGATATCACAAGCTTCACCGCATACACCATTAATAGAATTAAAAATATTGCAGAATTAAGTGAA

ACCGAACGCTTACAGACAGCCTGGGCGATTGCTCGTAATAGCTTTGCTACACATCAGCGCAAGCTGCTGGTT

GATATTTCTGTTCTTGTTGAGCATGATGCGAAAACGGGAATTCAACGGGTTTCTCGCAGTATACTTAGTGAA

TTACTGAAATCTGGCGTTGCTGGTTATACTGTCAGTGCGGTTTATTATCGACCGGGTGAATGCTATCGCTAT

GCCAACGAATACCTGAATACCCATTTTAACGGGGCGTTCGGGCCTGATGTACCTGTACTGTTTACCAAAGAT

GATATTCTGGTTGCTACCGATCTAACTGCCCATCTGTTTCCTGAGCTTACTGTCCAGCTGGATTTTATTCGTC

TATCCGGTGCCAAGGTTTGTTTTTGTTGTGCATGACATTTTGCCTCTGAGAAGACCGGAGTGGAGCGATGAGG

GAATGCAACGCGTGTTCCCCATTTGGTTATCTTGCATTGCGCAGCACGCAGACCGCTTGATTTGTGTATCAG
```

-continued

CAAGCGTTGCAGAGGATGTAAAAGCCTGGATTGCGGAAAACAGCCATTGGGTGAAACCGAACCCGCTGCTGA

CCGTCAGCAACTTCCATCTGGGAGCCGACCTCGATGCCAGCGTACCGTCCACTGGCATGCCGGATAATGCCC

AGGCGCTGTTAGCAGCGATGGCCGCGGCTCCATCATTTATCATGGTGGGCACGATGGAACCACGCAAAGGA

CATGCGCAGACGCTAGCGGCATTTGAAGAATTGTGGTTACAGGGCAAGAACTACAATCTGTTTATCATTGGT

AAACAGGGGTGGCATGTTGATGATTTATGTGAACGTTTACGTCACCATCCACAGCTAAATAAAAAACTATTTT

GGCTACAAAACATTAGCGATGAGTTCCTTACGAAGTTGTATTCTCAGTCTAGTGCGTTAATCTTCGCATCTCT

CGGAGAAGGCTTTGGCCTGCCGTTGATTGAAGCGGCGCAGAAAAAGCTGCCGGTGATTATCCGTGACATTCC

GGTGTTTAAAGAGATTGCTCAGGAACATGCGTGGTATTTCTCCGGGGAAGCGCCGGCCGACATCGCGAAGG

CCGTCGAAGACTGGTTAGCCCTGTATGAGCAAAACGCGCATCCTCGTTCCGAGAATATCAACTGGTTAACCT

GGAAGCAGAGCGCGGAATTTCTCCTGAAAAACCTGCCGATTATCGCGCCAGCCGCGAAGCAATAA

SEQ ID NO: 38 *Klebsiella pneumoniae* wbdB:
ATGAAAATTATTTTTGCTACTGAGCCAATTAAATACCCGTTAACGGGCATCGGTCGGTATTCCCTGGAGCTG

GTTAAGCGGCTGGCGGTCGCCCGCGAAATCGAAGAGCTGAAGCTGTTTCACGGCGCGTCGTTTATCGATCA

GATCCCCCAGGTGGAGAATAAAAGCGATACCAAAGCCAGCAATCATGGTCGTTTGTCGGCGTTTCTGCGCCG

CCAGCCGCTGCTGATTGAGGCGTATCGCCTGCTGCACCCGCGGCGCCAGGCGTGGGCATTGCGCGACTATA

AAGATTATATCTACCATGGTCCCAATTTTTACCTGCCGCATCGCCTGGAACACGCCGTGACCACGTTTCATGA

CATCTCCATTTTTACCTGCCCGGAATATCATCCAAAAGATCGGGTTCGCTATATGGAGAAGTCCCTGCATGAG

AGCCTGGATTCGGCAAAGCTGATCCTGACCGTCTCTGACTTCTCGCGCAGTGAAATCATCCGCCTGTTCAAC

TATCCGGCGGAGCGGATCGTCACCACCAAGCTGGCCTGCAGCAGCGACTATATTCCACGCAGCCCGGCGGAG

TGCCTGCCGGTCCTGCAGAAATATCAGCTGGCGTGGCAGGGGTATGCGTTATATATCGGCACCATGGAGCC

GCGTAAAAATATCCGTGGTCTGCTGCAGGCCTATCAGCTGCTGCCGATGGAGACCCGCATGCGCTACCCGCT

GATCCTCAGCGGCTATCGCGGCTGGGAAGACGATGTGCTGTGGCAGTTAGTCGAGCGTGGTACGCGTGAAG

GGTGGATCCGTTACCTGGGCTATGTCCCGGATGAGGACCTGCCTTATCTGTACGCGGCGGCCAGAACCTTTG

TTTATCCCTCCTTCTATGAGGGATTCGGTTTACCTATTCTTGAAGCGATGTCTTGCGGTGTGCCGGTAGTAT

GTTCCAATGTCACTTCTTTGCCTGAGGTGGTTGGCGATGCCGGCCTCGTTGCCGATCCTAATGATGTAGACG

CGATTAGCGCGCATATTTTGCAGAGCCTGCAGGATGATAGCTGGCGGGAAATCGCCACCGCGCGCGGTCTT

GCCCAGGCGAAACAGTTTTCGTGGGAGAACTGTACGACCCAGACCATTAACGCCTATAAATTACTCTAA

SEQ ID NO: 39 *Klebsiella pneumoniae* wbdC:
TTGAGAGTTCTACACGTCTATAAGACCTACTATCCCGATACCTACGGCGGTATTGAGCAGGTCATTTATCAGC

TCAGTCAGGGTTGCGCCCGCCGGGGGATCGCAGCCGATGTTTTTACTTTTAGCCCGGACAAAGAGACAGGTC

CTGTCGCCTACGAAGACCATCGGGTCATTTATAATAAGCAGCTTTTTGAAATTGCCTCCACGCCGTTTTCGTT

GAAAGCGTTAAAGCGTTTTAAGCAGATTAAAGATGATTACGACATCATCAACTACCATTTTCCGTTTCCCTTT

ATGGATATGCTGCATCTCTCGGCGCGGCCTGACGCCAGAACGGTGGTGACCTATCACTCGGATATTGTGAAA

CAAAAACGGTTGATGAAGTTGTACCAGCCGCTGCAGGAGCGATTCCTCGCCAGCGTAGACTGCATTGTTGCC

TCGTCGCCCAACTACGTGGCCTCCAGCCAGACCCTGAAAAAATATCAGGATAAAACGGTGGTGATCCCGTTT

GGTCTGGAGCAGCATGACGTGCAGCACGATCCGCAGCGGGTGGCGCACTGGCGGGAAACCGTCGGCGATAA

CTTCTTCCTCTTCGTCGGCGCTTTCCGCTACTACAAAGGGCTGCACATTCTGCTGGATGCCGCCGAGCGTAG

CCGGCTGCCAGTGGTGATCGTCGGGGGCGGGCCGCTGGAGGCGGAGGTGCGGCGTGAGGCGCAGCAGCGC

GGACTGAGCAATGTGGTGTTTACCGGCATGCTCAACGACGAAGATAAATACATTCTCTTCCAGCTCTGCCGG

GGCGTGGTCTTCCCCTCGCATCTGCGCTCAGAGGCGTTTGGCATTACGTTACTGGAAGGCGCGCGCTTTGCC

AGGCCGCTGATCTCCTGCGAGATCGGCACCGGTACCTCGTTCATTAACCAGGACAAAGTAAATGGCTGCGTG

-continued

ATCCCGCCGAATGACAGTCAGGCGCTGGTGGAGGCGATGAATGAGCTCTGGCATAACGATGAAACCGCCAG

CCGCTATGGCGAAAACTCGCGTCGTCGTTTTGAAGAGATGTTTACAGCCGACCATATGATTGACGCTTACGT

CAATCTCTACACTACGCTGCTGGAAAGCAAATCCTGA

SEQ ID NO: 40 PCR primer
5'-GAAGGCGGGCGCGTGACCA TTCTCGGC

SEQ ID NO: 41 PCR primer
GCCGAGAATGGTCACGCGCCCGCCTTC

---

The invention claimed is:

1. A host cell comprising:

i) first nucleotide sequences, which are integrated into the host cell genome and comprise polysaccharide synthesis genes for producing a *Klebsiella pneumoniae* O-antigen polysaccharide, the *Klebsiella pneumoniae* O-antigen polysaccharide comprising a O1v1 O-antigen polysaccharide, a O2a O-antigen polysaccharide, a O2afg O-antigen polysaccharide, or a O3b O-antigen polysaccharide;

ii) a second nucleotide sequence, which is within one or more plasmids and encodes a heterologous oligosaccharyl transferase;

iii) a third nucleotide sequence, which is within the one or more plasmids and encodes a carrier protein, the carrier protein comprising an inserted consensus sequence: the inserted consensus sequence comprising: D/E-X-N-Z-S/T, wherein X and Z is any natural amino acid except proline; and iv) a fourth nucleotide sequence, which encodes an ABC transporter, the fourth nucleotide sequence comprising *Klebsiella pneumoniae* wzm gene and *Klebsiella pneumoniae* wzt gene.

2. The host cell according to claim 1, wherein the polysaccharide synthesis genes for producing the *Klebsiella pneumoniae* O-antigen polysaccharide comprise *Klebsiella pneumoniae* wbbM gene, *Klebsiella pneumoniae* glf gene, *Klebsiella pneumoniae* wbbN gene, and *Klebsiella pneumoniae* wbbO gene.

3. The host cell according to claim 1, wherein the polysaccharide synthesis genes for producing a *Klebsiella pneumoniae* O-antigen polysaccharide comprise *Klebsiella pneumoniae* wbbM gene, *Klebsiella pneumoniae* glf gene,

*Klebsiella pneumoniae* wbbN gene, *Klebsiella pneumoniae* wbbO gene, *Klebsiella pneumoniae* gmlA gene, *Klebsiella pneumoniae* gmlB gene, and *Klebsiella pneumoniae* gmlC gene.

4. The host cell according to claim 1, wherein the polysaccharide synthesis genes for producing a *Klebsiella pneumoniae* O-antigen polysaccharide comprise *Klebsiella pneumoniae* wbbM gene, *Klebsiella pneumoniae* glf gene, *Klebsiella pneumoniae* wbbN gene, *Klebsiella pneumoniae* wbbO gene, *Klebsiella pneumoniae* wbbY gene, and *Klebsiella pneumoniae* wbbZ gene.

5. The host cell according to claim 1, wherein the polysaccharide synthesis genes for producing a *Klebsiella pneumoniae* O-antigen polysaccharide comprise *Klebsiella pneumoniae* manC gene, *Klebsiella pneumoniae* manB gene, *Klebsiella pneumoniae* wbdD gene, *Klebsiella pneumoniae* wbdA gene, *Klebsiella pneumoniae* wbdB gene, and *Klebsiella pneumoniae* wbdC gene.

6. A conjugate comprising a carrier protein and a *Klebsiella pneumoniae* O-antigen polysaccharide: the *Klebsiella pneumoniae* O-antigen polysaccharide comprising a O1v1 O-antigen polysaccharide, a O2a O-antigen polysaccharide, a O2afg O-antigen polysaccharide, or a O3b O-antigen polysaccharide; the *Klebsiella pneumoniae* O-antigen polysaccharide being conjugated to the carrier protein, and the carrier protein being a detoxified Exotoxin A of *Pseudomonas aeruginosa*:

wherein the O1v1 O-antigen polysaccharide has the structure of -(D-galactan II)n-(D-galactan I)m-GlcNAc, as follows:

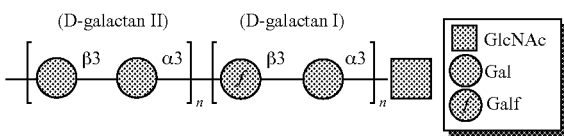

wherein: (i) the number of repeat units of the D-galactan II (n) is from 5 to 7; (ii) the number of repeat units of the D-galactan I (m) is from 3 to 5; and (iii) the ratio of the D-galactan II to the D-galactan I is from 2:1 to 1:50;

wherein the O2a O-antigen polysaccharide has the structure of -(D-galactan I)p-GlcNAc, as follows:

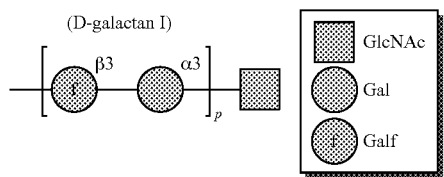

wherein the number of repeat units of the D-galactan I (p) is from 15 to 30;

wherein the O2afg O-antigen polysaccharide has the structure of -(D-galactan III)r-GlcNAc, as follows:

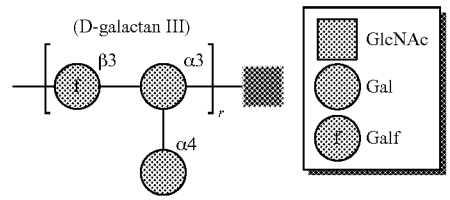

wherein the number of repeat units of the D-galactan III (r) is from 5 to 15;

wherein the O3b O-antigen polysaccharide has the structure of Me-P-3(Man-α2-Man-α3-Man-α3)s-Man-α3-Man-α3-GlcNAc, as follows:

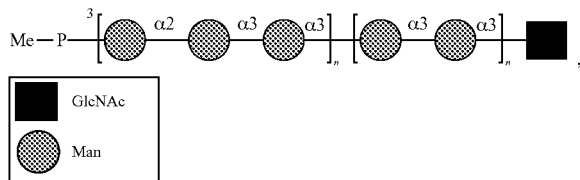

wherein the number of repeat units of the Man-α2-Man-α3-Man-α3 (s) is from 10 to 20.

7. The conjugate according to claim 6, wherein the *Klebsiella pneumoniae* O-antigen polysaccharide is the O1v1 O-antigen polysaccharide.

8. The conjugate according to claim 6, wherein the *Klebsiella pneumoniae* O-antigen polysaccharide is the O2a O-antigen polysaccharide.

9. The conjugate according to claim 6, wherein the *Klebsiella pneumoniae* O-antigen polysaccharide is the O2afg O-antigen polysaccharide.

10. The conjugate of claim 6, wherein the degree of branching of the O2afg O-antigen polysaccharide ranges from 90% to 100%.

11. The conjugate according to claim 6, wherein the *Klebsiella pneumoniae* O-antigen polysaccharide is the O3b O-antigen polysaccharide.

12. An immunogenic composition comprising: (a) the conjugate of claim 6 and (b)(i) a pharmaceutically acceptable excipient or (b)(ii) a pharmaceutically acceptable carrier.

13. An immunogenic composition comprising one or more carrier proteins, a *Klebsiella pneumoniae* O1v1 O-antigen polysaccharide, a *Klebsiella pneumoniae* O2a O-antigen polysaccharide, a *Klebsiella pneumoniae* O2afg O-antigen polysaccharide, and a *Klebsiella pneumoniae* O3b O-antigen polysaccharide, wherein each of the *Klebsiella pneumoniae* O1v1 antigen polysaccharide, the *Klebsiella pneumoniae* O2a O-antigen polysaccharide, the *Klebsiella pneumoniae* O2afg O-antigen polysaccharide, and the *Klebsiella pneumoniae* O3b O-antigen polysaccharide are conjugated to the one or more carrier proteins.

14. The immunogenic composition according to claim 13, wherein the one or more carrier proteins comprise an inserted consensus sequence; the inserted consensus sequence comprising D/E-X-N-Z-S/T, wherein X and Z is any natural amino acid except proline.

15. A vaccine comprising the immunogenic composition of claim 12 and an adjuvant.

16. A vaccine comprising the immunogenic composition of claim 13 and an adjuvant.

17. A vaccine comprising the immunogenic composition of claim 14 and an adjuvant.

18. A method of inducing an immune response to *Klebsiella pneumoniae* in a subject, the method comprising administering a therapeutically or prophylactically effective amount of the immunogenic composition of claim 12 to the subject.

19. A method of inducing an immune response to *Klebsiella pneumoniae* in a subject, the method comprising administering a therapeutically or prophylactically effective amount of the immunogenic composition of claim 13 to the subject.

20. A method of inducing an immune response to *Klebsiella pneumoniae* in a subject, the method comprising administering a therapeutically or prophylactically effective amount of the immunogenic composition of claim 14 to the subject.

21. The host cell according to claim 1, wherein the *Klebsiella pneumoniae* wzm gene comprises a sequence at least 95% identical to SEQ ID NO: 21 or SEQ ID NO: 34 and the *Klebsiella pneumoniae* wzt gene comprises a sequence at least 95% identical to SEQ ID NO: 22 or SEQ ID NO: 35.

22. The host cell according to claim 2, wherein: (a) the *Klebsiella pneumoniae* wzm gene comprises a sequence at least 95% identical to SEQ ID NO: 21 or SEQ ID NO: 34, (b) the *Klebsiella pneumoniae* wzt gene comprises a sequence at least 95% identical to SEQ ID NO: 22 or SEQ ID NO: 35, (c) the *Klebsiella pneumoniae* gene wbbM comprises a sequence at least 95% identical to SEQ ID NO: 23, (d) the *Klebsiella pneumoniae* gene glf comprises a sequence at least 95% identical to SEQ ID NO: 24, (e) the *Klebsiella pneumoniae* gene wbbN comprises a sequence at least 95% identical to SEQ ID NO: 25, and (f) the *Klebsiella pneumoniae* gene wbbO comprises a sequence at least 95% identical to SEQ ID NO: 26.

23. The host cell according to claim 3, wherein: (a) the *Klebsiella pneumoniae* wzm gene comprises a sequence at least 95% identical to SEQ ID NO: 21 or SEQ ID NO: 34, (b) the *Klebsiella pneumoniae* wzt gene comprises a sequence at least 95% identical to SEQ ID NO: 22 or SEQ ID NO: 35, (c) the *Klebsiella pneumoniae* wbbM gene comprises a sequence at least 95% identical to SEQ ID NO: 23, (d) the *Klebsiella pneumoniae* glf gene comprises a sequence at least 95% identical to SEQ ID NO: 24, (e) the *Klebsiella pneumoniae* wbbN gene comprises a sequence at least 95% identical to SEQ ID NO: 25, (f) the *Klebsiella pneumoniae* wbbO gene comprises a sequence at least 95% identical to SEQ ID NO: 26, (g) the *Klebsiella pneumoniae* gmlA gene comprises a sequence at least 95% identical to SEQ ID NO: 27, (h) the *Klebsiella pneumoniae* gmlB gene comprises a sequence at least 95% identical to SEQ ID NO: 28, and (i) the *Klebsiella pneumoniae* gmlC gene comprises a sequence at least 95% identical to SEQ ID NO: 29.

24. The host cell according to claim 4, wherein: (a) the *Klebsiella pneumoniae* wzm gene comprises a sequence at least 95% identical to SEQ ID NO: 21 or SEQ ID NO: 34, (b) the *Klebsiella pneumoniae* wzt gene comprises a sequence at least 95% identical to SEQ ID NO: 22 or SEQ ID NO: 35, (c) the *Klebsiella pneumoniae* wbbM gene comprises a sequence at least 95% identical to SEQ ID NO: 23, (d) the *Klebsiella pneumoniae* glf gene comprises a sequence at least 95% identical to SEQ ID NO: 24, (e) the

*Klebsiella pneumoniae* wbbN gene comprises a sequence at least 95% identical to SEQ ID NO: 25, (f) the *Klebsiella pneumoniae* wbbO gene comprises a sequence at least 95% identical to SEQ ID NO: 26, (g) the *Klebsiella pneumoniae* wbbY gene comprises a sequence at least 95% identical to SEQ ID NO: 30, and (h) the *Klebsiella pneumoniae* wbbZ gene comprises a sequence at least 95% identical to SEQ ID NO: 31.

25. The host cell according to claim 5, wherein: (a) the *Klebsiella pneumoniae* wzm gene comprises a sequence at least 95% identical to SEQ ID NO: 21 or SEQ ID NO: 34, (b) the *Klebsiella pneumoniae* wzt gene comprises a sequence at least 95% identical to SEQ ID NO: 22 or SEQ ID NO: 35, (c) the *Klebsiella pneumoniae* manC gene comprises a sequence at least 95% identical to SEQ ID NO: 32, (d) the *Klebsiella pneumoniae* manB gene comprises a sequence at least 95% identical to SEQ ID NO: 33, (e) the *Klebsiella pneumoniae* wbdD gene comprises a sequence at least 95% identical to SEQ ID NO: 36, (f) the *Klebsiella pneumoniae* wbdA gene comprises a sequence at least 95% identical to SEQ ID NO: 37, (g) the *Klebsiella pneumoniae* wbdB gene comprises a sequence at least 95% identical to SEQ ID NO: 38, and (h) the *Klebsiella pneumoniae* wbdC gene comprises a sequence at least 95% identical to SEQ ID NO: 39.

\* \* \* \* \*